(12) United States Patent
Rigby et al.

(10) Patent No.: US 6,525,070 B2
(45) Date of Patent: Feb. 25, 2003

(54) BIPIPERIDINE DERIVATIVES AS MODULATORS OF CCR3 ACTIVITY AND AS H1 ANTAGONISTS

(75) Inventors: Aaron Rigby, Loughborough (GB); Hitesh Sanganee, Loughborough (GB); Brian Springthorpe, Loughborough (GB); Louise Lawrence, Quorn (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/827,488

(22) Filed: Apr. 6, 2001

(65) Prior Publication Data

US 2002/0077337 A1 Jun. 20, 2002

(30) Foreign Application Priority Data

| Apr. 8, 2000 | (GB) | 0008626 |
| Aug. 3, 2000 | (GB) | 0019111 |
| Oct. 11, 2000 | (SE) | 0003664 |

(51) Int. Cl.$^7$ .................. A61K 31/4465; C07D 211/36; C07D 211/58
(52) U.S. Cl. ...................... 514/316; 546/188; 546/189; 546/191
(58) Field of Search ................ 546/188, 189, 546/191; 514/316

(56) References Cited

U.S. PATENT DOCUMENTS

| 4,695,575 A | 9/1987 | Janssens et al. |
| 5,977,138 A | * 11/1999 | Wang et al. ............... 514/316 |
| 6,066,636 A | 5/2000 | Kozlowski et al. |

FOREIGN PATENT DOCUMENTS

| EP | 0 099 139 | 1/1984 |
| EP | 0 145 037 | 6/1985 |
| EP | 0 151 824 | 8/1985 |
| EP | 0 151 826 | 8/1985 |
| WO | WO 96/34857 | 11/1996 |
| WO | WO 98/01425 | 1/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO 00/00488 | 1/2000 |
| WO | WO 00/66559 | 11/2000 |
| WO | 0066559 | * 11/2000 |

* cited by examiner

*Primary Examiner*—Alan L. Rotman
*Assistant Examiner*—Rita Desai
(74) *Attorney, Agent, or Firm*—Fish & Richardson P.C.

(57) ABSTRACT

The present invention provides a compound of a formula (I):

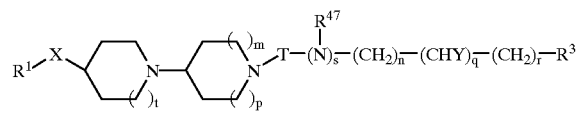

(I)

wherein the variables are defined herein; to a process for preparing such a compound; and to the use of such a compound in the treatment of a chemokine (such as CCR3) or H1 mediated disease state.

13 Claims, No Drawings

BIPIPERIDINE DERIVATIVES AS MODULATORS OF CCR3 ACTIVITY AND AS H1 ANTAGONISTS

FIELD AND BRIEF SUMMARY OF THE INVENTION

The present invention concerns piperidine derivatives having pharmaceutical activity, to processes for preparing such derivatives, to pharmaceutical compositions comprising such derivatives and to the use of such derivatives as active therapeutic agents.

DESCRIPTION OF RELATED ART

Pharmaceutically active piperidine derivatives are disclosed in WO99/38514, WO99/04794 and WO00/35877.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys—X—Cys (C—X—C, or α) and Cys—Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria. H1 antagonists are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204–8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

DETAILED DESCRIPTION OF THE INVENTION

The present invention provides a compound of formula (I):

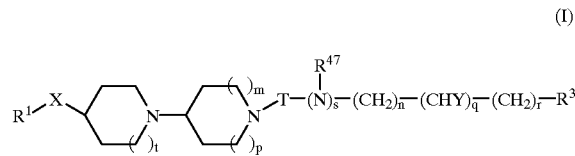

(I)

wherein:

q, s and t are, independently, 0 or 1;

n and r are, independently, 0, 1, 2, 3, 4 or 5;

m and p are, independently, 0, 1 or 2;

X is $CH_2$, $C(O)$, O, S, $S(O)$, $S(O)_2$ or $NR^{37}$; provided that when m and p are both 1 then X is not $CH_2$;

Y is $NHR^2$ or OH;

T is $C(O)$, $C(S)$, $S(O)_2$ or $CH_2$;

$R^1$ is hydrogen, $C_{1-6}$ alkyl, aryl or heterocyclyl;

$R^2$ and $R^{47}$ are, independently, hydrogen, $C_{1-6}$ alkyl, aryl($C_{1-4}$)alkyl or $CO(C_{1-6}$ alkyl);

$R^3$ is $C_{1-6}$ alkyl {optionally substituted by halogen, $CO_2R^4$ or phthalimide}, $CR^{3a}R^{3b}R^{3c}$, $C_{2-4}$ alkenyl {optionally substituted by aryl or heterocyclyl}, $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl, heterocyclyl, thioaryl or thioheterocyclyl;

$R^{3a}$ is hydrogen, $C_{1-6}$ alkyl, $C_{1-6}$ alkoxy or $C_{3-7}$ cycloalkyl; $R^{3b}$ is aryl, heterocyclyl, $S(O)_2$aryl or $S(O)_2$heterocyclyl; and $R^{3c}$ is $C_{1-6}$ alkyl, $C_{1-4}$ haloalkyl, hydroxy, heterocyclyl($C_{1-4}$ alkyl) or aryl;

wherein, unless stated otherwise, the foregoing aryl and heterocyclyl moieties are optionally substituted by: halogen, OH, SH, $NO_2$, oxo, $C_{1-6}$ alkyl {itself optionally substituted by halogen, $OC(O)C_{1-6}$ alkyl, $S(O)_2R^{48}$, phenyl (itself optionally substituted by halogen (such as one or two chlorine or fluorine atoms), $C_{1-6}$ alkyl, $S(O)_2R^{38}$ or $C(O)NR^{39}R^{40}$), naphthyloxy (itself optionally substituted by halo or $C_{2-6}$ alkenyl), $C_{3-10}$ cycloalkyl (itself optionally substituted by $C_{1-4}$ alkyl or oxo) or $NR^{41}C(O)OCH_2$(fluoren-9-yl)}, $NR^{41}(O)$ $OCH_2$(fluoren-9-yl), $C_{1-6}$ alkoxy {itself optionally substituted by halogen, $C_{1-6}$ alkoxy, $NHCO_2(C_{1-6}$ alkyl), $CO_2R^4$, $NR^5R^6$ or phenyl (itself optionally substituted by halogen or $NO_2$)}, $C_{1-6}$ alkylthio, $C_{1-6}$ haloalkylthio, $C_{3-10}$ cycloalkyl, $NR^7R^8$, $NR^9C(O)R^{10}$, $CO_2R^{11}$, $C(O)NR^{12}R^{13}$, $C(O)R^{14}$, $S(O)_dR^{15}$, $S(O)_2NR^{42}R^{43}$, $NR^{44}S(O)_2R^{45}$, phenyl {itself optionally substituted by halogen, $C_{1-6}$ alkyl, $C_{1-6}$ haloalkyl, CN, $NO_2$, $C_{1-6}$ alkoxy (itself optionally substituted by halogen, OH or pyridinyl), phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, heterocyclyl {itself optionally substituted by halogen, $C_{1-6}$ alkyl, $C_{1-6}$ haloalkyl, CN, $NO_2$, $C_{1-6}$ alkoxy, $C_{1-6}$ haloalkoxy, phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, phenoxy {itself optionally substituted by halogen, $C_{1-6}$ alkyl, $C_{1-6}$ haloalkyl, CN, $NO_2$, $C_{1-6}$ alkoxy, $C_{1-6}$ haloalkoxy, phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, SCN, CN, $SO_3H$ (or an alkali metal salt thereof), methylenedioxy or difluoromethylenedioxy; when aryl is phenyl adjacent substituents may join to form, together with the phenyl ring to which they are attached, a dihydrophenanthrene moiety;

d is 0, 1 or 2;

$R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl, aryl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocylyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy);

$R^{15}$, $R^{38}$, $R^{45}$ and $R^{48}$ are, independently, $C_{1-6}$ alkyl (optionally substituted by halogen, hydroxy or $C_{3-10}$ cycloalkyl), $C_{3-6}$ alkenyl, aryl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy);

or an N-oxide thereof; or a pharmaceutically acceptable salt thereof; or a solvate thereof;

provided that:

when m and p are both 1, n, q and r are all 0, T and X are both $S(O)_2$, and $R^1$ is methoxyphenyl then $R^3$ is not propyl; when m, p, q and r are all 1, n is 0, Y is $NH_2$, T is CO and $R^1X$ is $(CH_3)_2N$ then $R^3$ is not 3,5-dibromo-4-aminophenyl, 1-methylindol-3-yl or 1-(tert-butoxycarbonyl)indol-3-yl; and when m and p are both 1, n, q and r are all 0, T is CO, X is NH and $R^1$ is 3-(4-fluorobenzyl)benzimidazol-2-yl then $R^3$ is not 4-fluorophenyl.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, acetate, diacetate, fumarate, maleate, tartrate, citrate, oxalate, methanesulphonate or p-toluenesulphonate. Another example of an addition salt is sulphate.

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl or tert-butyl.

Alkenyl group are, for example, vinyl or allyl.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system).

Cycloalkenyl is especially monocyclic and is, for example, cyclopentenyl or cyclohexenyl.

Aryl is preferably phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin-4-one-yl), a benzothiazinyl (for example in 4H-benzo[1,4]thiazin-3-one-yl), benzo[d]imidazo[2,1-b]thiazol-2-yl or dibenzothiophenyl (also known as dibenzothienyl); or an N-oxide thereof, or an S-oxide or S-dioxide thereof.

In one aspect of the invention heterocyclyl is an aromatic or non-aromatic 5 or 6 membered ring, optionally fused to one or more other rings, comprising at least one heteroatom selected from the group comprising nitrogen, oxygen and sulphur. Heterocyclyl is, for example, furyl, thienyl, 2,1,3-benzothiadiazole, 2,1,3-benzoxadiazole, quinoxaline, dihydro-1-benzopyrylium (for example a coumarin or a chromone), piperidine, morpholine, pyrrole, indole, 2,3-dihydroindole, quinoline, thiazole, pyrazole, isoxazole, imidazole, pyridine, benzofuryl, benzimidazole, pyrimidine or dibenzothiophene.

In a further aspect heterocyclyl is an aromatic or non-aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl, pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example 1-dioxo-2,3-dihydrobenz[b]thienyl), benzimidazolyl, benztriazolyl, benzoxazolyl, benzthiazolyl, 2,3-dihydrobenzthiazolyl (for example 2,3-dihydrobenzthiazol-2-onyl), 1,2,3-benzothiadiazolyl, 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopyryliumyl (for example a coumarinyl or a chromonyl), 3,4-dihydro-1H-2,1-benzothiazinyl (for example 2-dioxo-3,4-dihydro-1H-2,1-benzothiazinyl), quinolinyl, isoquinolinyl or dibenzothiophenyl (also known as dibenzothienyl); or an N-oxide thereof, or an S-oxide or S-dioxide thereof.

An N-oxide of a compound of formula (I) is, for example, a 1-oxy-[1,4']bipiperidinyl-1'-yl compound.

In another aspect the present-invention provides a compound of formula (I'):

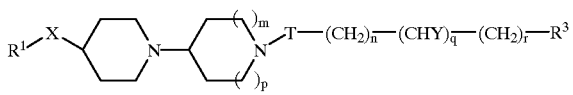

(I')

wherein: q is 0 or 1; n and r are, independently, 0, 1, 2, 3, 4 or 5; m and p are, independently, 0, 1 or 2; X is $CH_2$, CO, O, S, S(O), S(O)$_2$ or $NR^{37}$; provided that when m and p are both 1 then X is not $CH_2$; Y is $NHR^2$ or OH; T is CO, CS, $SO_2$ or $CH_2$; $R^1$ is hydrogen, $C_{1-6}$ alkyl, aryl or heterocyclyl; $R^2$ is hydrogen, $C_{1-6}$ alkyl, aryl ($C_{1-4}$)alkyl or CO($C_{1-6}$ alkyl); $R^3$ is $C_{1-6}$ alkyl {optionally substituted by halogen, $CO_2R^4$ or phthalimide}, $C_{3-7}$ cycloalkyl {optionally substituted by $C_{1-4}$ alkyl or oxo}, $C_{3-7}$ cycloalkenyl {optionally substituted by $C_{1-6}$ alkyl or aryl}, aryl or heterocyclyl; wherein, unless stated otherwise, the foregoing aryl and heterocyclyl moieties are optionally substituted by: halogen, OH, SH, $NO_2$, oxo, $C_{1-6}$ alkyl (itself optionally substituted by halogen, OC(O)$C_{1-6}$ alkyl, phenyl (itself optionally substituted by halo (such as one or two chlorine or fluorine atoms), $C_{1-6}$ alkyl, $SO_2R^{38}$ or $CONR^{39}R^{40}$), naphthyloxy (itself optionally substituted by halo or $C_{2-6}$ alkenyl) or $NR^4C(O)OCH_2$(fluoren-9-yl)), $NR^{41}$(O)OCH$_2$(fluoren-9-yl), $C_{1-6}$ alkoxy (itself optionally substituted by halogen, $CO_2R^4$, $NR^5R^6$ or phenyl (itself optionally substituted by halogen or $NO_2$)), $C_{1-6}$ alkylthio, nitro, $C_{3-7}$ cycloalkyl, $NR^7R^8$, $NR^9COR^{10}$, $CO_2R^{11}$, $CONR^{12}R^{13}$, $COR^{14}$, $SO_dR^{15}$, $SO_2NR^{42}R^{43}$, $NR^{44}SO_2R^{45}$, phenyl (itself optionally substituted by halo, $C_{1-6}$ alkyl, $C_{1-6}$ haloalkyl, CN, $NO_2$ or $C_{1-6}$ alkoxy (itself optionally substituted by halo, OH or pyridinyl)), heterocyclyl (itself optionally substituted by halo, $C_{1-6}$ alkyl, $C_{1-6}$ haloalkyl, CN, $NO_2$, $C_{1-6}$ alkoxy or $C_{1-6}$ haloalkoxy), phenoxy (itself optionally substituted by halo, $C_{1-6}$ alkyl, $C_{1-6}$ haloalkyl, CN, $NO_2$, $C_{1-6}$ alkoxy or $C_{1-6}$ haloalkoxy), SCN, CN, $SO_3H$ (or an alkali metal salt thereof) or methylenedioxy; when aryl is phenyl adjacent substituents may join to form, together with the phenyl ring to which they are attached, a dihydrophenanthrene moiety; d is 0, 1 or 2; $R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); $R^{15}$, $R^{38}$ and $R^{45}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); or a pharmaceutically acceptable salt thereof; or a solvate thereof; provided that: when m and p are both 1, n, q and r are all 0, T and X are both $SO_2$, and $R^1$ is methoxyphenyl then $R^3$ is not propyl; when m, p, q and r are all 1, n is 0, Y is $NH_2$, T is CO and $R^1X$ is $(CH_3)_2N$ then $R^3$ is not 3,5-dibromo-4-aminophenyl, 1-methylindol-3-yl or 1-(tert-butoxycarbonyl)indol-3-yl; and when m and p are both 1, n, q and r are all 0, T is CO, X is NH and $R^1$ is 3-(4-fluorobenzyl)benzimidazol-2-yl then $R^3$ is not 4-fluorophenyl.

In an further aspect the present invention provides a compound of formula (I), wherein: q, s and t are, independently, 0 or 1; n and r are, independently, 0, 1, 2, 3, 4 or 5; m and p are, independently, 0, 1 or 2; X is $CH_2$, C(O), O, S, S(O), S(O)$_2$ or $NR^{37}$; provided that when m and p are both 1 then X is not $CH_2$; Y is $NHR^2$ or OH; T is C(O), C(S), S(O)$_2$ or $CH_2$; $R^1$ is hydrogen, $C_{1-6}$ alkyl, aryl or heterocyclyl; $R^2$ and $R^{47}$ are, independently, hydrogen, $C_{1-6}$ alkyl, aryl($C_{1-4}$)alkyl or CO($C_{1-6}$ alkyl); $R^3$ is $C_{1-6}$ alkyl {optionally substituted by halogen, $CO_2R^4$ or phthalimide}, $C_{3-7}$ cycloalkyl {optionally substituted by $C_{1-4}$ alkyl or oxo}, $C_{3-7}$ cycloalkenyl {optionally substituted by oxo, $C_{1-6}$ alkyl or aryl}, aryl or heterocyclyl; wherein, unless stated otherwise, the foregoing aryl and heterocyclyl moieties are optionally substituted by: halogen, OH, SH, $NO_2$, oxo, $C_{1-6}$ alkyl (itself optionally substituted by halogen, OC(O)$C_{1-6}$ alkyl, $S(O)_2R^{48}$, phenyl (itself optionally substituted by halo (such as one or two chlorine or fluorine atoms), $C_{1-6}$ alkyl, $S(O)_2R^{38}$ or $C(O)NR^{39}R^{40}$), naphthyloxy (itself optionally substituted by halo or $C_{2-6}$ alkenyl), $C_{3-10}$ cycloalkyl (itself optionally substituted by $C_{1-4}$ alkyl or oxo) or $NR^{41}C(O)$ $OCH_2$(fluoren-9-yl)), $NR^{41}C(O)OCH_2$(fluoren-9-yl), $C_{1-6}$ alkoxy (itself optionally substituted by halogen, $C_{1-6}$ alkoxy, $NHCO_2(C_{1-6}$ alkyl), $CO_2R^4$, $NR^5R^6$ or phenyl (itself optionally substituted by halogen or $NO_2$)), $C_{1-6}$ alkylthio, $C_{1-6}$ haloalkylthio, $C_{3-10}$ cycloalkyl, $NR^7R^8$, $NR^9C(O)R^{10}$, $CO_2R^{11}$, $C(O)NR^{12}R^{13}$, $C(O)R^{14}$, $S(O)_dR^{15}$, $S(O)_2$ $NR^{42}R^{43}$, $NR^{44}S(O)_2R^{45}$, phenyl (itself optionally substituted by halo, $C_{1-6}$ alkyl, $C_{1-6}$ haloalkyl, CN, $NO_2$ or $C_{1-6}$ alkoxy (itself optionally substituted by halo, OH or pyridinyl)), heterocyclyl (itself optionally substituted by halo, $C_{1-6}$ alkyl, $C_{1-6}$ haloalkyl, CN, $NO_2$, $C_{1-6}$ alkoxy or $C_{1-6}$ haloalkoxy), phenoxy (itself optionally substituted by halo, $C_{1-6}$ alkyl, $C_{1-6}$ haloalkyl, CN, $NO_2$, $C_{1-6}$ alkoxy or $C_{1-6}$ haloalkoxy), SCN, CN, $SO_3H$ (or an alkali metal salt thereof) or methylenedioxy; when aryl is phenyl adjacent substituents may join to form, together with the phenyl ring to which they are attached, a dihydrophenanthrene moiety; d is 0, 1 or 2; $R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); $R^{15}$, $R^{38}$, $R^{45}$ and $R^{48}$ are, independently, $C_{1-6}$ alkyl (optionally substituted by halogen, hydroxy or $C_{3-10}$ cycloalkyl) or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy; or a pharmaceutically acceptable salt thereof; or a solvate thereof; provided that: when m and p are both 1, n, q and r are all 0, T and X are both S(O)$_2$, and R$^1$ is methoxyphenyl then R$^3$ is not propyl; when m, p, q and r are all 1, n is 0, Y is NH$_2$, T is CO and R$^1$X is (CH$_3$)$_2$N then R$^3$ is not 3,5-dibromo-4-aminophenyl, 1-methylindol-3-yl or 1-(tert-butoxycarbonyl)indol-3-yl; and when m and p are both 1, n, q and r are all 0, T is CO, X is NH and R$^1$ is 3-(4-fluorobenzyl)benzimidazol-2-yl then R$^3$ is not 4-fluorophenyl.

In another aspect the variables m and p are such that m+p is 0, 1 or 2 (for example 1 or 2).

In a further aspect n is 0 or 1.

In a still farther aspect q and r are both 0.

In another aspect n, q and r are all 0.

In another aspect m, p and t are all 1.

In a further aspect s is 0.

In another aspect s is 1. In a further aspect q is 1. In a still further aspect n+r is equal to more than 1 (for example n+r is equal to 2, 3, 4 or 5).

In another aspect t+m+p is not equal to 3 (for example t+m+p is equal to 2).

In a still further aspect X is O.

In another aspect R$^1$ is hydrogen, C$_{1-6}$ alkyl, optionally substituted (as above) aryl or optionally substituted (as above) monocyclic heterocyclyl. In another aspect R$^1$ is phenyl substituted with one or more of fluorine, chlorine, C$_{1-4}$ alkyl (especially methyl) or C$_{1-4}$ alkoxy (especially methoxy).

In yet another aspect R$^1$ is not phenyl substituted by cycloalkyl.

In a further aspect R$^1$ is phenyl optionally substituted (for example with one, two or three) by halo (especially fluoro or chloro), C$_{1-4}$ alkyl (especially methyl) or C$_{1-4}$ alkoxy (especially methoxy). In a still further aspect R$^1$ is phenyl substituted by one, two or three of: fluoro, chloro, methyl or methoxy.

In another aspect R$^1$ is one of the substituted phenyl groups exemplified in Method F below.

In a further aspect T is C(O), S(O)$_2$ or CH$_2$. In a still further aspect T is C(O). In another aspect T is S(O)$_2$ or CH$_2$.

In another aspect R$^3$ is aryl or heterocyclyl either of which is optionally substituted as described above.

In a further aspect R$^3$ is unsubstituted phenyl, mono-substituted phenyl or mono-substituted heterocyclyl, the substituents being chosen from those described above.

In a still further aspect R$^3$ is oxo substituted heterocyclyl, said heterocyclyl optionally further substituted with one or more substituents chosen from those described above.

In another aspect R$^3$ is a bicyclic heterocyclyl optionally substituted as described above. Bicyclic heterocyclyl is an aromatic or non-aromatic 5 or 6 membered ring, fused to one or more other rings, comprising at least one heteroatom selected from the group comprising nitrogen, oxygen and sulphur; or an N-oxide thereof, or an S-oxide or S-dioxide thereof. Bicyclic heterocyclyl is, for example, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo [3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin-4-one-yl) or a benzothiazinyl (for example in 4H-benzo[1,4]thiazin-3-one-yl); or an N-oxide thereof, or an S-oxide or S-dioxide thereof In yet another aspect R$^3$ is: C$_{1-6}$ alkyl {optionally substituted by CO$_2$R$^{16}$ or phthalimide}, C$_{3-7}$ cycloalkyl {optionally substituted by oxo}, phenyl {optionally substituted by: halogen, OH, SH, C$_{1-6}$ alkyl (itself optionally substituted by naphthyloxy (itself optionally substituted by halo or alkenyl) or NR$^{17}$C(O)OCH$_2$(fluoren-9-yl)), C$_{1-6}$ alkoxy (itself optionally substituted by CO$_2$R$^{18}$, NR$^{19}$R$^{20}$ or phenyl (itself optionally substituted by halogen or NO$_2$)), C$_{1-6}$ alkylthio, C$_{1-4}$ haloalkyl, OCF$_3$, nitro, C$_{3-7}$ cycloalkyl, NR$^{21}$R$^{22}$, NR$^{23}$C(O)R$^{24}$, CO$_2$R$^{25}$, C(O)NR$^{26}$R$^{27}$, S(O)$_2$R$^{28}$, phenyl (itself optionally substituted by NO$_2$ or alkoxy (itself optionally substituted by OH or pyridinyl)), phenoxy, SCN, CN, SO$_3$H (or an alkali metal salt thereof) or methylenedioxy, or adjacent substituents may join to form a dihydrophenanthrene moiety}, naphthyl {optionally substituted by NR$^{29}$R$^{30}$ or OH}, heterocyclyl {optionally substituted by halo, NO$_2$, oxo, C$_{1-6}$ alkyl (itself optionally substituted by OC(O)C$_{1-6}$ alkyl, phenyl (itself optionally substituted by halo or alkyl)), alkoxy, CF$_3$, thioalkyl, C(O)R$^{31}$, CO$_2$R$^{32}$, NR$^{33}$C(O)R$^{34}$, phenoxy, phenyl or nitrogen containing heterocyclyl;

R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{29}$, R$^{30}$, R$^{31}$, R$^{32}$, R$^{33}$ and R$^{34}$ are, independently, hydrogen, C$_{1-6}$ alkyl or phenyl;

R$^{28}$ is C$_{1-6}$ alkyl; or a pharmaceutically acceptable salt thereof.

In another aspect R$^3$ is phenyl or heterocyclyl, either of which is optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{46}$ (wherein k is 0, 1 or 2 (preferably 2); and R$^{46}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C$_{1-4}$ haloalkylthio, C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$.

In one aspect the variable R$^3$ can be benzo[1,2,3]thiadiazolyl, thiophenyl or phenyl; the phenyl and thiophenyl rings being optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{46}$ (wherein k is 0, 1 or 2 (preferably 2); and R$^{46}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C$_{1-4}$ haloalkylthio, C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$.

In another aspect the variable R$^3$ can be benzo[1,2,3]thiadiazolyl or phenyl (optionally substituted by: halo, hydroxy, nitro, cyano, amino, C$_{1-4}$ alkyl (itself optionally substituted by S(O)$_2$phenyl), C$_{1-4}$ alkoxy, S(O)$_k$R$^{46}$ (wherein k is 0, 1 or 2; and R$^{46}$ is C$_{1-4}$ alkyl or phenyl) or C$_{1-4}$ haloalkylthio.

In a still further aspect the present invention provides a compound of formula (Ia"):

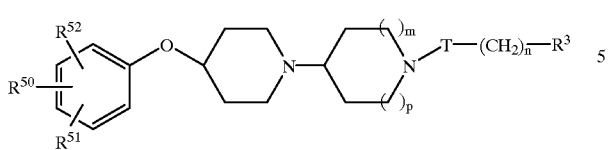

(Ia")

wherein:
T is C(O), C(S), S(O)$_2$ or CH$_2$;
n is 0, 1, 2, 3, 4 or 5;
m and p are, independently, 0, 1 or 2 (but are especially both 1);
R$^{50}$ is hydrogen, cyano, S(O)$_2$(C$_{1-4}$ alkyl), S(O)$_2$(C$_{1-4}$ haloalkyl), halogen, C$_{1-4}$ alkyl, C$_{1-4}$ haloalkyl, C$_{1-4}$ alkoxy or phenyl (optionally substituted by one or two halogen atoms or by one C(O)NR$^{12'}$R$^{13'}$, NR$^{9'}$C(O)R$^{10'}$, S(O)$_2$R$^{15'}$, S(O)$_2$NR$^{42}$R$^{43}$ or NR$^{44}$S(O)$_2$R$^{45}$ group);
R$^{51}$ and R$^{52}$ are, independently, hydrogen, halogen, C$_{1-4}$ alkyl or C$_{1-4}$ alkoxy;
R$^3$ is C$_{1-6}$ alkyl {optionally substituted by halogen, CO$_2$R$^4$ or phthalimide}, C$_{3-7}$ cycloalkyl {optionally substituted by C$_{1-4}$ alkyl or oxo}, aryl or heterocyclyl;
wherein, unless stated otherwise, the foregoing aryl and heterocyclyl moieties are optionally substituted by: halogen, OH, SH, NO$_2$, oxo, C$_{1-6}$ alkyl (itself optionally substituted by halogen, OC(O)C$_{1-6}$ alkyl, phenyl (itself optionally substituted by halo or C$_{1-6}$ alkyl), naphthyloxy (itself optionally substituted by halo or C$_{2-6}$ alkenyl) or NR$^4$C(O)OCH$_2$(fluoren-9-yl)), C$_{1-6}$ alkoxy (itself optionally substituted by halogen, CO$_2$R$^4$, NR$^5$R$^6$ or phenyl (itself optionally substituted by halogen or NO$_2$)), C$_{1-6}$ alkylthio, nitro, C$_{3-7}$ cycloalkyl, NR$^7$R$^8$, NR$^9$C(O)R$^{10}$, CO$_2$R$^{11}$, C(O)NR$^{12}$R$^{13}$, C(O)R$^{14}$, S(O)$_2$R$^{15}$, phenyl (itself optionally substituted by NO$_2$ or C$_{1-6}$ alkoxy (itself optionally substituted by OH or pyridinyl)), phenoxy, SCN, CN, SO$_3$H (or an alkali metal salt thereof) or methylenedioxy; when aryl is phenyl adjacent substituents may join to form, together with the phenyl ring a dihydrophenanthrene moiety;
R$^4$, R$^5$, R$^6$, R$^7$, R$^8$, R$^9$, R$^{9'}$, R$^{10}$, R$^{10'}$, R$^{11}$, R$^{12}$, R$^{12'}$, R$^{13}$, R$^{13'}$, R$^{14}$, R$^{42}$, R$^{43}$ and R$^{44}$ are, independently, hydrogen, C$_{1-6}$ alkyl or phenyl;
R$^{15}$, R$^{15'}$ and R$^{45}$ are, independently, C$_{1-6}$ alkyl or phenyl;
or a pharmaceutically acceptable salt thereof.

In a further aspect R$^{50}$, R$^{51}$ and R$^{52}$ are, independently, hydrogen, halogen, (especially fluoro or chloro), C$_{1-4}$ alkyl (especially methyl) or C$_{1-4}$ alkoxy (especially methoxy).

In a still further aspect the present invention provides a compound of formula (Ia):

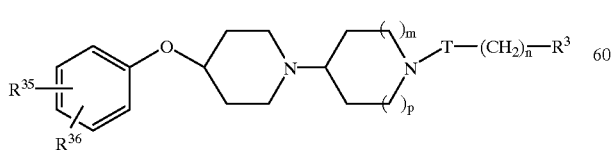

(Ia)

wherein:
T is C(O), C(S), S(O)$_2$ or CH$_2$;
n is 0, 1, 2, 3, 4 or 5;
m and p are, independently, 0, 1 or 2 (but are especially both 1);
R$^{35}$ is hydrogen, cyano, S(O)$_2$(C$_{1-4}$ alkyl), S(O)$_2$(C$_{1-4}$ haloalkyl), halogen, C$_{1-4}$ alkyl, C$_{1-4}$ haloalkyl, C$_{1-4}$ alkoxy or phenyl (optionally substituted by one or two halogen atoms or by one C(O)NR$^{12'}$R$^{13'}$, NR$^{9'}$C(O)R$^{10'}$, S(O)$_2$R$^{15'}$, S(O)$_2$NR$^{42}$R$^{43}$ or NR$^{44}$S(O)$_2$R$^{45}$ group);
R$^{36}$ is hydrogen, halogen or C$_{1-4}$ alkyl;
R$^3$ is C$_{1-6}$ alkyl {optionally substituted by halogen, CO$_2$R$^4$ or phthalimide}, C$_{3-7}$ cycloalkyl {optionally substituted by C$_{1-4}$ alkyl or oxo}, aryl or heterocyclyl;
wherein, unless stated otherwise, the foregoing aryl and heterocyclyl moieties are optionally substituted by: halogen, OH, SH, NO$_2$, oxo, C$_{1-6}$ alkyl (itself optionally substituted by halogen, OC(O)C$_{1-6}$ alkyl, phenyl (itself optionally substituted by halo or C$_{1-6}$ alkyl), naphthyloxy (itself optionally substituted by halo or C$_{2-6}$ alkenyl) or NR$^4$C(O)OCH$_2$(fluoren-9-yl)), C$_{1-6}$ alkoxy (itself optionally substituted by halogen, CO$_2$R$^4$, NR$^5$R$^6$ or phenyl (itself optionally substituted by halogen or NO$_2$)), C$_{1-6}$ alkylthio, nitro, C$_{3-7}$ cycloalkyl, NR$^7$R$^8$, NR$^9$C(O)R$^{10}$, CO$_2$R$^{11}$, C(O)NR$^{12}$R$^{13}$, C(O)R$^{14}$, S(O)$_2$R$^{15}$, phenyl (itself optionally substituted by NO$_2$ or C$_{1-6}$ alkoxy (itself optionally substituted by OH or pyridinyl)), phenoxy, SCN, CN, SO$_3$H (or an alkali metal salt thereof) or methylenedioxy; when aryl is phenyl adjacent substituents may join to form, together with the phenyl ring a dihydrophenanthrene moiety;
R$^4$, R$^5$, R$^6$, R$^7$, R$^8$, R$^9$, R$^{9'}$, R$^{10}$, R$^{10'}$, R$^{11}$, R$^{12}$, R$^{12'}$, R$^{13}$, R$^{13'}$, R$^{14}$, R$^{42}$, R$^{43}$ and R$^{44}$ are, independently, hydrogen, C$_{1-6}$ alkyl or phenyl;
R$^{15}$, R$^{15'}$ and R$^{45}$ are, independently, C$_{1-6}$ alkyl or phenyl;
or a pharmaceutically acceptable salt thereof.

In another aspect the present invention provides a compound of formula (Ia'):

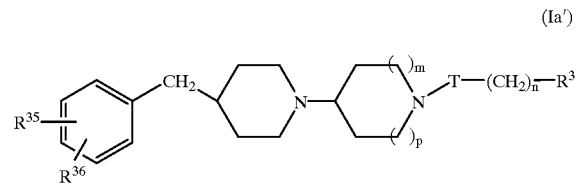

(Ia')

wherein:
T is CO, CS, SO$_2$ or CH$_2$;
n is 0, 1, 2, 3, 4 or 5;
m and p are, independently, 0, 1 or 2 (but are especially both 1);
R$^{35}$ is hydrogen, cyano, SO$_2$(C$_{1-4}$ alkyl), SO$_2$(C$_{1-4}$ haloalkyl), halogen, C$_{1-4}$ alkyl, C$_{1-4}$ haloalkyl, C$_{1-4}$ alkoxy or phenyl (optionally substituted by one or two halogen atoms or by one CONR$^{12'}$R$^{13'}$, NR$^{9'}$COR$^{10'}$, SO$_2$R$^{15'}$, SO$_2$NR$^{42}$R$^{43}$ or NR$^{44}$SO$_2$R$^{45}$ group);
R$^{36}$ is hydrogen, halogen or C$_{1-4}$ alkyl;
R$^3$ is C$_{1-6}$ alkyl {optionally substituted by halogen, CO$_2$R$^4$ or phthalimide}, C$_{3-7}$ cycloalkyl {optionally substituted by C$_{1-4}$ alkyl or oxo}, aryl or heterocyclyl;
wherein, unless stated otherwise, the foregoing aryl and heterocyclyl moieties are optionally substituted by: halogen, OH, SH, NO$_2$, oxo, C$_{1-6}$ alkyl (itself optionally substituted by halogen, OC(O)C$_{1-6}$ alkyl, phenyl (itself optionally substituted by halo or C$_{1-6}$ alkyl), naphthyloxy (itself optionally substituted by halo or C$_{2-6}$ alkenyl) or NR$^4$C(O)OCH$_2$(fluoren-9-yl)), C$_{1-6}$ alkoxy (itself optionally substituted by halogen, CO$_2$R$^4$, NR$^5$R$^6$ or phenyl (itself optionally substituted by halogen or NO$_2$)), C$_{1-6}$ alkylthio, nitro, C$_{3-7}$ cycloalkyl, NR$^7$R$^8$, NR$^9$COR$^{10}$, CO$_2$R$^{11}$, CONR$^{12}$R$^{13}$, COR$^{14}$, SO$_2$R$^{15}$, phenyl (itself optionally substituted by NO$_2$ or C$_{1-6}$ alkoxy (itself optionally substituted by OH or pyridinyl)), phenoxy, SCN, CN, SO$_3$H (or an alkali metal salt thereof) or methylenedioxy; when aryl is phenyl adjacent substituents may join to form, together with the phenyl ring a dihydrophenanthrene moiety;

R$^4$, R$^5$, R$^6$, R$^7$, R$^8$, R$^9$, R$^{9'}$, R$^{10}$, R$^{10'}$, R$^{11}$, R$^{12}$, R$^{12'}$, R$^{13}$, R$^{13'}$, R$^{14}$, R$^{42}$, R$^{43}$ and R$^{44}$ are, independently, hydrogen, C$_{1-6}$ alkyl or phenyl; R$^{15}$, R$^{15'}$ and R$^{45}$ are, independently, C$_{1-6}$ alkyl or phenyl;

or a pharmaceutically acceptable salt thereof.

In a further aspect R$^3$ is heterocyclyl (such as thienyl, isoxazolyl or indolyl, or a naphthyridinyl, an imidazopyridinyl or an isoquinolinyl) optionally substituted by oxo, halogen or C$_{1-6}$ alkyl.

In yet another aspect the present invention provides a compound of formula (Ia) wherein:

T is C(O), C(S), S(O)$_2$ or CH$_2$;
n is 0, 1, 2, 3, 4 or 5;
m and p are, independently, 0, 1 or 2;
R$^{35}$ is hydrogen, halogen or phenyl (optionally substituted by one or two halogen atoms or by one C(O)NR$^{12'}$R$^{13'}$, NR$^{9'}$C(O)R$^{10'}$, S(O)$_2$R$^{15'}$, S(O)$_2$NR$^{42}$R$^{43}$ or NR$^{44}$S(O)$_2$R$^{45}$ group);
R$^{36}$ is hydrogen or halogen;
R$^3$ is C$_{1-6}$ alkyl {optionally substituted by halogen, CO$_2$R$^4$ or phthalimide}, C$_{3-7}$ cycloalkyl {optionally substituted by C$_{1-4}$ alkyl or oxo}, aryl or heterocyclyl;

wherein, unless stated otherwise, the foregoing aryl and heterocyclyl moieties are optionally substituted by: halogen, OH, SH, NO$_2$, oxo, C$_{1-6}$ alkyl (itself optionally substituted by halogen, OC(O)C$_{1-6}$ alkyl, phenyl (itself optionally substituted by halo or C$_{1-6}$ alkyl), naphthyloxy (itself optionally substituted by halo or C$_{2-6}$ alkenyl) or NR$^4$C(O)OCH$_2$(fluoren-9-yl)), C$_{1-6}$ alkoxy (itself optionally substituted by halogen, CO$_2$R$^4$, NR$^5$R$^6$ or phenyl (itself optionally substituted by halogen or NO$_2$)), C$_{1-6}$ alkylthio, nitro, C$_{3-7}$ cycloalkyl, NR$^7$R$^8$, NR$^9$C(O)R$^{10}$, CO$_2$R$^{11}$, C(O)NR$^{12}$R$^{13}$, C(O)R$^{14}$, S(O)$_2$R$^{15}$, phenyl (itself optionally substituted by NO$_2$ or C$_{1-6}$ alkoxy (itself optionally substituted by OH or pyridinyl)), phenoxy, SCN, CN, SO$_3$H (or an alkali metal salt thereof) or methylenedioxy; when aryl is phenyl adjacent substituents may join to form, together with the phenyl ring a dihydrophenanthrene moiety;

R$^4$, R$^5$, R$^6$, R$^7$, R$^8$, R$^9$, R$^{9'}$, R$^{10}$, R$^{10'}$, R$^{11}$, R$^{12}$, R$^{12'}$, R$^{13}$, R$^{13'}$, R$^{14}$, R$^{42}$, R$^{43}$ and R$^{44}$ are, independently, hydrogen, C$_{1-6}$ alkyl or aryl;

R$^{15}$, R$^{15'}$ and R$^{45}$ are, independently, C$_{1-6}$ alkyl or aryl;

or a pharmaceutically acceptable salt thereof.

In a further aspect R$^{35}$ and R$^{36}$ are, independently, hydrogen, halogen, (especially fluoro or chloro), C$_{1-4}$ alkyl (especially methyl) or C$_{1-4}$ alkoxy (especially methoxy). In another aspect R$^{35}$ and R$^{36}$ are both chlorine or both fluorine, especially 3,4 disposed on the phenyl ring to which they are attached.

In a further aspect the present invention provides a compound of formula (Ib):

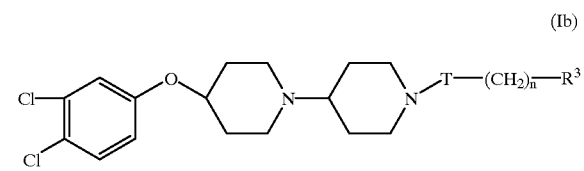

(Ib)

wherein T, n and R$^3$ are as defined above.

In a still further aspect the present invention provides a compound of formula (Ic):

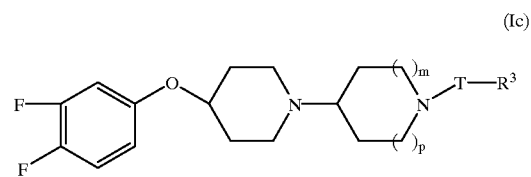

(Ic)

wherein T, m, p and R$^3$ are as defined above.

In another aspect the present invention provides a compound of formula (Id):

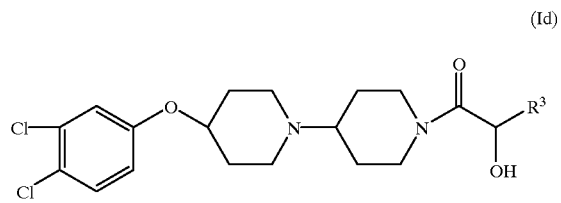

(Id)

wherein R$^3$ is as defined above.

In yet another aspect the present invention provides a compound of formula (Ie):

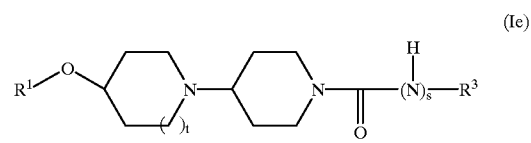

(Ie)

wherein R$^1$, t, s and R$^3$ are as defined above.

In a further aspect the present invention provides a compound of formula (If):

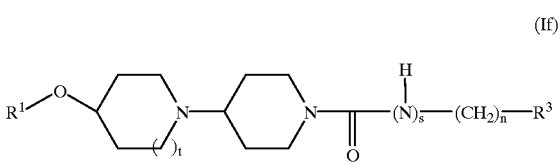

(If)

wherein R$^1$, n, t, s and R$^3$ are as defined above.

In a still further aspect the present invention provides a compound of formula (Ig):

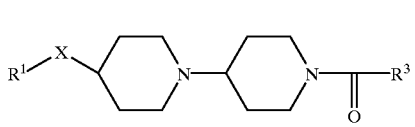
(Ig)

wherein $R^1$, X and $R^3$ are as defined above.

A compound of formula (I), wherein s is 0, can be prepared by coupling a compound of formula (II):

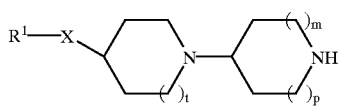
(II)

with a compound of formula (III):

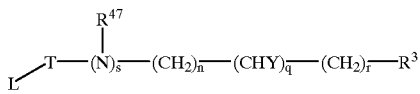
(III)

wherein L is a suitable leaving group, and the variables Y and T are optionally protected during the course of the reaction by standard protecting groups known in the art and deprotected in a separate step or during the reaction work-up. For example:

when T is carbonyl, L can be OH and the coupling can be carried out in the presence of a coupling agent (such as bromo-tris-pyrrolidino-phosphonium hexafluorophosphate, (known as PYBROP™), oxalyl chloride, thionyl chloride or N,N'-carbonyl diimidazole, or another coupling agent known to a person skilled in the art); or, when T is sulphonyl, L can be chloro and the coupling can be carrier out in the presence of a suitable base (such as potassium carbonate) in a suitable solvent (such as acetone).

A compound of formula (I), wherein s is 1, $R^{47}$ is hydrogen and T is CO, can be prepared by reacting a compound of formula (II), wherein m and p are both 1, with an aromatic isocyanate of formula with an isocyanate $O=C=N-(CH_2)_n-(CH_2)_r-R^3$.

A compound of formula (II) can be prepared by deprotecting a compound of formula (IV):

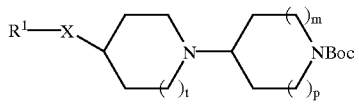
(IV)

for example using trifluoroacetic acid in a suitable solvent (such as dichloromethane) or using a source of hydrogen chloride in a suitable solvent (such as dioxane).

A compound of formula (IV), wherein X is O, can be prepared by reacting a compound of formula (V):

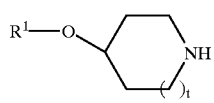
(V)

with a compound of formula (VI):

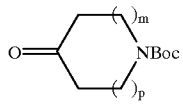
(VI)

in the presence of $NaBH(OAc)_3$ and acetic acid.

A compound of formula (IV), wherein X is CO or $CH_2$, can be prepared by oxidising or reducing a compound of formula (VII):

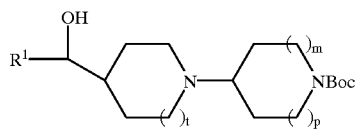
(VII)

A compound of formula (VII) can be prepared by reacting a compound of formula (VIII):

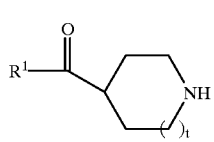
(VIII)

with a compound of formula (VI) in the presence of $NaBH(OAc)_3$ and acetic acid. A compound of formula (VIII) can be prepared by reduction of a compound of formula (IX):

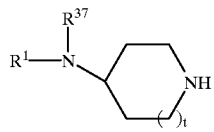
(IX)

A compound of formula (I) wherein X is $NR^{37}$ can be prepared by reacting a compound of formula (X):

(X)

with a compound of formula (XI):

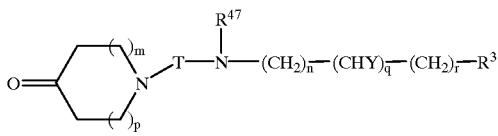
(XI)

in the presence of NaBH(OAc)$_3$ and acetic acid. A compound of formula (X) can be prepared by reacting NHR$^1$R$^{37}$ with a compound of formula (XII):

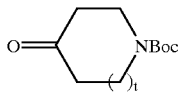
(XII)

in the presence of NaBH(OAc)$_3$ and acetic acid and then deprotecting the piperidine nitrogen {for example using trifluoroacetic acid in a suitable solvent (such as dichloromethane) or using a source of hydrogen chloride in a suitable solvent (such as dioxane)}.

Alternatively, a compound of formula (I), wherein s, n, q and r are all 0 and T is CO, can be prepared by reacting a compound of formula (XIII):

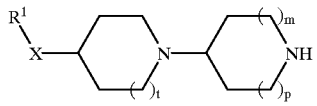
(XIII)

with an acid: R$^3$CO$_2$H. A compound of formula (XIII) can be prepared by deprotecting a compound of formula (XIV):

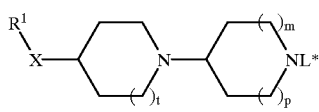
(XIV)

wherein L* is BOC or a benzyl group. A compound of formula (XIV) can be prepared by performing a fluoride displacement reaction on FR$^1$ in the presence of compound of formula (XV):

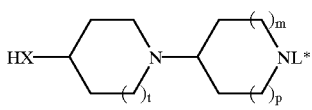
(XV)

A compound of formula (XV) can be prepared by coupling a compound of formula (XVI) with a compound of formula (XVII):

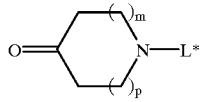
(XVI)

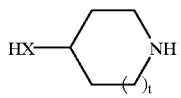
(XVII)

Alternatively, a compound of formula (I) wherein s, n, q and r are all 0 and T is CO, can be prepared by performing a fluoride displacement reaction on FR$^1$ in the presence of compound of formula (XVIII):

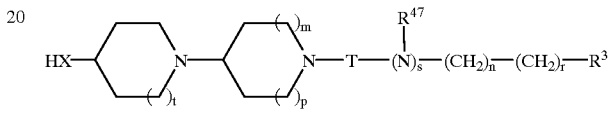
(XVIII)

provided that R$^{47}$ is not hydrogen.

A compound of formula (XVIII) can be prepared by reacting a compound of formula (XIX):

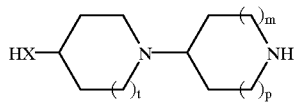
(XIX)

with an appropriate mixed anhydride (such as an anhydride of formula R$^3$C(O)OC(O)(C$_{1-6}$ alkyl), wherein alkyl is, for example, methyl, ethyl or iso-butyl). A compound of formula (XIX) can be prepared by deprotecting a compound of formula (XV).

Alternatively, a compound of formula (I) can be prepared by reductive ammination of a compound of formula (XX):

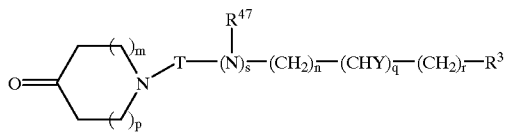
(XX)

with an amine of formula (XXI):

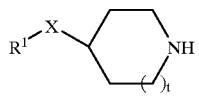
(XXI)

under suitable conditions.

Further compounds of formula (I) can be prepared by adaptation of: the routes described above, methods described in the art or the Examples recited below.

Compounds of formula (V), (VI), (IX), (XI), (XII), (XVI) and (XVII) can be prepared by using or adapting methods described in the art.

In another aspect the present invention provides processes for the preparation of compounds of formula (I) (as defined above), (I'), (Ia"), (Ia), (Ia'), (Ib), (Ic), (Id), (Ie), (If) and (Ig).

The intermediates of formula (II), (IV), (XIII), (XIV) and (XVII) defined herein are novel and these, and processes for their preparation, are provided as further features of the invention.

Examples of compounds of formula (Ib) are listed in Table I below.

TABLE I

| Compound | T | n | $R^3$ | M + H |
|---|---|---|---|---|
| 1 | C(O) | 0 | $C_6H_5$ | 433 |
| 2 | C(O) | 0 | 3,4-$Cl_2$—$C_6H_3$ | 501 |
| 3 | C(O) | 0 | 2,4-$Cl_2$—$C_6H_3$ | 501 |
| 4 | C(O) | 0 | 4-$CH_3$—$C_6H_4$ | 447 |
| 5 | C(O) | 0 | 4-$CH_3O$—$C_6H_4$ | 463 |
| 6 | C(O) | 0 | 4-$CF_3$—$C_6H_4$ | 501 |
| 7 | C(O) | 0 | 4-Cl—$C_6H_4$ | 467 |
| 8 | C(O) | 0 | 4-$NO_2$—$C_6H_4$ | 478 |
| 9 | C(O) | 0 | 3,5-$Cl_2$—$C_6H_3$ | 501 |
| 10 | C(O) | 0 | 2-F—$C_6H_4$ | 451 |
| 11 | C(O) | 0 | 4-cyclohexyl-$C_6H_4$ | 515 |
| 12 | C(O) | 0 | 4-(n-butoxy)-$C_6H_4$ | 505 |
| 13 | C(O) | 0 | 3-$NMe_2$—$C_6H_4$ | 476 |
| 14 | C(O) | 0 | 4-(NHC(O)Me)—$C_6H_4$ | 490 |
| 15 | C(O) | 0 | 4-$NEt_2$—$C_6H_4$ | 504 |
| 16 | C(O) | 0 | 3-$CO_2Me$—$C_6H_4$ | 491 |
| 17 | C(O) | 0 | 2-C(O)$NH_2$—$C_6H_4$ | |
| 18 | C(O) | 0 | 4-S(O)$_2$Me—$C_6H_4$ | 511 |
| 19 | C(O) | 0 | 2-I—$C_6H_4$ | 559 |
| 20 | C(O) | 0 | 3-phenoxy-$C_6H_4$ | 525 |
| 21 | C(O) | 0 | 2-Me—$C_6H_4$ | 447 |
| 22 | C(O) | 0 | 3-Me—$C_6H_4$ | 447 |
| 23 | C(O) | 0 | 3-I—$C_6H_4$ | 559 |
| 24 | C(O) | 0 | 3-$NH_2$-6-(NH$C_6H_5$)—$C_6H_3$ | 539 |
| 25 | C(O) | 0 | 3,5-$F_2$—$C_6H_3$ | 469 |
| 26 | C(O) | 0 | 3-$NO_2$-4-(tert-Bu)—$C_6H_3$ | 534 |
| 27 | C(O) | 0 | 3-$NO_2$-5-($CO_2Me$)—$C_6H_3$ | 536 |
| 28 | C(O) | 0 | 2-Me-5-$NO_2$—$C_6H_3$ | 492 |
| 29 | C(O) | 0 | 3,5-(tert-Bu)$_2$—$C_6H_3$ | 545 |
| 30 | C(O) | 0 | 2-$NO_2$-5-Me—$C_6H_3$ | 492 |
| 31 | C(O) | 0 | 2-Br-5-MeO—$C_6H_3$ | 541 |
| 32 | C(O) | 0 | 3-MeO-4-($CO_2Me$)—$C_6H_3$ | |
| 33 | C(O) | 0 | 2-(NHC(O)Me)-5-Br—$C_6H_3$ | 568 |
| 34 | C(O) | 0 | 2-$NO_2$-5-SCN—$C_6H_3$ | 535 |
| 35 | C(O) | 0 | 3-MeO-4-Me-$C_6H_3$ | 477 |
| 36 | C(O) | 0 | 4-CN—$C_6H_4$ | 458 |
| 37 | C(O) | 0 | 3-CN—$C_6H_4$ | 458 |
| 38 | C(O) | 0 | 2-phenoxy-4-Br—$C_6H_3$ | |
| 39 | C(O) | 0 | 2-$NH_2$-5-I—$C_6H_3$ | 574 |
| 40 | C(O) | 0 | 4-F-$C_6H_4$ | 451 |
| 41 | S(O)$_2$ | 0 | 2-$CF_3O$—$C_6H_4$ | 553 |
| 42 | S(O)$_2$ | 0 | 3-$NO_2$-4-Cl—$C_6H_3$ | 548 |
| 43 | S(O)$_2$ | 0 | Camphor-10-yl(alternatively named 7,7-dimethyl-bicyclo[2.2.1]heptan-2-on-1-yl) | 543 |
| 44 | S(O)$_2$ | 0 | n-Pr | 435 |
| 45 | S(O)$_2$ | 0 | $C_6Me_5$ | 539 |
| 46 | S(O)$_2$ | 0 | 4-(n-Pr)—$C_6H_4$ | 511 |
| 47 | S(O)$_2$ | 0 | Naphth-2-yl | 519 |
| 48 | S(O)$_2$ | 0 | 2,6-$Cl_2$—$C_6H_3$ | 537 |
| 49 | S(O)$_2$ | 0 | 2,6-$F_2$—$C_6H_3$ | 505 |
| 50 | S(O)$_2$ | 0 | 4-$NO_2$—$C_6H_4$ | 514 |
| 51 | S(O)$_2$ | 0 | 3,4-$Cl_2$—$C_6H_3$ | 537 |
| 52 | S(O)$_2$ | 0 | 2,5-$Cl_2$—$C_6H_3$ | |
| 53 | S(O)$_2$ | 0 | 5-($NMe_2$)-naphth-1-yl | 562 |
| 54 | S(O)$_2$ | 0 | 2,1,3-benzthiadiazol-4-yl | 527 |
| 55 | S(O)$_2$ | 0 | 4-Et—$C_6H_4$ | 497 |
| 56 | S(O)$_2$ | 0 | 2,5-$Cl_2$-thien-3-yl | 543 |
| 57 | S(O)$_2$ | 0 | 3,4-(MeO)$_2$—$C_6H_3$ | 529 |
| 58 | S(O)$_2$ | 0 | 3-$CF_3$-6-Cl—$C_6H_3$ | 571 |
| 59 | S(O)$_2$ | 0 | 5-Cl-thien-2-yl | 509 |
| 60 | S(O)$_2$ | 0 | 4-Cl—$C_6H_4$ | 503 |
| 61 | S(O)$_2$ | 0 | 4-(iso-Pr)—$C_6H_4$ | 511 |
| 62 | S(O)$_2$ | 0 | 2-Cl-4-$CF_3$—$C_6H_3$ | 571 |
| 63 | S(O)$_2$ | 0 | Benzofuraz-4-yl(other name 2,1,3-benzoxadiazol-4-yl) | 511 |
| 64 | S(O)$_2$ | 0 | 3-Me-$C_6H_4$ | 483 |
| 65 | S(O)$_2$ | 0 | 2,4-$F_2$-$C_6H_3$ | 505 |

TABLE I-continued

| Compound | T | n | R³ | M + H |
|---|---|---|---|---|
| 66 | S(O)₂ | 0 | 2-Me-5-F—C₆H₃ | 501 |
| 67 | S(O)₂ | 0 | 4-CF₃O—C₆H₄ | 553 |
| 68 | S(O)₂ | 0 | iso-Pr | 435 |
| 70 | S(O)₂ | 0 | 4-(CO₂H)—C₆H₄ | 513 |
| 71 | S(O)₂ | 0 | chromen-2-one-6-yl | 537 |
| 72 | S(O)₂ | 0 | 3,5-Cl₂—C₆H₃ | 537 |
| 73 | S(O)₂ | 0 | 2,3-Cl₂—C₆H₃ | 537 |
| 74 | S(O)₂ | 1 | 4-NO₂—C₆H₄ | |
| 75 | S(O)₂ | 0 | 3-CF₃—C₆H₄ | 537 |
| 76 | S(O)₂ | 0 | 4-(tert-Bu)—C₆H₄ | 525 |
| 77 | S(O)₂ | 0 | 3-CO₂H-4-OH—C₆H₃ | 529 |
| 78 | S(O)₂ | 0 | 2-NO₂—C₆H₄ | 514 |
| 79 | S(O)₂ | 0 | 2-F—C₆H₄ | 487 |
| 80 | S(O)₂ | 0 | 3-NO₂—C₆H₄ | 514 |
| 83 | S(O)₂ | 0 | Naphth-1-yl | 519 |
| 84 | S(O)₂ | 0 | 2-MeO-5-Cl—C₆H₃ | 533 |
| 85 | S(O)₂ | 0 | 3-F—C₆H₄ | 487 |
| 86 | S(O)₂ | 0 | 3-Cl-4-(NHC(O)Me)—C₆H₃ | 560 |
| 87 | S(O)₂ | 1 | C₆H₅ | 483 |
| 88 | S(O)₂ | 0 | 2-NO₂-4-MeO—C₆H₃ | 544 |
| 89 | S(O)₂ | 0 | 2-Me-5-NO₂—C₆H₃ | 528 |
| 90 | S(O)₂ | 0 | 3-CO₂H—C₆H₄ | 513 |
| 91 | S(O)₂ | 0 | 2,4,6-Me₃—C₆H₂ | 511 |
| 92 | S(O)₂ | 0 | Me | |
| 93 | S(O)₂ | 0 | 3,4-Cl₂—C₆H₃ | 537 |
| 94 | S(O)₂ | 0 | 4-MeO—C₆H₄ | |
| 95 | S(O)₂ | 0 | 4-NHC(O)Me—C₆H₄ | 526 |
| 96 | S(O)₂ | 0 | 2-CF₃—C₆H₄ | 537 |
| 97 | S(O)₂ | 0 | (CH₂)₂CO₂Me | 479 |
| 98 | S(O)₂ | 0 | 4-Me—C₆H₄ | 483 |
| 99 | S(O)₂ | 0 | 4-CF₃—C₆H₄ | 537 |
| 100 | S(O)₂ | 0 | 4-CN—C₆H₄ | 494 |
| 101 | S(O)₂ | 0 | 3-NO₂-4-Me—C₆H₃ | 528 |
| 102 | S(O)₂ | 0 | 1H-2-oxo-quinolin-6-yl | |
| 103 | S(O)₂ | 0 | 2-(NHCOMe)-4-methylthiazol-5-yl | 547 |
| 104 | S(O)₂ | 0 | Thien-2-yl | 475 |
| 105 | S(O)₂ | 0 | Quinolin-8-yl | |
| 106 | S(O)₂ | 0 | 2-OH-3,5-Cl₂—C₆H₂ | 553 |
| 107 | S(O)₂ | 0 | 2-(CO₂Me)—C₆H₄ | 527 |
| 108 | S(O)₂ | 0 | 2,5-(MeO)₂—C₆H₃ | 529 |
| 109 | S(O)₂ | 0 | phenyl | 469 |
| 110 | S(O)₂ | 0 | 2-Me-4-NO₂—C₆H₃ | 528 |
| 111 | S(O)₂ | 0 | 5-(pyridin-2-yl)thien-2-yl | 552 |
| 112 | S(O)₂ | 0 | 1,3-Me₂-5-Cl-pyrazol-4-yl | 521 |
| 113 | S(O)₂ | 0 | 3,5-Me₂-isoxazol-4-yl | 488 |
| 114 | S(O)₂ | 0 | 2,3,6-Me₃-4-MeO—C₆H | 541 |
| 115 | S(O)₂ | 0 | 1-Me-imidazol-4-yl | 473 |
| 116 | S(O)₂ | 0 | 2-MeO-5-Me-C₆H₃ | 513 |
| 117 | S(O)₂ | 0 | 5-(isoxazol-3-yl)thien-2-yl | 542 |
| 118 | S(O)₂ | 0 | 2-(CO₂Me)thien-3-yl | 533 |
| 119 | S(O)₂ | 0 | 4-(1,1-dimethylprop-1-yl)-C₆H₄ | 539 |
| 120 | S(O)₂ | 0 | 1-(N-phthalimido)-ethyl | 566 |
| 121 | CH₂ | 0 | 4-Me—C₆H₄ | 433 |
| 122 | CH₂ | 0 | 4-(CO₂H)—C₆H₄ | 463 |
| 123 | CH₂ | 0 | 2-(CO₂H)—C₆H₄ | 463 |
| 124 | CH₂ | 0 | 4-(NHC(O)Me)—C₆H₄ | 476 |
| 125 | CH₂ | 0 | 3-OH—C₆H₄ | 435 |
| 126 | CH₂ | 0 | 4-MeO—C₆H₄ | 449 |
| 127 | CH₂ | 0 | 5-Me-fur-2-yl | 423 |
| 128 | CH₂ | 0 | 2,5-F₂—C₆H₃ | 455 |
| 129 | CH₂ | 0 | 5-NO₂-fur-2-yl | |
| 130 | CH₂ | 0 | 4-NO₂—C₆H₄ | |
| 131 | CH₂ | 0 | 4-iso-Pr-C₆H₄ | 461 |
| 132 | CH₂ | 0 | phenyl | 419 |
| 133 | CH₂ | 0 | 2-(SO₃⁻Na⁺)—C₆H₄ | 498 |
| 134 | CH₂ | 0 | 4-F—C₆H₄ | 437 |
| 135 | CH₂ | 0 | 2,6-Cl₂—C₆H₃ | 487 |
| 136 | CH₂ | 0 | 3,4-Cl₂—C₆H₃ | 487 |
| 137 | CH₂ | 0 | 2,4-Cl₂—C₆H₃ | |
| 138 | CH₂ | 0 | 4-(OCH₂CO₂H)—C₆H₄ | 493 |
| 139 | CH₂ | 0 | Pyrid-2-yl | 420 |
| 140 | CH₂ | 0 | 3-methylthien-2-yl | 439 |
| 141 | CH₂ | 0 | 3-Cl—C₆H₄ | 453 |
| 142 | CH₂ | 0 | 5-methylthien-2-yl | 439 |
| 143 | CH₂ | 0 | 3-OH-4-MeO—C₆H₃ | 465 |
| 144 | CH₂ | 0 | 3-NO₂-4-OH—C₆H₃ | 480 |
| 145 | CH₂ | 0 | Chromon-3-yl | |

TABLE I-continued

| Compound | T | n | R³ | M + H |
|---|---|---|---|---|
| 146 | CH₂ | 0 | 1,3-Me₂-5-Cl-pyrazol-4-yl | 471 |
| 147 | CH₂ | 0 | 3,4-F₂—C₆H₃ | 455 |
| 148 | CH₂ | 0 | 4-Cl-pyrazol-3-yl | 443 |
| 149 | C(O) | 1 | 4-S(O)₂Me—C₆H₄ | |
| 150 | CH₂ | 0 | 2,6-Cl₂-pyridin-4-yl | |
| 151 | CH₂ | 0 | 5-(4-NO₂—C₆H₄)-fur-2-yl | 530 |
| 152 | CH₂ | 0 | 1-(4-methylbenzyl)-pyrazol-5-yl | |
| 153 | CH₂ | 0 | Benzfur-2-yl | 459 |
| 154 | CH₂ | 0 | 2-phenylimidazol-4-yl | 485 |
| 155 | CH₂ | 0 | 5-ethylthien-2-yl | 453 |
| 156 | CH₂ | 0 | 2-Cl-quinolin-3-yl | 504 |
| 157 | CH₂ | 0 | 6-methylpyridin-2-yl | 434 |
| 158 | CH₂ | 0 | 1-acetylindol-3-yl | 500 |
| 159 | CH₂ | 0 | 6-formyl-pyridin-2-yl | 448 |
| 160 | CH₂ | 0 | Quinolin-3-yl | |
| 161 | CH₂ | 0 | 5-(CH₂OC(O)CH₃)-fur-2-yl | |
| 162 | CH₂ | 0 | 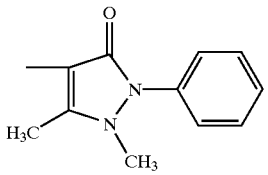 | 529 |
| 163 | CH₂ | 0 | Pyridin-4-yl | 420 |
| 164 | CH₂ | 0 | 3-OH-4-NO₂—C₆H₃ | 480 |
| 165 | CH₂ | 0 | 3,5-F₂—C₆H₃ | 455 |
| 166 | CH₂ | 0 | 3-CF₃—C₆H₃ | 487 |
| 167 | CH₂ | 0 | 2-F-6-Cl—C₆H₃ | 471 |
| 168 | CH₂ | 0 | 2-(tert-butyl)S—C₆H₄ | |
| 169 | CH₂ | 0 | 4-Et-C₆H₄ | 447 |
| 170 | CH₂ | 0 | 3-CO₂H-4-OH—C₆H₄ | 479 |
| 171 | CH₂ | 0 | 3-(OCH₂CO₂H)—C₆H₄ | 493 |
| 172 | CH₂ | 0 | 2,3-methylenedioxyphenyl | 463 |
| 173 | CH₂ | 0 | Thiazol-2-yl | 426 |
| 174 | CH₂ | 0 | 5-ethylfur-2-yl | 437 |
| 175 | CH₂ | 0 | Quinolin-2-yl | 470 |
| 176 | CH₂ | 0 | Quinolin-4-yl | 470 |
| 177 | CH₂ | 0 | 4-CH₂CH(CH₃)₂—C₆H₄ | 475 |
| 178 | CH₂ | 0 | 3-MeO-4-OH-5-CO₂H—C₆H₂ | 509 |
| 179 | CH₂ | 0 | 4-bromopyrazol-3-yl | |
| 180 | CH₂ | 0 | 2-(OCH₂CO₂H)-3-MeO—C₆H₃ | 523 |
| 181 | CH₂ | 0 | 4-(O(CH₂)₃N(CH₃)₂)—C₆H₄ | 520 |
| 182 | CH₂ | 0 | 3-bromothien-2-yl | 503 |
| 183 | CH₂ | 0 | 3-phenoxythien-2-yl | 517 |
| 184 | CH₂ | 0 | 5-methylthio-thien-2-yl | 471 |
| 185 | CH₂ | 0 | 1-methyl-4-bromopyrazol-3-yl | 501 |
| 186 | CH₂ | 0 | 4-I—C₆H₄ | |
| 187 | CH₂ | 0 | 6,7-Me₂-chromon-3-yl | |
| 188 | CH₂ | 0 | 2-(OCH₂CO₂H)-5-NO₂—C₆H₃ | 538 |
| 189 | CH₂ | 0 | 2-(2,6-dichlorobenzyloxy)phenyl | 593 |
| 190 | CH₂ | 0 | 1-(4-chlorobenzyl)pyrazol-3-yl | 533 |
| 191 | CH₂ | 0 | 4-iso-propoxy-C₆H₄ | 477 |
| 192 | CH₂ | 0 | 1-methylbenzimidazol-2-yl | 473 |
| 193 | CH₂ | 0 | 3-Me-C₆H₄ | 433 |
| 194 | CH₂ | 0 | Pyridin-3-yl | 420 |
| 195 | CH₂ | 0 | 2,4-(MeO)₂-pyrimidin-5-yl | |
| 196 | CH₂ | 0 | 3-Cl-5-CF₃-pyridin-2-yl | 522 |
| 197 | CH₂ | 0 | 2,4-Me₂-C₆H₃ | 447 |
| 198 | CH₂ | 0 | 1-methylindol-3-yl | 472 |
| 199 | CH₂ | 0 | 2-methyl-3-(CO₂Et)-fur-5-yl | |
| 200 | CH₂ | 0 | 1-Me-4-Cl-pyrazol-3-yl | 457 |
| 201 | C(O) | 2 | phenyl | 461 |
| 202 | C(O) | 1 | 4-Br—C₆H₄ | 525 |
| 203 | C(O) | 1 | 4-NH₂—C₆H₄ | 462 |
| 204 | C(O) | 1 | 2-Br—C₆H₄ | 525 |
| 205 | C(O) | 1 | 4-F—C₆H₄ | 465 |
| 206 | C(O) | 1 | 2-CF₃—C₆H₄ | |
| 207 | C(O) | 1 | 3-Me—C₆H₄ | 461 |
| 208 | C(O) | 1 | 2-Me—C₆H₄ | 461 |
| 209 | C(O) | 1 | 3-Cl-4-OH—C₆H₃ | 497 |
| 210 | C(O) | 3 | 9,10-dihydrophenanthren-2-yl | 577 |
| 211 | C(O) | 1 | 2-NO₂—C₆H₄ | 492 |
| 212 | C(O) | 1 | 2-Cl—C₆H₄ | 481 |

TABLE I-continued

| Compound | T | n | R³ | M + H |
|---|---|---|---|---|
| 213 | C(O) | 1 | 4-Cl—C₆H₄ | 481 |
| 214 | C(O) | 1 | 2-benzyloxy-C₆H₄ | 553 |
| 215 | C(O) | 2 | 3,4-(OH)₂—C₆H₃ | 493 |
| 216 | C(O) | 1 | 4-NO₂—C₆H₄ | 492 |
| 217 | C(O) | 4 | Phenyl | 489 |
| 218 | C(O) | 1 | 3,4-(MeO)₂—C₆H₃ | 507 |
| 219 | C(O) | 1 | 4-EtO—C₆H₄ | 491 |
| 220 | C(O) | 1 | 3-F-4-OH—C₆H₃ | 481 |
| 221 | C(O) | 3 | Phenyl | 475 |
| 222 | C(O) | 1 | 3,4-methylenedioxyphenyl | 491 |
| 223 | C(O) | 3 | 4-MeO—C₆H₄ | 505 |
| 224 | C(O) | 2 | 4-OH—C₆H₄ | 477 |
| 225 | C(O) | 1 | 4-OH—C₆H₄ | 463 |
| 226 | C(O) | 1 | 4-phenyl-C₆H₄ | 523 |
| 227 | C(O) | 1 | 3,4-Cl₂—C₆H₃ | 515 |
| 228 | C(O) | 2 | 3-OH—C₆H₄ | 477 |
| 229 | C(O) | 2 | 4-Me—C₆H₄ | 475 |
| 230 | C(O) | 3 | 4-NO₂—C₆H₄ | 520 |
| 231 | C(O) | 2 | 3,4-(MeO)₂—C₆H₃ | 521 |
| 232 | C(O) | 3 | 4-Me—C₆H₄ | 489 |
| 233 | C(O) | 2 | C₆F₅ | 551 |
| 234 | C(O) | 3 | Dibenzothien-4-yl | 581 |
| 235 | C(O) | 1 | 4-Me—C₆H₄ | 461 |
| 236 | C(O) | 2 | 4-SH—C₆H₄ | |
| 237 | C(O) | 1 | 4-CF₃O—C₆H₄ | 531 |
| 238 | C(O) | 1 | 4-CH₂Br—C₆H₄ | |
| 239 | C(O) | 3 | 3,4-(MeO)₂—C₆H₃ | 535 |
| 240 | C(O) | 1 | 4-MeO—C₆H₄ | 477 |
| 241 | C(O) | 1 | 4-(NMe₂)—C₆H₄ | 490 |
| 242 | C(O) | 2 | 4-MeO—C₆H₄ | 491 |
| 243 | C(O) | 2 | 2-MeO—C₆H₄ | 491 |
| 244 | C(O) | 1 | 3,4,5-(MeO)₃—C₆H₂ | 537 |
| 245 | C(O) | 2 | 3,4-methylenedioxyphenyl | 505 |
| 246 | C(O) | 2 | Dibenzothien-4-yl | |
| 247 | C(O) | 1 | 3-NH₂—C₆H₄ | 462 |
| 248 | C(O) | 1 | Naphth-1-yl | 497 |
| 249 | C(O) | 1 | 3-MeO-4-OH—C₆H₃ | 493 |
| 250 | C(O) | 1 | Naphth-2-yl | |
| 251 | C(O) | 1 | 3-(1-allyl-6-bromonaphth-2-yloxy)CH₂—C₆H₄ | 721 |
| 252 | C(O) | 1 | 4-NO₂—C₆H₄ | |
| 253 | C(O) | 1 | 3-F-4-MeO—C₆H₃ | 495 |
| 254 | C(O) | 4 | 3-Me—C₆H₄ | 503 |
| 255 | C(O) | 1 | 3-OH—C₆H₄ | 463 |
| 256 | C(O) | 1 | 4-benzyloxy-C₆H₄ | 553 |
| 257 | C(O) | 1 | 4-(3-NO₂—C₆H₄)—C₆H₄ | 568 |
| 258 | C(O) | 1 | 2,5-(Me)₂—C₆H₃ | 475 |
| 259 | C(O) | 1 | 4-I—C₆H₄ | 573 |
| 260 | C(O) | 1 | 4-(4-(1-Me-2-OH-4-(pyridin-3-yl)-butoxy)-C₆H₄)—C₆H₄ | 702 |
| 261 | C(O) | 1 | 3-Br—C₆H₄ | 525 |
| 262 | C(O) | 2 | 3-(n-Pr)—C₆H₄ | 503 |
| 263 | C(O) | 1 | 4-(4-NO₂—C₆H₄CH₂O)—C₆H₄ | 598 |
| 264 | C(O) | 1 | 2,5-(OH)₂—C₆H₃ | |
| 265 | C(O) | 1 | 2-Me-3-NO₂—C₆H₃ | 506 |
| 266 | C(O) | 1 | 4-(CH₂NHCO₂CH₂(fluoren-9-yl))-C₆H₄ | |
| 267 | C(O) | 1 | 3-OH-4-MeO—C₆H₄ | 493 |
| 268 | C(O) | 1 | 3-F—C₆H₄ | 465 |
| 269 | C(O) | 1 | 2-F—C₆H₄ | 465 |
| 270 | C(O) | 1 | 3,5-(MeO)₂-C₆H₃ | 507 |
| 271 | C(O) | 1 | 3-Cl—C₆H₄ | 481 |
| 272 | C(O) | 1 | Phenyl | 447 |
| 273 | C(O) | 1 | 3,5-Me₂—C₆H₃ | 475 |
| 274 | C(O) | 2 | 3-MeO—C₆H₄ | 491 |
| 275 | C(O) | 1 | 2,4-F₂—C₆H₃ | 483 |
| 276 | C(O) | 1 | 2-MeO—C₆H₄ | 477 |
| 277 | C(O) | 1 | 3,4-F₂—C₆H₃ | 483 |
| 278 | C(O) | 1 | 3,5-F₂—C₆H₃ | 483 |
| 279 | C(O) | 5 | phenyl | 503 |
| 280 | S(O)₂ | 0 | 5-(pyridin-2-yl)-thien-2-yl | |
| 281 | C(O) | 0 | 3-S(O)₂Me—C₆H₄ | 511 |
| 282 | C(O) | 0 | 3-MeO-4-NH₂—C₆H₃ | |
| 283 | C(O) | 0 | 3-MeO-4-F—C₆H₃ | 481 |
| 284 | C(O) | 0 | Benzthiazol-6-yl | 490 |
| 285 | C(O) | 0 | 3-MeO—C₆H₄ | 477 |
| 286 | C(O) | 0 | 3-C₆H₅S(O)—C₆H₄ | 557 |
| 287 | C(O) | 0 | 4-S(O)₂Me—C₆H₄ | 511 |
| 288 | C(O) | 0 | 2,4-Cl₂—C₆H₃ | 501 |

TABLE I-continued

| Compound | T | n | R³ | M + H |
|---|---|---|---|---|
| 289 | C(O) | 0 | 4-NO₂—C₆H₄ | 478 |
| 290 | C(O) | 0 | 3-CN—C₆H₄ | 458 |
| 291 | C(O) | 0 | 4-MeO—C₆H₄ | 463 |
| 292 | C(O) | 0 | 4-CN—C₆H₄ | 458 |
| 293 | C(O) | 0 | 2-S(O)₂Me—C₆H₄ | 511 |
| 294 | C(O) | 0 | 2-Cl-4-S(O)₂Me—C₆H₃ | 545 |
| 295 | C(O) | 0 | 3-(C₆H₅S(O)₂CH₂)-4-NO₂—C₆H₃ | 632 |
| 296 | C(O) | 0 | 2-(C₆H₅S(O)₂CH₂)—C₆H₄ | |
| 297 | C(O) | 0 | Benzo[1,2,3]thiadiazol-5-yl | 491 |
| 298 | C(O) | 0 | 4-EtS—C₆H₄ | 493 |
| 299 | C(O) | 0 | 3-CF₃S—C₆H₄ | 533 |
| 300 | C(O) | 0 | 4-CF₃S—C₆H₄ | 533 |
| 301 | C(O) | 0 | 3-CH₃C(O)NH—C₆H₄ | 490 |
| 302 | C(O) | 0 | 3-CH₃-4-NH₂—C₆H₃ | 462 |
| 303 | C(O) | 0 | Indol-7-yl | 472 |
| 304 | C(O) | 0 | 3-CH₃CH₂O-4-CH₃O—C₆H₃ | 507 |
| 305 | C(O) | 0 | 4-(2,5-dihydropyrrol-1-yl )-C₆H₄ | 500 |
| 306 | C(O) | 1 | 3-Br-pyridin-5-yl | 526 |
| 307 | C(O) | 1 | 1-methyl-imidazol-4-yl | 451 |
| 308 | C(O) | 1 | 5-OH-indol-3-yl | 502 |
| 309 | C(O) | 1 | Thiophen-3-yl | 453 |
| 310 | C(O) | 0 | 3-CH₃CH₂S(O)₂—C₆H₄ | 525 |
| 311 | C(O) | 0 | 3-CH₃(CH₂)₂S(O)₂—C₆H₄ | 539 |
| 312 | C(O) | 0 | 3-(CH₃)₂CHCH₂S(O)₂—C₆H₄ | 553 |
| 313 | C(O) | 0 | 3,4-(CH₃S(O)₂)₂—C₆H₃ | 589 |
| 314 | C(O) | 0 | 3-CH₃CH₂O-4-NH₂—C₆H₃ | 492 |
| 315 | C(O) | 1 | Pyridin-4-yl | 448 |
| 316 | C(O) | 0 | 2-CH₃S(O)₂CH₂—C₆H₄ | 525 |
| 317 | C(O) | 0 | 2-NH₂—C₆H₄ | 448 |
| 318 | C(O) | 0 | 1-acetyl-indol-3-yl | |
| 319 | C(O) | 0 | Indol-3-yl | |
| 320 | C(O) | 0 | 3-NH₂(CH₂)₂O—C₆H₄ | |
| 321 | C(O) | 0 | 3-CH₃NHS(O)₂—C₆H₄ | |
| 322 | C(O) | 0 | 3-NH₂S(O)₂—C₆H₄ | |
| 323 | C(O) | 0 | 3-CH₃O(CH₂)₂O—C₆H₄ | |
| 324 | C(O) | 0 | 3-(CH₃)₃COC(O)NH(CH₂)₂O—C₆H₄ | |
| 325 | C(O) | 0 | 1,2,3-benzothiadiazol-6-yl | |
| 326 | C(O) | 0 | 3-HOC(O)CH₂O—C₆H₄ | |
| 327 | C(O) | 0 | 2-CH₃S(O)₂-3-CN-thiophen-5-yl | 542 |
| 328 | C(O) | 0 | 3-CH₃S(O)₂-4-NH₂—C₆H₃ | 526 |
| 329 | C(O) | 0 | 2-CH₃S(O)₂-3-NH₂C(O)-thiophen-5-yl | 560 |
| 330 | C(O) | 0 | 3-CF₃O—C₆H₄ | 501 |
| 331 | C(O) | 0 | 2-(CH₃)₂CHS(O)₂-3-NH₂-thiophen-4-yl | 560 |
| 332 | C(O) | 0 | 2-CH₃S(O)₂-thiophen-5-yl | 517 |
| 333 | C(O) | 0 | 3-CH₃-5-(4-CH₃-1,2,3-thiadiazol-5-yl)-isoxazol-4-yl | 536 |
| 334 | C(O) | 0 | 3-Cl-5-CF₃-pyridin-2-yl | 536 |
| 335 | C(O) | 1 | 4-CF₃O—C₆H₄ | 531 |
| 336 | C(O) | 0 | 1H-benzotriazol-5-yl | 474 |
| 337 | C(O) | 0 | 4-CH₃S(O)₂CH₂—C₆H₄ | 525 |
| 338 | C(O) | 0 | 3-CH₃S(O)₂CH₂—C₆H₄ | 525 |
| 339 | C(O) | 0 | 2-CN—C₆H₄ | 458 |
| 340 | C(O) | 0 | Quinolin-6-yl | 484 |
| 341 | C(O) | 0 | Quinoxalin-6-yl | 485 |
| 342 | C(O) | 0 | 3-NH₂-4-CH₃S(O)₂-thiophen-2-yl | 532 |
| 343 | C(O) | 0 | ![structure: 6-methyl-4-methyl-2H-1,4-benzothiazin-3(4H)-one 1,1-dioxide] | 566 |
| 344 | C(O) | 0 | ![structure: 6-methyl-benzothiazol-2(3H)-one] | |
| 345 | C(O) | 0 | 3-CF₃O—C₆H₄ | 517 |
| 346 | C(O) | 0 | 2,5-(CH₃O)₂—C₆H₃ | 493 |
| 347 | C(O) | 0 | 1-(CH₃)₂CH-benzotriazol-5-yl | |

TABLE I-continued

| Compound | T | n | R³ | M + H |
|---|---|---|---|---|
| 348 | C(O) | 0 | 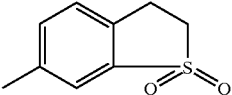 | |
| 349 | C(O) | 0 | 3-HO(CH₂)₂S(O)₂—C₆H₄ | |
| 350 | C(O) | 0 | 2-HO(CH₂)₂S(O)₂—C₆H₄ | |
| 351 | C(O) | 0 | 3-cyclopropylCH₂S(O)₂—C₆H₄ | |
| 352 | C(O) | 0 | 2-CH₃S(O)₂NH—C₆H₄ | 526 |
| 353 | C(O) | 0 | (CF₃)(MeO)(C₆H₅)C | 545 |
| 354 | C(O) | 0 | (C₆H₅)₂CH | 523 |
| 355 | C(O) | 0 | (4-Cl—C₆H₄)(CH₃)₂C | 509 |
| 356 | C(O) | 0 | (C₆H₅)(cyclohexyl)CH | 529 |
| 357 | C(O) | 0 | (4-F—C₆H₄)(CH₃)CH | 479 |
| 358 | C(O) | 1 | 3,4-methylenedioxy-C₆H₄ | 491 |
| 359 | C(O) | 0 | (C₆H₅)(cyclopentyl)CH | 515 |
| 360 | C(O) | 0 | ((CH₃)(CH₃CH₂)CH)(C₆H₅)GH | 503 |
| 361 | C(O) | 0 | 1-phenyl-cyclopentyl | 501 |
| 362 | C(O) | 0 | 1-(4-Cl—C₆H₄)cyclopentyl | 535 |
| 363 | C(O) | 0 | 1-phenyl-cyclopropyl | 473 |
| 364 | C(O) | 0 | 1-phenyl-cyclohexyl | 515 |
| 365 | C(O) | 0 | (C₆H₅)(cyclohexyl)C(OH) | 545 |
| 366 | C(O) | 0 | ((CH₃)₂CH)(C₆H₅)CH | 489 |
| 367 | C(O) | 1 | pyrid-3-yl | 448 |
| 368 | C(O) | 1 | pyrid-2-yl | 448 |
| 369 | C(O) | 1 | 5-Br-pyrid-3-yl | 526 |
| 370 | C(O) | 1 | 2,4-(MeO)₂—C₆H₃ | 507 |
| 371 | C(O) | 1 | 4-benzyloxy-phenyl | 553 |
| 372 | C(O) | 1 | 3-benzyloxy-phenyl | 553 |
| 373 | C(O) | 1 | 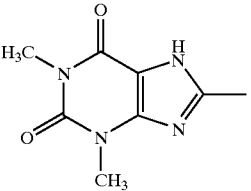 | 549 |
| 374 | C(O) | 0 | 2-EtO—C₆H₄ | 491 |
| 375 | C(O) | 0 | 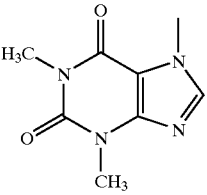 | 549 |
| 376 | C(O) | 1 | 4-n-butoxyphenyl | 519 |
| 377 | C(O) | 1 | indol-1-yl | 486 |
| 378 | C(O) | 1 | 2-NO₂-phenyl | 492 |
| 379 | C(O) | 1 | thien-2-yl | 453 |
| 380 | C(O) | 1 | 3-Cl-4-OH-phenyl | 497 |
| 381 | C(O) | 1 | 2-Br-phenyl | 525 |
| 382 | C(O) | 1 | 3-Br-phenyl | 525 |
| 383 | C(O) | 1 | 3,5-F₂-phenyl | 483 |
| 384 | C(O) | 1 | 3-aminophenyl | 462 |
| 385 | C(O) | 1 | 3,4-(OH)₂-phenyl | 479 |
| 386 | C(O) | 1 | 2,5-(MeO)₂-phenyl | 507 |
| 387 | C(O) | 1 | 4-Me-phenyl | 461 |
| 388 | C(O) | 0 | 5-(4-Cl—C₆H₄-tetrazol-2-yl | 549 |
| 389 | C(O) | 1 | 4-MeS(O)₂-phenyl | 525 |
| 390 | C(O) | 1 | 4-F-phenyl | 465 |
| 391 | C(O) | 1 | 5-Cl-benzo[b]thiophen-3-yl | 537 |
| 392 | C(O) | 1 | 4-CF₃O-phenyl | 531 |
| 393 | C(O) | 1 | 3-Me-5-Cl-benzo[b]thiophen-2-yl | 551 |
| 394 | C(O) | 1 | 2-nitrophenyl | 492 |
| 395 | C(O) | 1 | 4-Cl-5-Me-3-NO₂-pyrazol-1-yl | 530 |
| 396 | C(O) | 1 | 2-CF₃-benzimidazol-1-yl | 555 |
| 397 | C(O) | 1 | 2-EtS-benzimidazol-1-yl | 547 |
| 398 | C(O) | 1 | 2-Me-4-(thien-2-yl)-thiazol-5-yl | 550 |

TABLE I-continued

| Compound | T | n | R³ | M + H |
|---|---|---|---|---|
| 399 | C(O) | 1 | 4-Br-3,5-Me₂-pyrazol-1-yl | 543 |
| 400 | C(O) | 1 | 5-Me-3,4-(NO₂)₂-pyrazol-1-yl | 541 |
| 401 | C(O) | 1 | 4-(3-methyl-butoxy)-phenyl | 533 |
| 402 | C(O) | 1 | 2-tert-butylthio-phenyl | 535 |
| 403 | C(O) | 1 | 4-Cl-3,5-Me₂-pyrazol-1-yl | 499 |
| 404 | C(O) | 1 | 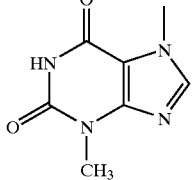 | 535 |
| 405 | C(O) | 1 | 2,4-(NO₂)₂-imidazol-1-yl | 527 |
| 406 | C(O) | 1 | 3,5-Me₂-pyrazol-1-yl | 465 |
| 407 | C(O) | 1 | 4-n-hexyl-phenyl | 531 |
| 408 | C(O) | 0 | 2-NH₂-pyrid-5-yl | 449 |
| 409 | C(O) | 0 | Pyrid-2-yl | 434 |
| 410 | C(O) | 0 | 2-EtS-pyrid-3-yl | 494 |
| 411 | C(O) | 0 | 2-OH-quinolin-4-yl | 500 |
| 412 | C(O) | 0 | 2-OH-pyrid-5-yl | 450 |
| 413 | C(O) | 0 | 2,6-(MeO)₂-pyrid-3-yl | 494 |
| 414 | C(O) | 0 | 2-(imidazol-1-yl)-pyrid-5-yl | 500 |
| 415 | C(O) | 0 | 2-CO₂CH₃-pyrid-3-yl | 492 |
| 416 | C(O) | 0 | 2-Me-pyrid-5-yl | 448 |
| 417 | C(O) | 0 | Quinolin-2-yl | 484 |
| 418 | C(O) | 0 | 6-Me-pyrid-2-yl | 448 |
| 419 | C(O) | 0 | 2-OH-6-Me-pyrid-3-yl | 464 |
| 420 | C(O) | 0 | 8-OH-quinolin-2-yl | 500 |
| 421 | C(O) | 1 | 3-F-phenyl | 465 |
| 422 | C(O) | 0 | Imidazo[1,2-a]pyrid-2-yl | 473 |
| 423 | C(O) | 0 | 2-methyl-[1,8]naphthyridin-3-yl | 499 |
| 424 | C(O) | 0 | [1,6]naphthyridin-2-yl | 485 |
| 425 | C(O) | 0 | 2-methyl-[1,6]naphthyridin-3-yl | 499 |
| 426 | C(O) | 0 | 1-methyl-1H-pyrid-2-one-5-yl | 464 |
| 427 | C(O) | 0 | Quinolin-4-yl | 484 |
| 428 | C(O) | 0 | Quinolin-6-yl | 484 |
| 429 | C(O) | 0 | 3-(CH₃(CH₂)₂S(O)₂)—C₆H₄ | 539 |
| 430 | C(O) | 0 | 5-((pyrid-2-yl)SCH₂)fur-2-yl | 546 |
| 431 | C(O) | 0 | 2-Me-3-OH-quinolin-4-yl | 514 |
| 432 | C(O) | 0 | (pyrid-2-yl)CH=CH | 460 |
| 433 | C(O) | 0 | (2-EtS-pyrid-5-yl)CH=CH | 520 |
| 434 | C(O) | 0 | 1-(5-CF₃-pyrid-2-yl)-piperidin-4-yl | 585 |
| 435 | C(O) | 0 | 2,7-Me₂-imidazo[1,2-a]pyrid-3-yl | 501 |
| 436 | C(O) | 0 | (5-CF₃-pyrid-2-yl)SO₂CH(CH₃) | 594 |
| 437 | C(O) | 1 | 3-(pyrid-2-yl)pyrazol-1-yl | 514 |
| 438 | C(O) | 0 | 3-NH₂-4-CH₃O—C₆H₃ | 478 |
| 439 | C(O) | 0 | 2,5-(CH₃O)₂—C₆H₃ | 493 |
| 440 | C(O) | 0 | 3-F-4-CH₃—C₆H₃ | 465 |
| 441 | C(O) | 0 | 3-phenyl-5-CH₃-isoxazol-4-yl | 514 |
| 442 | C(O) | 0 | 1-phenyl-5-CH₃-pyrazol-4-yl | 513 |
| 443 | C(O) | 0 | 3-CF₃O—C₆H₄ | 517 |
| 444 | C(O) | 0 | 2-CH₃O-5-Cl—C₆H₃ | 497 |
| 445 | C(O) | 0 | 2-CH₃-3-F—C₆H₃ | 465 |
| 446 | C(O) | 0 | 2-(2-phenyl-thiazol-4-yl)phenyl | 592 |
| 447 | C(O) | 0 | 3,4-methylenedioxphenyl | 477 |
| 448 | C(O) | 0 | 5-phenyl-oxazol-4-yl | 500 |
| 449 | C(O) | 0 | 1H-indazol-3-yl | 473 |
| 450 | C(O) | 0 | 1-CH₃-indol-3-yl | 486 |
| 451 | C(O) | 0 | 1-iso-propyl-benztriazol-5-yl | 516 |
| 452 | C(O) | 0 | 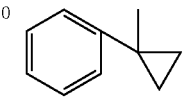 | 473 |
| 453 | C(O) | 0 | 2-CH₃-5-F—C₆H₃ | 465 |
| 454 | C(O) | 0 | 3-CF₃O-4-NH₂—C₆H₃ | 532 |
| 455 | C(O) | 0 | 3-CH₃-5-CF₃-isoxazol-4-yl | 506 |
| 456 | C(O) | 0 | (1,2,4-triazol-1-yl)C(CH₃)₂ | 466 |
| 457 | C(O) | 0 | 2-phenyl-thiazol-4-yl | 516 |
| 458 | C(O) | 0 | 2-CH₃-4-CF₃-thiazol-5-yl | 522 |

TABLE I-continued

| Compound | T | n | R³ | M + H |
|---|---|---|---|---|
| 459 | C(O) | 0 | (benzothiazole fused 2-methylimidazole) | 529 |
| 460 | C(O) | 0 | (methyl, CF₃-substituted thieno[3,2-b]pyridine) | 558 |
| 461 | C(O) | 0 | 3-F-4-CF₃—C₆H₃ | 519 |
| 462 | C(O) | 0 | (2,3-dimethyl-6-methyl-imidazo[1,2-a]pyridine) | 501 |
| 463 | C(O) | 0 | 2-CH₃-benzimidazol-5-yl | 487 |
| 464 | C(O) | 1 | (4-methyl-2H-benzo[b][1,4]thiazin-3(4H)-one) | 534 |
| 465 | C(O) | 0 | 3-iso-propoxy-4-CH₃O—C₆H₃ | 521 |
| 466 | C(O) | 0 | (1-(2-fluorophenyl)-1-methylcyclopentyl) | 519 |
| 467 | C(O) | 0 | (4,6-dimethyl-2H-benzo[b][1,4]thiazin-3(4H)-one) | 534 |
| 468 | C(O) | 0 | 2-CH₃O-5-F—C₆H₃ | 481 |
| 469 | C(O) | 0 | 3-CH₃CH₂O—C₆H₄ | |
| 470 | C(O) | 0 | 2-(C₆H₅S(O)CH₂)—C₆H₄ | |
| 471 | C(O) | 0 | 1H-indol-3-yl | 472 |
| 472 | S(O)₂ | 1 | 2-NO₂—C₆H₄ | 528 |
| 473 | S(O)₂ | 0 | 2-CN—C₆H₄ | 494 |
| 474 | C(O) | 0 | 3-CH₃S(O)₂—C₆H₄ | 511 |
| 475 | C(O) | 0 | 3-S(O)₂NHCH₃—C₆H₄ | 526 |
| 476 | C(O) | 0 | Benzo[1,2,3]thiadiazol-6-yl | 491 |
| 477 | C(O) | 0 | 3-CH₃O(CH₂)₂O—C₆H₄ | 507 |
| 478 | C(O) | 0 | 3,4-(CH₃S(O)₂)₂—C₆H₃ | 589 |
| 479 | C(O) | 0 | 3-CH₃O—C₆H₄ | 463 |
| 480 | C(O) | 0 | 3-CN—C₆H₄ | 458 |
| 481 | C(O) | 0 | 4-F—C₆H₄ | 451 |
| 482 | C(O) | 0 | 3-CH₃O-4-F—C₆H₃ | 481 |
| 483 | C(O) | 0 | 3H-benzothiazol-2-one-6-yl | 506 |
| 484 | C(O) | 0 | 2-CH₃S(O)₂-thien-5-yl | 517 |
| 485 | C(O) | 0 | 3-CH₃-4-NH₂—C₆H₃ | 462 |
| 486 | C(O) | 0 | Benzothiazol-6-yl | 490 |
| 487 | C(O) | 0 | 1H-5-CH₃S(O)₂-indol-2-yl | 550 |
| 488 | C(O) | 0 | 1H-5-CH₃O-indol-2-yl | 502 |
| 489 | C(O) | 0 | 1H-indol-4-yl | 472 |
| 490 | C(O) | 0 | 1H-Benzimidazol-5-yl | 473 |
| 491 | C(O) | 0 | 3,4-methylenedioxyphenyl | 477 |
| 492 | C(O) | 0 | 1H-5-Cl-indol-2-yl | 506 |
| 493 | C(O) | 0 | 1H-5-OH-indol-2-yl | 488 |

TABLE I-continued

| Compound | T | n | R³ | M + H |
|---|---|---|---|---|
| 494 | C(O) | 0 | 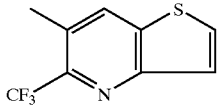 | 558 |
| 495 | C(O) | 0 | 3,4-difluoromethylenedioxyphenyl | 513 |
| 496 | C(O) | 0 | 2-(pyrazol-1-yl)-pyridin-5-yl | 500 |
| 497 | C(O) | 0 | 4-CF₃-pyridin-3-yl | 502 |
| 498 | C(O) | 0 | 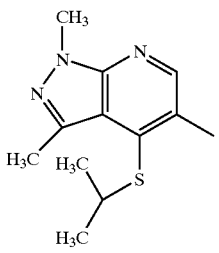 | 576 |
| 499 | C(O) | 0 | 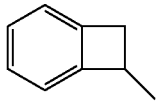 | 459 |
| 500 | C(O) | 0 | 3-n-propoxy-pyridin-2-yl | 492 |
| 501 | C(O) | 1 | 2-(2,4-F₂—C₆H₃)thiazol-4-yl | 566 |
| 502 | C(O) | 0 | 1H-indol-2-yl | 472 |
| 503 | C(O) | 1 | 2-phenyl-5-CH₃-thiazol-4-yl | 544 |
| 504 | C(O) | 0 | 2-S(O)₂NH₂-4-Cl—C₆H₃ | 546 |
| 505 | C(O) | 0 | 2-CN—C₆H₄ | 458 |
| 506 | C(O) | 0 | 1H-indol-7-yl | 472 |
| 507 | C(O) | 0 | 1H-5-F-indol-2-yl | 490 |
| 508 | C(O) | 0 | 1H-pyrazol-4-yl | 423 |
| 509 | C(O) | 0 | 1-CH₃-pyrrol-2-yl | 436 |
| 511 | C(O) | 0 | 3-(pyrrol-1-yl)-4-CN-thien-2-yl | 529 |
| 512 | C(O) | 0 | 3-CH₃O-4-NH₂—C₆H₃ | 478 |
| 513 | C(O) C(O) | 0 | lH-indol-3-yl | 500 |
| 514 | C(O) | 0 | 4-(pyrrol-1-yl)phenyl | 498 |
| 515 | C(O) | 0 | 1-CH₃-indol-2-yl | 486 |
| 516 | C(O) | 1 | 1H-indol-3-yl | 486 |
| 517 | C(O) | 1 | 1H-5-CH₃O-indol-3-yl | 516 |
| 518 | C(O) | 0 | 2-(pyridin-2-yl)-thien-5-yl | 516 |
| 519 | C(O) | 0 | 1H-5-F-indol-2-yl | 490 |
| 520 | C(O) | 1 | 3-CH₃-benzo[b]thiophen-2-yl | 517 |
| 521 | C(O) | 1 | 3,5-(CH₃)₂-4-NO₂-pyrazol-1-yl | 510 |
| 522 | C(O) | 0 | 2-CF₃-[1,6]-naphthyridin-3-yl | 553 |
| 523 | C(O) | 0 | 2-(1-CH₃-5-CF₃-pyrazol-3-yl)-thien-5-yl | 587 |
| 524 | C(O) | 0 | 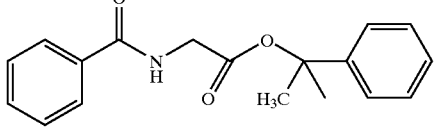 | 638 |
| 525 | C(O) | 1 | 3-Cl—C₆H₄ | 481 |
| 526 | C(O) | 1 | 5-CH₃-3-NO₂-pyrazol-1-yl | 496 |
| 527 | C(O) | 1 | 2-CN—C₆H₄ | 472 |
| 528 | C(O) | 0 | Quinoxalin-2-yl | 485 |
| 529 | C(O) | 0 | Pyrazin-2-yl | 435 |
| 530 | C(O) | 0 | 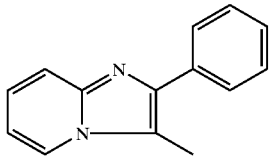 | 549 |

TABLE I-continued

| Compound | T | n | R³ | M + H |
|---|---|---|---|---|
| 531 | C(O) | 0 | 1-tert-butyl-3-CH₃-pyrazol-5-yl | 493 |
| 532 | C(O) | 0 | 2-SH-pyridin-3-yl | 466 |
| 533 | C(O) | 0 | Quinolin-3-yl | 484 |
| 534 | C(O) | 0 | ![3-methyl-7-methyl-1-ethyl-1,8-naphthyridin-4(1H)-one structure] | 543 |
| 535 | C(O) | 0 | 2-ethoxy-phenyl | 477 |
| 536 | C(O) | 1 | 4-NO₂-imidazol-1-yl | 482 |
| 537 | C(O) | 0 | 4-CH₃O-quinolin-2-yl | 514 |
| 538 | C(O) | 0 | 2-SCH₂CH=CH₂-pyridin-3-yl | 506 |
| 539 | C(O) | 0 | 1-iso-propyl-benztriazol-5-yl | 516 |
| 540 | C(O) | 0 | [1,8]-naphthyridin-2-yl | 485 |
| 541 | C(O) | 1 | 2-CH₃-4-phenyl-thiazol-5-yl | 544 |
| 542 | C(O) | 0 | 1-CH₃-indol-2-yl | 486 |
| 543 | C(O) | 0 | 2-phenoxy-pyridin-5-yl-CH=CH | 552 |
| 544 | C(O) | 1 | 3,4-Cl₂—C₆H₃ | 515 |
| 545 | C(O) | 0 | 2-S(O)₂CH₃-3-CN-6-CH₃-pyridin-4-yl | 551 |
| 546 | C(O) | 0 | 3H-Benzothiazol-2-one-6-yl | 506 |
| 547 | C(O) | 0 | 2-CH₃O-pyridin-3-yl | 464 |
| 548 | C(O) | 0 | Isoquinolin-1-yl | 484 |
| 549 | C(O) | 1 | 4-OH—C₆H₄ | 463 |
| 550 | C(O) | 0 | Quinolin-8-yl | 484 |
| 551 | C(O) | 0 | 2-CN—C₆H₄ | 458 |
| 552 | C(O) | 0 | 2-CF₃-[1,8]-naphthyridin-3-yl | 553 |
| 553 | C(O) | 0 | 2-CO₂CH₃-pyridin-6-yl | 492 |
| 554 | C(O) | 0 | Isoquinolin-3-yl | 484 |
| 555 | C(O) | 0 | 3-CH₂S(O)₂CH₃—C₆H₄ | 525 |
| 556 | C(O) | 0 | 2-ethoxy-pyridin-3-yl | 478 |
| 557 | C(O) | 1 | ![2-methyl-5-(pyridin-2-yl)-2H-tetrazole structure] | 516 |
| 558 | C(O) | 0 | 2-CH₃O-pyridin-5-yl | 464 |
| 559 | C(O) | 0 | Indan-1-one-3-yl | 487 |
| 560 | C(O) | 1 | 3-NO₂-[1,2,4]-triazol-1-yl | 483 |
| 561 | C(O) | 0 | 1-(CH₃)₂CH-benzotriazol-5-yl | 516 |
| 562 | C(O) | 1 | 1H-2-CH₃-indol-3-yl | 500 |
| 563 | C(O) | 0 | 3,5-(CH₃)₂-isoxazol-4-yl | 452 |
| 564 | C(O) | 0 | 1,5-(CH₃)₂-pyrazol-4-yl | 451 |
| 565 | C(O) | 0 | Quinoxalin-6-yl | 485 |
| 566 | C(O) | 1 | 3-NO₂-[1,2,4]triazol-1-yl | 483 |
| 567 | C(O) | 0 | 1H-indol-3-yl-CH=CH | 498 |
| 568 | C(O) | 1 | 4-(pyridin-2-yl)-pyrimidin-2-yl-S | 558 |
| 569 | C(O) | 0 | 3-S(O)₂NH₂—C₆H₄ | 512 |
| 570 | C(O) | 1 | 1H-5-OH-indol-3-yl | 502 |
| 571 | C(O) | 0 | 4-CH₂S(O)₂CH₃—C₆H₄ | 525 |
| 572 | C(O) | 0 | ![4-methylisoquinolin-1(2H)-one structure] | 500 |
| 573 | C(O) | 0 | Isoxazol-5-yl | 424 |
| 574 | C(O) | 1 | 1-CH₃-4-NO₂-pyrazol-5-yl | 496 |

TABLE I-continued

| Compound | T | n | R³ | M + H |
|---|---|---|---|---|
| 575 | C(O) | 0 | 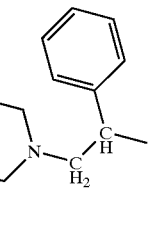 | 645 |
| 576 | C(O) | 0 | 3-ethoxy-4-amino-phenyl | 492 |
| 577 | C(O) | 1 | 1,4-(CH₃)₂-3-CO₂H-pyrrol-2-yl | 508 |
| 578 | C(O) | 0 | 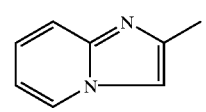 | 473 |
| 579 | C(O) | 0 | 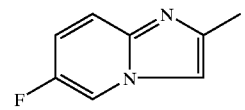 | 491 |
| 580 | C(O) | 0 | 2-OH-quinolin-4-yl | 500 |
| 582 | C(O) | 0 | 3-amino-phenyl | 448 |
| 583 | C(O) | 0 | 3-NHS(O)₂CH₃—C₆H₄ | 526 |
| 584 | C(O) | 0 | 3-C(CH₃)₃OC(O)NH(CH₂)₂O—C₆H₄ | 592 |
| 585 | C(O) | 0 | 3-HO₂CCH₂O—C₆H₄ | 507 |
| 586 | C(O) | 0 | 3-H₂N(CH₂)₂O—C₆H₄ | 492 |
| 587 | C(O) | 0 | 2-NHS(O)₂CH₃—C₆H₄ | 526 |
| 588 | C(O) | 0 | 2-S(O)₂CH₂cyclopropyl-C₆H₄ | 551 |
| 589 | C(O) | 0 | 3-S(O)₂N(CH₃)₂—C₆H₄ | 540 |
| 590 | C(O) | 0 | 3-NO₂-5-S(O)₂CH₃—C₆H₃ | 556 |
| 591 | C(O) | 0 | 3-NH₂-5-S(O)₂CH₃—C₆H₃ | 526 |
| 592 | C(O) | 0 | 1-S(O)₂CH₃-indol-3-yl | |
| 593 | C(O) | 0 | 3-CN-5-S(O)₂CH₃—C₆H₃ | 536 |
| 594 | C(O) | 0 | 1H-5-S(O)₂CH₃-indol-3-yl | 550 |
| 595 | C(O) | 0 | CH(Phenyl)(CH₂piperazin-1-yl) | 545 |
| 596 | C(O) | 1 | 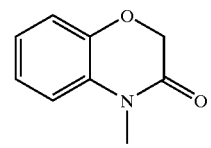 | 518 |
| 597 | C(O) | 0 | 3-S(O)₂NH₂-4-Cl—C₆H₃ | 546 |
| 598 | C(O) | 0 | 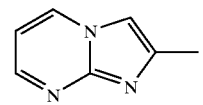 | 474 |
| 599 | C(O) | 0 | 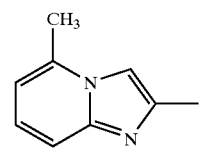 | 487 |
| 600 | C(O) | 0 | 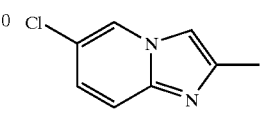 | 507 |

TABLE I-continued

| Compound | T | n | R³ | M + H |
|---|---|---|---|---|
| 601 | C(O) | 0 |  | 487 |
| 602 | C(O) | 0 | 2-NO₂-5-S(O)₂CH₃—C₆H₃ | |
| 603 | C(O) | 0 | 2-NH₂-5-S(O)₂CH₃—C₆H₃ | |

Examples of compounds of formula (Ic) are listed in Table II below.

TABLE II

| Compound | m | p | T | R³ |
|---|---|---|---|---|
| 1 | 1 | 1 | C(O) | 3-MeO-4-NH₂—C₆H₃ |
| 2 | 0 | 2 | C(O) | 3-MeO-4-NH₂—C₆H₃ |
| 3 | 1 | 1 | S(O)₂ | 5-(pyridin-2-yl)-thien-2-yl |
| 4 | 0 | 1 | C(O) | 3-MeO-4-NH₂—C₆H₃ |
| 5 | 1 | 1 | C(O) | 3H-benzothiazol-2-one-6-yl |
| 6 | 1 | 1 | C(O) |  |
| 7 | 1 | 1 | C(O) | [1,8]naphthyridin-2-yl |
| 8 | 1 | 1 | C(O) |  |

Examples of compounds of formula (Id) are listed in Table III below.

TABLE III

| Compound | R³ |
|---|---|
| 1 | 4-F—C₆H₄ |
| 2 | Phenyl |
| 3 | 3,4-F₂—C₆H₃ |

Examples of compounds of formula (If) are listed in Table IV below.

TABLE IV

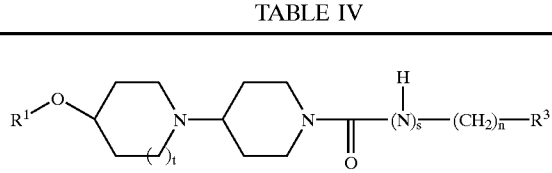

(If)

| Compound | R¹ | t | s | n | R³ |
|---|---|---|---|---|---|
| 1 | 2-CH₃-4-Cl—C₆H₃ | 1 | 0 | 0 | 3-CH₃S(O)₂—C₆H₄ |
| 2 | 3-Cl-4-F—C₆H₃ | 1 | 0 | 0 | 3-CH₃S(O)₂—C₆H₄ |
| 3 | 3-F-4-Cl—C₆H₃ | 1 | 0 | 0 | 3-CH₃S(O)₂—C₆H₄ |
| 4 | 3-CH₃O-4-Cl—C₆H₃ | 1 | 0 | 0 | 3-CH₃S(O)₂—C₆H₄ |
| 5 | 2-CH₃O-4-F—C₆H₃ | 1 | 0 | 0 | 3-CH₃S(O)₂—C₆H₄ |
| 6 | 4-CH₃O—C₆H₄ | 1 | 0 | 0 | 3-CH₃S(O)₂—C₆H₄ |
| 7 | 4-CH₃O—C₆H₄ | 0 | 0 | 0 | 3-CH₃S(O)₂—C₆H₄ |
| 8 | 4-Cl—C₆H₄ | 0 | 0 | 0 | 3-CH₃S(O)₂—C₆H₄ |
| 9 | 3,4-Cl₂—C₆H₃ | 0 | 0 | 0 | 3-CH₃S(O)₂—C₆H₄ |
| 10 | 4-CN—C₆H₄ | 0 | 0 | 0 | 3-CH₃S(O)₂—C₆H₄ |
| 11 | 3,4-F₂—C₆H₃ | 0 | 0 | 0 | 3-CH₃S(O)₂—C₆H₄ |
| 12 | 4-F—C₆H₄ | 0 | 0 | 0 | 3-CH₃S(O)₂—C₆H₄ |
| 13 | 4-CH₃C(O)NH—C₆H₄ | 1 | 0 | 0 | 3-CH₃S(O)₂—C₆H₄ |
| 14 | 4-CH₃—C₆H₄ | 1 | 0 | 0 | 3-CH₃S(O)₂—C₆H₄ |
| 15 | 3-CH₃-4-Cl—C₆H₃ | 1 | 0 | 0 | 3-CH₃S(O)₂—C₆H₄ |
| 16 | 4-Cl—C₆H₄ | 1 | 0 | 0 | 3-CH₃S(O)₂—C₆H₄ |
| 17 | 4-F—C₆H₄ | 1 | 0 | 0 | 3-CH₃S(O)₂—C₆H₄ |
| 18 | 2,4-Cl₂—C₆H₃ | 1 | 0 | 0 | 3-CH₃S(O)₂—C₆H₄ |
| 19 | 2-Cl-4-F—C₆H₃ | 1 | 0 | 0 | 3-CH₃S(O)₂—C₆H₄ |
| 20 | 2,4-F₂—C₆H₃ | 1 | 0 | 0 | 3-CH₃S(O)₂—C₆H₄ |
| 21 | 2-F-4-Cl—C₆H₃ | 1 | 0 | 0 | 3-CH₃S(O)₂—C₆H₄ |
| 22 | 2-CH₃-4-F—C₆H₃ | 1 | 0 | 0 | 3-CH₃S(O)₂—C₆H₄ |

TABLE IV-continued (If)

$$R^1-O-\underset{(\phantom{X})_t}{\underset{|}{\bigcirc}}-N-\underset{|}{\bigcirc}-N-\underset{O}{\overset{H}{\underset{\|}{C}}}-(N)_s-(CH_2)_n-R^3$$

| Compound | R$^1$ | t | s | n | R$^3$ |
|---|---|---|---|---|---|
| 23 | 2-CH$_3$-4-Cl—C$_6$H$_3$ | 1 | 0 | 0 | 3-CH$_3$O-4-NH$_2$—C$_6$H$_3$ |
| 24 | 3-F-4-Cl—C$_6$H$_3$ | 1 | 0 | 0 | 3-CH$_3$O-4-NH$_2$—C$_6$H$_3$ |
| 25 | 2-CH$_3$O-4-Cl—C$_6$H$_3$ | 1 | 0 | 0 | 3-CH$_3$O-4-NH$_2$—C$_6$H$_3$ |
| 26 | 2-CH$_3$O-4-F—C$_6$H$_3$ | 1 | 0 | 0 | 3-CH$_3$O-4-NH$_2$—C$_6$H$_3$ |
| 27 | 4-CH$_3$O—C$_6$H$_4$ | 1 | 0 | 0 | 3-CH$_3$O-4-NH$_2$—C$_6$H$_3$ |
| 28 | 3-Cl-4-F—C$_6$H$_3$ | 1 | 0 | 0 | 3-CH$_3$O-4-NH$_2$—C$_6$H$_3$ |
| 29 | 4-CH$_3$—C$_6$H$_4$ | 1 | 0 | 0 | 3-CH$_3$O-4-NH$_2$—C$_6$H$_3$ |
| 30 | 3-CH$_3$-4-Cl—C$_6$H$_3$ | 1 | 0 | 0 | 3-CH$_3$O-4-NH$_2$—C$_6$H$_3$ |
| 31 | 4-Cl—C$_6$H$_4$ | 1 | 0 | 0 | 3-CH$_3$O-4-NH$_2$—C$_6$H$_3$ |
| 32 | 4-F—C$_6$H$_4$ | 1 | 0 | 0 | 3-CH$_3$O-4-NH$_2$—C$_6$H$_3$ |
| 33 | 2,4-Cl$_2$—C$_6$H$_3$ | 1 | 0 | 0 | 3-CH$_3$O-4-NH$_2$—C$_6$H$_3$ |
| 34 | 2-Cl-4-F—C$_6$H$_3$ | 1 | 0 | 0 | 3-CH$_3$O-4-NH$_2$—C$_6$H$_3$ |
| 35 | 2,4-F$_2$—C$_6$H$_3$ | 1 | 0 | 0 | 3-CH$_3$O-4-NH$_2$—C$_6$H$_3$ |
| 36 | 2-F-4-Cl—C$_6$H$_3$ | 1 | 0 | 0 | 3-CH$_3$O-4-NH$_2$—C$_6$H$_3$ |
| 37 | 2-CH$_3$-4-F—C$_6$H$_3$ | 1 | 0 | 0 | 3-CH$_3$O-4-NH$_2$—C$_6$H$_3$ |
| 38 | 2-CH$_3$-4-Cl—C$_6$H$_3$ | 1 | 0 | 0 | 1,2,3-benzthiadiazol-5-yl |
| 39 | 3-F-4-Cl—C$_6$H$_3$ | 1 | 0 | 0 | 1,2,3-benzthiadiazol-5-yl |
| 40 | 2-CH$_3$O-4-Cl—C$_6$H$_3$ | 1 | 0 | 0 | 1,2,3-benzthiadiazol-5-yl |
| 41 | 2-CH$_3$O-4-F—C$_6$H$_3$ | 1 | 0 | 0 | 1,2,3-benzthiadiazol-5-yl |
| 42 | 4-CH$_3$O—C$_6$H$_4$ | 1 | 0 | 0 | 1,2,3-benzthiadiazol-5-yl |
| 43 | 3-Cl-4-F—C$_6$H$_3$ | 1 | 0 | 0 | 1,2,3-benzthiadiazol-5-yl |
| 44 | 4-CH$_3$—C$_6$H$_4$ | 1 | 0 | 0 | 1,2,3-benzthiadiazol-5-yl |
| 45 | 3-Cl-4-CH$_3$—C$_6$H$_3$ | 1 | 0 | 0 | 1,2,3-benzthiadiazol-5-yl |
| 46 | 4-Cl—C$_6$H$_4$ | 1 | 0 | 0 | 1,2,3-benzthiadiazol-5-yl |
| 47 | 4-F—C$_6$H$_4$ | 1 | 0 | 0 | 1,2,3-benzthiadiazol-5-yl |
| 48 | 2,4-Cl$_2$—C$_6$H$_3$ | 1 | 0 | 0 | 1,2,3-benzthiadiazol-5-yl |
| 49 | 2-Cl-4-F—C$_6$H$_3$ | 1 | 0 | 0 | 1,2,3-benzthiadiazol-5-yl |
| 50 | 2,4-F$_2$—C$_6$H$_3$ | 1 | 0 | 0 | 1,2,3-benzthiadiazol-5-yl |
| 51 | 2-F-4-Cl—C$_6$H$_3$ | 1 | 0 | 0 | 1,2,3-benzthiadiazol-5-yl |
| 52 | 2-CH$_3$-4-F—C$_6$H$_3$ | 1 | 0 | 0 | 1,2,3-benzthiadiazol-5-yl |
| 53 | 3,4-Cl$_2$—C$_6$H$_3$ | 1 | 1 | 0 | 3-CN—C$_6$H$_4$ |
| 54 | 3,4-Cl$_2$—C$_6$H$_3$ | 1 | 1 | 0 | 3-CH$_3$S(O)$_2$—C$_6$H$_4$ |
| 55 | 2-CH$_3$-4-Cl—C$_6$H$_3$ | 1 | 0 | 0 | 2-CH$_3$S(O)$_2$—C$_6$H$_4$ |
| 56 | 3-Cl-4-F—C$_6$H$_3$ | 1 | 0 | 0 | 2-CH$_3$S(O)$_2$—C$_6$H$_4$ |
| 57 | 3-F-4-Cl—C$_6$H$_3$ | 1 | 0 | 0 | 2-CH$_3$S(O)$_2$—C$_6$H$_4$ |
| 58 | 3-CH$_3$O-4-Cl—C$_6$H$_3$ | 1 | 0 | 0 | 2-CH$_3$S(O)$_2$—C$_6$H$_4$ |
| 59 | 2-CH$_3$O-4-F—C$_6$H$_3$ | 1 | 0 | 0 | 2-CH$_3$S(O)$_2$—C$_6$H$_4$ |
| 60 | 4-CH$_3$O—C$_6$H$_4$ | 1 | 0 | 0 | 2-CH$_3$S(O)$_2$—C$_6$H$_4$ |
| 61 | 4-CH$_3$C(O)NH—C$_6$H$_4$ | 1 | 0 | 0 | 2-CH$_3$S(O)$_2$—C$_6$H$_4$ |
| 62 | 4-CH$_3$—C$_6$H$_4$ | 1 | 0 | 0 | 2-CH$_3$S(O)$_2$—C$_6$H$_4$ |
| 63 | 3-CH$_3$-4-Cl—C$_6$H$_3$ | 1 | 0 | 0 | 2-CH$_3$S(O)$_2$—C$_6$H$_4$ |
| 64 | 4-Cl—C$_6$H$_4$ | 1 | 0 | 0 | 2-CH$_3$S(O)$_2$—C$_6$H$_4$ |
| 65 | 4-F—C$_6$H$_4$ | 1 | 0 | 0 | 2-CH$_3$S(O)$_2$—C$_6$H$_4$ |
| 66 | 2,4-Cl$_2$—C$_6$H$_3$ | 1 | 0 | 0 | 2-CH$_3$S(O)$_2$—C$_6$H$_4$ |
| 67 | 2-Cl-4-F—C$_6$H$_3$ | 1 | 0 | 0 | 2-CH$_3$S(O)$_2$—C$_6$H$_4$ |
| 68 | 2,4-F$_2$—C$_6$H$_3$ | 1 | 0 | 0 | 2-CH$_3$S(O)$_2$—C$_6$H$_4$ |
| 69 | 2-F-4-Cl—C$_6$H$_3$ | 1 | 0 | 0 | 2-CH$_3$S(O)$_2$—C$_6$H$_4$ |
| 70 | 2-CH$_3$-4-F—C$_6$H$_3$ | 1 | 0 | 0 | 2-CH$_3$S(O)$_2$—C$_6$H$_4$ |
| 71 | 2-CH$_3$-4-Cl—C$_6$H$_3$ | 1 | 0 | 0 | 2-CH$_3$S(O)$_2$-thiophen-5-yl |
| 72 | 3-Cl-4-F—C$_6$H$_3$ | 1 | 0 | 0 | 2-CH$_3$S(O)$_2$-thiophen-5-yl |
| 73 | 3-F-4-Cl—C$_6$H$_3$ | 1 | 0 | 0 | 2-CH$_3$S(O)$_2$-thiophen-5-yl |
| 74 | 3-CH$_3$O-4-Cl—C$_6$H$_3$ | 1 | 0 | 0 | 2-CH$_3$S(O)$_2$-thiophen-5-yl |
| 75 | 2-CH$_3$O-4-F—C$_6$H$_3$ | 1 | 0 | 0 | 2-CH$_3$S(O)$_2$-thiophen-5-yl |
| 76 | 4-CH$_3$O—C$_6$H$_4$ | 1 | 0 | 0 | 2-CH$_3$S(O)$_2$-thiophen-5-yl |
| 77 | 4-CH$_3$C(O)NH—C$_6$H$_4$ | 1 | 0 | 0 | 2-CH$_3$S(O)$_2$-thiophen-5-yl |
| 78 | 4-CH$_3$—C$_6$H$_4$ | 1 | 0 | 0 | 2-CH$_3$S(O)$_2$-thiophen-5-yl |
| 79 | 3-CH$_3$-4-Cl—C$_6$H$_3$ | 1 | 0 | 0 | 2-CH$_3$S(O)$_2$-thiophen-5-yl |
| 80 | 4-Cl—C$_6$H$_4$ | 1 | 0 | 0 | 2-CH$_3$S(O)$_2$-thiophen-5-yl |
| 81 | 4-F—C$_6$H$_4$ | 1 | 0 | 0 | 2-CH$_3$S(O)$_2$-thiophen-5-yl |
| 82 | 2,4-Cl$_2$—C$_6$H$_3$ | 1 | 0 | 0 | 2-CH$_3$S(O)$_2$-thiophen-5-yl |
| 83 | 2-Cl-4-F—C$_6$H$_3$ | 1 | 0 | 0 | 2-CH$_3$S(O)$_2$-thiophen-5-yl |
| 84 | 2,4-F$_2$—C$_6$H$_3$ | 1 | 0 | 0 | 2-CH$_3$S(O)$_2$-thiophen-5-yl |
| 85 | 2-F-4-Cl—C$_6$H$_3$ | 1 | 0 | 0 | 2-CH$_3$S(O)$_2$-thiophen-5-yl |
| 86 | 2-CH$_3$-4-F—C$_6$H$_3$ | 1 | 0 | 0 | 2-CH$_3$S(O)$_2$-thiophen-5-yl |
| 87 | 3-Cl-4-CH$_3$—C$_6$H$_3$ | 1 | 0 | 0 | 3-CH$_3$S(O)$_2$—C$_6$H$_4$ |
| 88 | 3-Cl-4-CH$_3$—C$_6$H$_3$ | 1 | 0 | 0 | 3-CH$_3$O-4-NH$_2$—C$_6$H$_3$ |
| 89 | 3-CH$_3$-4-Cl—C$_6$H$_3$ | 1 | 0 | 0 | 1,2,3-benzthiadiazol-5-yl |
| 90 | 3-Cl-4-CH$_3$—C$_6$H$_3$ | 1 | 0 | 0 | 2-CH$_3$S(O)$_2$—C$_6$H$_4$ |

TABLE IV-continued

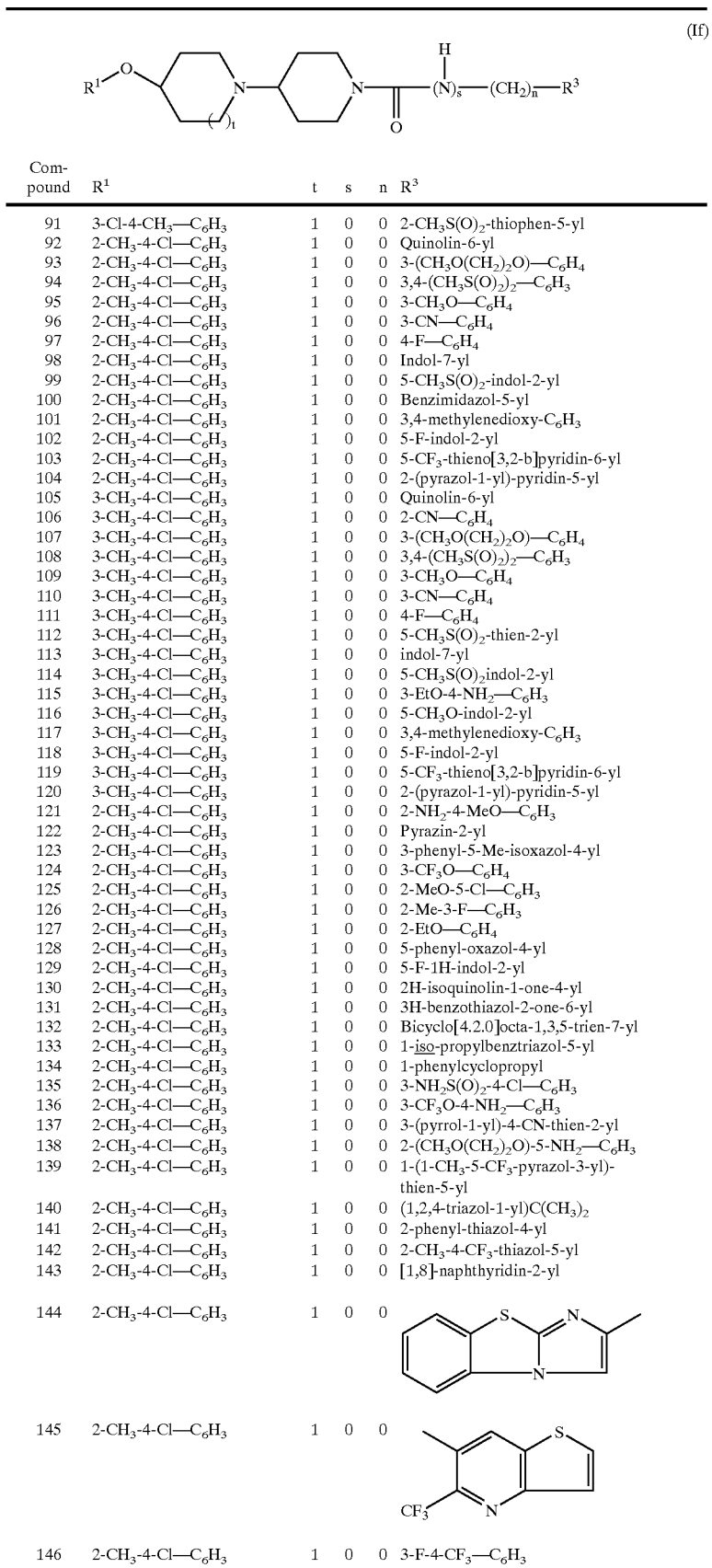

(If)

| Compound | R¹ | t | s | n | R³ |
|---|---|---|---|---|---|
| 91 | 3-Cl-4-CH$_3$—C$_6$H$_3$ | 1 | 0 | 0 | 2-CH$_3$S(O)$_2$-thiophen-5-yl |
| 92 | 2-CH$_3$-4-Cl—C$_6$H$_3$ | 1 | 0 | 0 | Quinolin-6-yl |
| 93 | 2-CH$_3$-4-Cl—C$_6$H$_3$ | 1 | 0 | 0 | 3-(CH$_3$O(CH$_2$)$_2$O)—C$_6$H$_4$ |
| 94 | 2-CH$_3$-4-Cl—C$_6$H$_3$ | 1 | 0 | 0 | 3,4-(CH$_3$S(O)$_2$)$_2$—C$_6$H$_3$ |
| 95 | 2-CH$_3$-4-Cl—C$_6$H$_3$ | 1 | 0 | 0 | 3-CH$_3$O—C$_6$H$_4$ |
| 96 | 2-CH$_3$-4-Cl—C$_6$H$_3$ | 1 | 0 | 0 | 3-CN—C$_6$H$_4$ |
| 97 | 2-CH$_3$-4-Cl—C$_6$H$_3$ | 1 | 0 | 0 | 4-F—C$_6$H$_4$ |
| 98 | 2-CH$_3$-4-Cl—C$_6$H$_3$ | 1 | 0 | 0 | Indol-7-yl |
| 99 | 2-CH$_3$-4-Cl—C$_6$H$_3$ | 1 | 0 | 0 | 5-CH$_3$S(O)$_2$-indol-2-yl |
| 100 | 2-CH$_3$-4-Cl—C$_6$H$_3$ | 1 | 0 | 0 | Benzimidazol-5-yl |
| 101 | 2-CH$_3$-4-Cl—C$_6$H$_3$ | 1 | 0 | 0 | 3,4-methylenedioxy-C$_6$H$_3$ |
| 102 | 2-CH$_3$-4-Cl—C$_6$H$_3$ | 1 | 0 | 0 | 5-F-indol-2-yl |
| 103 | 2-CH$_3$-4-Cl—C$_6$H$_3$ | 1 | 0 | 0 | 5-CF$_3$-thieno[3,2-b]pyridin-6-yl |
| 104 | 2-CH$_3$-4-Cl—C$_6$H$_3$ | 1 | 0 | 0 | 2-(pyrazol-1-yl)-pyridin-5-yl |
| 105 | 3-CH$_3$-4-Cl—C$_6$H$_3$ | 1 | 0 | 0 | Quinolin-6-yl |
| 106 | 3-CH$_3$-4-Cl—C$_6$H$_3$ | 1 | 0 | 0 | 2-CN—C$_6$H$_4$ |
| 107 | 3-CH$_3$-4-Cl—C$_6$H$_3$ | 1 | 0 | 0 | 3-(CH$_3$O(CH$_2$)$_2$O)—C$_6$H$_4$ |
| 108 | 3-CH$_3$-4-Cl—C$_6$H$_3$ | 1 | 0 | 0 | 3,4-(CH$_3$S(O)$_2$)$_2$—C$_6$H$_3$ |
| 109 | 3-CH$_3$-4-Cl—C$_6$H$_3$ | 1 | 0 | 0 | 3-CH$_3$O—C$_6$H$_4$ |
| 110 | 3-CH$_3$-4-Cl—C$_6$H$_3$ | 1 | 0 | 0 | 3-CN—C$_6$H$_4$ |
| 111 | 3-CH$_3$-4-Cl—C$_6$H$_3$ | 1 | 0 | 0 | 4-F—C$_6$H$_4$ |
| 112 | 3-CH$_3$-4-Cl—C$_6$H$_3$ | 1 | 0 | 0 | 5-CH$_3$S(O)$_2$-thien-2-yl |
| 113 | 3-CH$_3$-4-Cl—C$_6$H$_3$ | 1 | 0 | 0 | indol-7-yl |
| 114 | 3-CH$_3$-4-Cl—C$_6$H$_3$ | 1 | 0 | 0 | 5-CH$_3$S(O)$_2$indol-2-yl |
| 115 | 3-CH$_3$-4-Cl—C$_6$H$_3$ | 1 | 0 | 0 | 3-EtO-4-NH$_2$—C$_6$H$_3$ |
| 116 | 3-CH$_3$-4-Cl—C$_6$H$_3$ | 1 | 0 | 0 | 5-CH$_3$O-indol-2-yl |
| 117 | 3-CH$_3$-4-Cl—C$_6$H$_3$ | 1 | 0 | 0 | 3,4-methylenedioxy-C$_6$H$_3$ |
| 118 | 3-CH$_3$-4-Cl—C$_6$H$_3$ | 1 | 0 | 0 | 5-F-indol-2-yl |
| 119 | 3-CH$_3$-4-Cl—C$_6$H$_3$ | 1 | 0 | 0 | 5-CF$_3$-thieno[3,2-b]pyridin-6-yl |
| 120 | 3-CH$_3$-4-Cl—C$_6$H$_3$ | 1 | 0 | 0 | 2-(pyrazol-1-yl)-pyridin-5-yl |
| 121 | 2-CH$_3$-4-Cl—C$_6$H$_3$ | 1 | 0 | 0 | 2-NH$_2$-4-MeO—C$_6$H$_3$ |
| 122 | 2-CH$_3$-4-Cl—C$_6$H$_3$ | 1 | 0 | 0 | Pyrazin-2-yl |
| 123 | 2-CH$_3$-4-Cl—C$_6$H$_3$ | 1 | 0 | 0 | 3-phenyl-5-Me-isoxazol-4-yl |
| 124 | 2-CH$_3$-4-Cl—C$_6$H$_3$ | 1 | 0 | 0 | 3-CF$_3$O—C$_6$H$_4$ |
| 125 | 2-CH$_3$-4-Cl—C$_6$H$_3$ | 1 | 0 | 0 | 2-MeO-5-Cl—C$_6$H$_3$ |
| 126 | 2-CH$_3$-4-Cl—C$_6$H$_3$ | 1 | 0 | 0 | 2-Me-3-F—C$_6$H$_3$ |
| 127 | 2-CH$_3$-4-Cl—C$_6$H$_3$ | 1 | 0 | 0 | 2-EtO—C$_6$H$_4$ |
| 128 | 2-CH$_3$-4-Cl—C$_6$H$_3$ | 1 | 0 | 0 | 5-phenyl-oxazol-4-yl |
| 129 | 2-CH$_3$-4-Cl—C$_6$H$_3$ | 1 | 0 | 0 | 5-F-1H-indol-2-yl |
| 130 | 2-CH$_3$-4-Cl—C$_6$H$_3$ | 1 | 0 | 0 | 2H-isoquinolin-1-one-4-yl |
| 131 | 2-CH$_3$-4-Cl—C$_6$H$_3$ | 1 | 0 | 0 | 3H-benzothiazol-2-one-6-yl |
| 132 | 2-CH$_3$-4-Cl—C$_6$H$_3$ | 1 | 0 | 0 | Bicyclo[4.2.0]octa-1,3,5-trien-7-yl |
| 133 | 2-CH$_3$-4-Cl—C$_6$H$_3$ | 1 | 0 | 0 | 1-*iso*-propylbenztriazol-5-yl |
| 134 | 2-CH$_3$-4-Cl—C$_6$H$_3$ | 1 | 0 | 0 | 1-phenylcyclopropyl |
| 135 | 2-CH$_3$-4-Cl—C$_6$H$_3$ | 1 | 0 | 0 | 3-NH$_2$S(O)$_2$-4-Cl—C$_6$H$_3$ |
| 136 | 2-CH$_3$-4-Cl—C$_6$H$_3$ | 1 | 0 | 0 | 3-CF$_3$O-4-NH$_2$—C$_6$H$_3$ |
| 137 | 2-CH$_3$-4-Cl—C$_6$H$_3$ | 1 | 0 | 0 | 3-(pyrrol-1-yl)-4-CN-thien-2-yl |
| 138 | 2-CH$_3$-4-Cl—C$_6$H$_3$ | 1 | 0 | 0 | 2-(CH$_3$O(CH$_2$)$_2$O)-5-NH$_2$—C$_6$H$_3$ |
| 139 | 2-CH$_3$-4-Cl—C$_6$H$_3$ | 1 | 0 | 0 | 1-(1-CH$_3$-5-CF$_3$-pyrazol-3-yl)-thien-5-yl |
| 140 | 2-CH$_3$-4-Cl—C$_6$H$_3$ | 1 | 0 | 0 | (1,2,4-triazol-1-yl)C(CH$_3$)$_2$ |
| 141 | 2-CH$_3$-4-Cl—C$_6$H$_3$ | 1 | 0 | 0 | 2-phenyl-thiazol-4-yl |
| 142 | 2-CH$_3$-4-Cl—C$_6$H$_3$ | 1 | 0 | 0 | 2-CH$_3$-4-CF$_3$-thiazol-5-yl |
| 143 | 2-CH$_3$-4-Cl—C$_6$H$_3$ | 1 | 0 | 0 | [1,8]-naphthyridin-2-yl |
| 144 | 2-CH$_3$-4-Cl—C$_6$H$_3$ | 1 | 0 | 0 | ![benzothiazole-imidazole structure] |
| 145 | 2-CH$_3$-4-Cl—C$_6$H$_3$ | 1 | 0 | 0 | ![thienopyridine with CF$_3$ structure] |
| 146 | 2-CH$_3$-4-Cl—C$_6$H$_3$ | 1 | 0 | 0 | 3-F-4-CF$_3$—C$_6$H$_3$ |

TABLE IV-continued (If)

[Structure: R¹—O—[piperidine]ₜ—N—[piperidine]—N—C(=O)—(N)ₛ—(CH₂)ₙ—R³ with NH]

| Compound | R¹ | t | s | n | R³ |
|---|---|---|---|---|---|
| 147 | 2-CH₃-4-Cl—C₆H₃ | 1 | 0 | 0 | 2-phenyl-3-methyl-imidazo[1,2-a]pyridin-yl |
| 148 | 2-CH₃-4-Cl—C₆H₃ | 1 | 0 | 0 | 2,3-dimethyl-6-methyl-imidazo[1,2-a]pyridin-yl |
| 149 | 2-CH₃-4-Cl—C₆H₃ | 1 | 0 | 0 | 2-CH₃-benzimidazol-5-yl |
| 150 | 2-CH₃-4-Cl—C₆H₃ | 1 | 0 | 1 | 4-methyl-3-oxo-3,4-dihydro-2H-benzo[1,4]thiazin-yl |
| 151 | 2-CH₃-4-Cl—C₆H₃ | 1 | 0 | 0 | 1-(2-fluorophenyl)-1-methyl-cyclopentyl |
| 152 | 2-CH₃-4-Cl—C₆H₃ | 1 | 0 | 0 | 1,5-dimethyl-pyrazol-3-yl |
| 153 | 2-CH₃-4-Cl—C₆H₃ | 1 | 0 | 0 | 2-CH₃O-5-F—C₆H₃ |
| 154 | 3-CH₃-4-Cl—C₆H₃ | 1 | 0 | 0 | 3-NH₂-4-CH₃O—C₆H₃ |
| 155 | 3-CH₃-4-Cl—C₆H₃ | 1 | 0 | 0 | 2,5-(CH₃O)₂—C₆H₃ |
| 156 | 3-CH₃-4-Cl—C₆H₃ | 1 | 0 | 0 | 3-F-4-CH₃—C₆H₃ |
| 157 | 3-CH₃-4-Cl—C₆H₃ | 1 | 0 | 0 | Pyrazin-2-yl |
| 158 | 3-CH₃-4-Cl—C₆H₃ | 1 | 0 | 0 | 3-phenyl-5-CH₃-isoxazol-4-yl |
| 159 | 3-CH₃-4-Cl—C₆H₃ | 1 | 0 | 0 | 1-phenyl-5-CH₃-pyrazol-4-yl |
| 160 | 3-CH₃-4-Cl—C₆H₃ | 1 | 0 | 0 | 3-CF₃O—C₆H₄ |
| 161 | 3-CH₃-4-Cl—C₆H₃ | 1 | 0 | 0 | 2-CH₃O-5-Cl—C₆H₃ |
| 162 | 3-CH₃-4-Cl—C₆H₃ | 1 | 0 | 0 | 2-CH₃-3-F—C₆H₃ |
| 163 | 3-CH₃-4-Cl—C₆H₃ | 1 | 0 | 0 | 2-CH₃CH₂O—C₆H₄ |
| 164 | 3-CH₃-4-Cl—C₆H₃ | 1 | 0 | 0 | 2-(2-phenyl-thiazol-4-yl)-phenyl |
| 165 | 3-CH₃-4-Cl—C₆H₃ | 1 | 0 | 0 | 1,3,5-trimethyl-4-(isopropylthio)-pyrazolo[3,4-b]pyridin-yl |
| 166 | 3-CH₃-4-Cl—C₆H₃ | 1 | 0 | 0 | 3,4-methylenedioxyphenyl |
| 167 | 3-CH₃-4-Cl—C₆H₃ | 1 | 0 | 0 | 5-phenyl-oxazol-4-yl |
| 168 | 3-CH₃-4-Cl—C₆H₃ | 1 | 0 | 0 | Quinoxazlin-2-yl |
| 169 | 3-CH₃-4-Cl—C₆H₃ | 1 | 0 | 0 | 1H-Pyrazol-4-yl |
| 170 | 3-CH₃-4-Cl—C₆H₃ | 1 | 0 | 0 | 1-CH₃-indol-3-yl |

TABLE IV-continued (If)

R¹O—[piperidine]—N—[piperidine]—N—C(=O)—(N)ₛ—(CH₂)ₙ—R³ with (  )ₜ and NH

| Compound | R¹ | t | s | n | R³ |
|---|---|---|---|---|---|
| 171 | 3-CH₃-4-Cl—C₆H₃ | 1 | 0 | 0 | (bicyclo[4.2.0] benzocyclobutane-methyl) |
| 172 | 3-CH₃-4-Cl—C₆H₃ | 1 | 0 | 0 | 1-iso-propyl-benztriazol-5-yl |
| 173 | 3-CH₃-4-Cl—C₆H₃ | 1 | 0 | 0 | 3-n-propoxy-pyridin-2-yl |
| 174 | 3-HC₃-4-Cl—C₆H₃ | 1 | 0 | 0 | 2-CH₃-5-F—C₆H₃ |
| 175 | 3-CH₃-4-Cl—C₆H₃ | 1 | 0 | 1 | (2-S(O)₂NHCH₃—C₆H₄)S |
| 176 | 3-CH₃-4-Cl—C₆H₃ | 1 | 0 | 0 | 3-CH₃-5-CF₃-isoxazol-4-yl |
| 177 | 3-CH₃-4-Cl—C₆H₃ | 1 | 0 | 1 | 2-(2,4-F₂—C₆H₃)thiazol-4-yl |
| 178 | 3-CH₃-4-Cl—C₆H₃ | 1 | 0 | 0 | 2-(CH₃O(CH₂)₂O)-5-NH₂—C₆H₃ |
| 179 | 3-CH₃-4-Cl—C₆H₃ | 1 | 0 | 0 | 2-phenyl-thiazol-4-yl |
| 180 | 3-CH₃-4-Cl—C₆H₃ | 1 | 0 | 0 | (2-methyl-benzo[d]imidazo[2,1-b]thiazol-yl) |
| 181 | 3-CH₃-4-Cl—C₆H₃ | 1 | 0 | 0 | (methyl-CF₃-thieno[3,2-b]pyridinyl) |
| 182 | 3-CH₃-4-Cl—C₆H₃ | 1 | 0 | 0 | 3-F-4-CF₃—C₆H₃ |
| 183 | 3-CH₃-4-Cl—C₆H₃ | 1 | 0 | 0 | (3-methyl-2-phenyl-imidazo[1,2-a]pyridinyl) |
| 184 | 3-CH₃-4-Cl—C₆H₃ | 1 | 0 | 0 | (2,3-dimethyl-6-methyl-imidazo[1,2-a]pyridinyl) |
| 185 | 3-CH₃-4-Cl—C₆H₃ | 1 | 0 | 0 | 3-iso-propoxy-C₆H₄ |
| 186 | 3-CH₃-4-Cl—C₆H₃ | 1 | 0 | 0 | 2-CH₃-benzimidazol-5-yl |
| 187 | 3-CH₃-4-Cl—C₆H₃ | 1 | 0 | 1 | (4-methyl-3-oxo-3,4-dihydro-2H-benzo[b][1,4]thiazinyl) |
| 188 | 3-CH₃-4-Cl—C₆H₃ | 1 | 0 | 0 | 1-CH₃-indol-3-yl |
| 189 | 3-CH₃-4-Cl—C₆H₃ | 1 | 0 | 0 | (1-(2-fluorophenyl)cyclopentyl) |
| 190 | 3-CH₃-4-Cl—C₆H₃ | 1 | 0 | 0 | 1-tert-butyl-3-CH₃-pyrazol-5-yl |

TABLE IV-continued (If)

[Structure: R¹—O—(piperidine with ()ₜ)—N—(piperidine)—N—C(=O)—(N)ₛ—(CH₂)ₙ—R³, with H on N]

| Compound | R¹ | t | s | n | R³ |
|---|---|---|---|---|---|
| 191 | 3-CH₃-4-Cl—C₆H₃ | 1 | 0 | 0 | 6-methyl-4-methyl-2H-benzo[b][1,4]thiazin-3(4H)-one-yl |
| 192 | 3-CH₃-4-Cl—C₆H₃ | 1 | 0 | 0 | 2-CH₃O-5-F—C₆H₃ |
| 193 | 3-CH₃-4-Cl—C₆H₃ | 1 | 0 | 0 | 3-NH₂-4-CH₃O—C₆H₃ |
| 194 | 3-CH₃-4-Cl—C₆H₃ | 1 | 0 | 0 | 2,5-(CH₃O)₂—C₆H₃ |
| 195 | 2-CH₃-4-Cl—C₆H₃ | 1 | 0 | 0 | 2-CN—C₆H₄ |
| 196 | 2-CH₃-4-Cl—C₆H₃ | 1 | 0 | 0 | 2-CH₃O-4-F—C₆H₃ |
| 197 | 3-CH₃-4-Cl—C₆H₃ | 1 | 0 | 0 | 1-CH₃-pyrrol-2-yl |
| 198 | 2-CH₃-4-Cl—C₆H₃ | 1 | 0 | 0 | 3-S(O)₂CH₃-4-NH₂—C₆H₃ |
| 199 | 2-CH₃-4-Cl—C₆H₃ | 1 | 0 | 0 | 1H-5-indol-2-yl |
| 200 | 3-CH₃-4-Cl—C₆H₃ | 1 | 0 | 0 | 1H-5-CH₃O-indol-3-yl |
| 201 | 2-CH₃-4-Cl—C₆H₃ | 1 | 0 | 0 | 3-F-4-CH₃—C₆H₃ |
| 202 | 2-CH₃-4-Cl—C₆H₃ | 1 | 0 | 0 | 1-phenyl-5-CH₃-pyrazol-4-yl |
| 203 | 2-CH₃-4-Cl—C₆H₃ | 1 | 0 | 0 | 2-(2-phenyl-thiazol-4-yl)-phenyl |
| 204 | 3-CH₃-4-Cl—C₆H₃ | 1 | 0 | 0 | 1H-5-F-indol-2-yl |
| 205 | 3-CH₃-4-Cl—C₆H₃ | 1 | 0 | 0 | 3-CF₃O-4-NH₂—C₆H₃ |
| 206 | 3-CH₃-4-Cl—C₆H₃ | 1 | 0 | 0 | 3-iso-propoxy-4-CH₃O—C₆H₃ |
| 207 | 2-CH₃-4-Cl—C₆H₃ | 1 | 0 | 0 | 1H-5-CH₃O-indol-2-yl |
| 208 | 2-CH₃-4-Cl—C₆H₃ | 1 | 0 | 0 | 1H-indol-4-yl |
| 209 | 2-CH₃-4-Cl—C₆H₃ | 1 | 0 | 0 | 4-CF₃-pyridin-3-yl |
| 210 | 2-CH₃-4-Cl—C₆H₃ | 1 | 0 | 0 | 1,3-dimethyl-5-methyl-4-(isopropylthio)-1H-pyrazolo[3,4-b]pyridin-yl |
| 211 | 2-CH₃-4-Cl—C₆H₃ | 1 | 0 | 0 | 1-CH₃-indol-3-yl |
| 212 | 2-CH₃-4-Cl—C₆H₃ | 1 | 0 | 0 | 3-iso-propoxy-4-CH₃O—C₆H₃ |
| 213 | 3-CH₃-4-Cl—C₆H₃ | 1 | 0 | 1 | 1H-indol-3-yl |
| 214 | 2-CH₃-4-Cl—C₆H₃ | 1 | 0 | 0 | 6-methyl-4-methyl-2H-benzo[b][1,4]thiazin-3(4H)-one-yl |
| 215 | 2-CH₃-4-Cl—C₆H₃ | 1 | 0 | 0 | 1-CH₃-indol-2-yl |
| 216 | 3-CH₃-4-Cl—C₆H₃ | 1 | 0 | 0 | 3-S(O)₂NH₂-4-Cl—C₆H₃ |
| 217 | 3-CH₃-4-Cl—C₆H₃ | 1 | 0 | 0 | 1-cyclopropyl-2,3-dimethyl-5-methoxy-indolin-yl |
| 218 | 3-CH₃-4-Cl—C₆H₃ | 1 | 0 | 0 | 3-(pyrrol-1-yl)-3-CN-thien-2-yl |
| 219 | 2-CH₃-4-Cl—C₆H₃ | 1 | 0 | 0 | 4-(pyrrol-1-yl)phenyl |
| 220 | 3-CH₃-4-Cl—C₆H₃ | 1 | 0 | 0 | 1H-indazol-3-yl |
| 221 | 2-CH₃-4-Cl—C₆H₃ | 1 | 0 | 0 | 3-CH₃O—NH₂—C₆H₃ |

TABLE IV-continued (If)

R¹—O—[piperidine]—N—[piperidine]—N(H)—(N)ₛ—(CH₂)ₙ—R³ with C(=O) linker and (—)ₜ

| Compound | R¹ | t | s | n | R³ |
|---|---|---|---|---|---|
| 221 | 2-CH₃-4-Cl—C₆H₃ | 1 | 0 | 0 | 1-CH₃-indol-2-yl |
| 223 | 3-CH₃-4-Cl—C₆H₃ | 1 | 0 | 0 | (1-methyl-1-phenylcyclopropyl) |
| 224 | 2-CH₃-4-Cl—C₆H₃ | 1 | 0 | 0 | 4-S(O)₂CH₃—C₆H₄ |
| 225 | 3-CH₃-4-Cl—C₆H₃ | 1 | 0 | 0 | 2-(1-CH₃-5-CF₃-pyrazol-3-yl)-thien-5-yl |
| 226 | 2-CH₃-4-Cl—C₆H₃ | 1 | 0 | 0 | 2-CH₃-5-F—C₆H₃ |
| 227 | 2-CH₃-4-Cl—C₆H₃ | 1 | 0 | 0 | 4-CH₂S(O)₂CH₃—C₆H₄ |
| 228 | 2-CH₃-4-Cl—C₆H₃ | 1 | 0 | 0 | Quinoxalin-2-yl |
| 229 | 2-CH₃-4-Cl—C₆H₃ | 1 | 0 | 0 | 1H-5-Cl-indol-2-yl |
| 230 | 3-CH₃-4-Cl—C₆H₃ | 1 | 0 | 0 | 3-CH₂S(O)₂CH₃—C₆H₄ |
| 231 | 2-CH₃-4-Cl—C₆H₃ | 1 | 0 | 1 | 2-(2,4-F₂—C₆H₃)thiazol-4-yl |
| 232 | 2-CH₃-4-Cl—C₆H₃ | 1 | 0 | 0 | 3-S(O)₂NH₂—C₆H₄ |
| 233 | 2-CH₃-4-Cl—C₆H₃ | 1 | 0 | 1 | 1H-indol-3-yl |
| 234 | 3-CH₃-4-Cl—C₆H₃ | 1 | 0 | 0 | 4-S(O)₂CH₃—C₆H₄ |
| 235 | 3-CH₃-4-Cl—C₆H₃ | 1 | 0 | 0 | 1-CH₃-indol-2-yl |
| 236 | 2-CH₃-4-Cl—C₆H₃ | 1 | 0 | 0 | 3-CH₃-5-CF₃-isoxazol-4-yl |
| 237 | 3-CH₃-4-Cl—C₆H₃ | 1 | 0 | 0 | 1-CH₃-indol-2-yl |
| 238 | 4-S(O)₂CH₃—C₆H₄ | 1 | 0 | 0 | 3,4-Cl₂—C₆H₃ |
| 239 | 2-CH₃-4-Cl—C₆H₃ | 1 | 0 | 0 | 1-CH₃-indol-3-yl |
| 240 | 3-CH₃-4-Cl—C₆H₃ | 1 | 0 | 0 | [1,8]-naphthyridin-2-yl |
| 241 | 2-CH₃-4-Cl—C₆H₃ | 1 | 0 | 0 | 3-S(O)₂CH₃—C₆H₄ |
| 242 | 3-CH₃-4-Cl—C₆H₃ | 1 | 0 | 0 | 3-OH—C₆H₄ |
| 243 | 3-CH₃-4-Cl—C₆H₃ | 1 | 0 | 0 | 3H-Benzthiazol-2-one-6-yl |
| 244 | 2-CH₃-4-Cl—C₆H₃ | 1 | 0 | 0 | 3-n-propoxy-pyridin-2-yl |
| 245 | 2-CH₃-4-Cl—C₆H₃ | 1 | 0 | 0 | 3H-Benzthiazol-2-one-6-yl |
| 246 | 2-CH₃-4-Cl—C₆H₃ | 1 | 0 | 0 | isoxazol-5-yl |
| 247 | 2-CH₃-4-Cl—C₆H₃ | 1 | 0 | 0 | 2,5-(CH₃O)₂—C₆H₃ |
| 248 | 2-CH₃-4-Cl—C₆H₃ | 1 | 0 | 0 | 1H-pyrazol-4-yl |
| 249 | 3-CH₃-4-Cl—C₆H₃ | 1 | 0 | 0 | Benzothiazol-6-yl |
| 250 | 2-CH₃-4-Cl—C₆H₃ | 1 | 0 | 0 | 3,5-(CH₃)₂-isoxazol-4-yl |
| 251 | 3-CH₃-4-Cl—C₆H₃ | 1 | 0 | 0 | 4-CF₃-pyridin-3-yl |
| 252 | 3-CH₃-4-Cl—C₆H₃ | 1 | 0 | 0 | 1H-indol-4-yl |
| 253 | 3-CH₃-4-Cl—C₆H₃ | 1 | 0 | 0 | 1,5-(CH₃)₂-pyrazol-3-yl |
| 254 | 2-CH₃-4-Cl—C₆H₃ | 1 | 0 | 0 | 1H-indazol-3-yl |
| 255 | 3-CH₃-4-Cl—C₆H₃ | 1 | 0 | 0 | 3-S(O)₂NH₂—C₆H₄ |
| 256 | 2-CH₃-4-Cl—C₆H₃ | 1 | 0 | 1 | 4-S(O)₂CH₃—C₆H₄ |
| 257 | 2-CH₃-4-Cl—C₆H₃ | 1 | 0 | 0 | Benzthiazol-6-yl |
| 258 | 2-CH₃-4-Cl—C₆H₃ | 1 | 0 | 0 | 1H-5-OH-indol-2-yl |
| 259 | 2-CH₃-4-Cl—C₆H₃ | 1 | 0 | 0 | 3-CH₂S(O)₂CH₃—C₆H₄ |
| 260 | 2-CH₃-4-Cl—C₆H₃ | 1 | 0 | 0 | 3,4-methylenedioxyphenyl |
| 261 | 2-CH₃-4-Cl—C₆H₃ | 1 | 0 | 0 | 1-CH₃-pyrrol-2-yl |
| 262 | 2-CH₃-4-Cl—C₆H₃ | 1 | 0 | 0 | 3-CH₃-4-NH₂—C₆H₃ |
| 263 | 3-CH₃-4-Cl—C₆H₃ | 1 | 0 | 0 | Isoxazol-5-yl |
| 264 | 2-CH₃-4-Cl—C₆H₃ | 1 | 0 | 0 | 3-OH—C₆H₄ |
| 265 | 2-CH₃-4-Cl—C₆H₃ | 1 | 0 | 0 | 1H-5-OH-indol-3-yl |
| 266 | 3-CH₃-4-Cl—C₆H₃ | 1 | 0 | 0 | (4-methyl-1(2H)-isoquinolinon-yl) |
| 267 | 2-CH₃-4-Cl—C₆H₃ | 1 | 0 | 0 | (2-methylimidazo[1,2-a]pyridin-yl) |

TABLE IV-continued

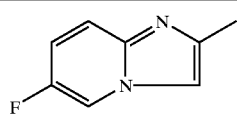

(If)

| Compound | R¹ | t | s | n | R³ |
|---|---|---|---|---|---|
| 268 | 2-CH₃-4-Cl—C₆H₃ | 1 | 0 | 0 | 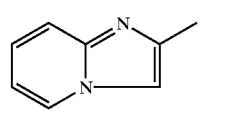 |
| 269 | 3-CH₃-4-Cl—C₆H₃ | 1 | 0 | 0 | 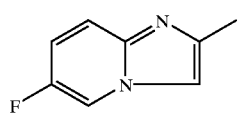 |
| 270 | 3-CH₃-4-Cl—C₆H₃ | 1 | 0 | 0 | 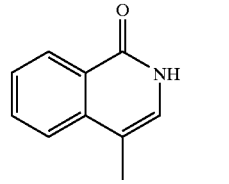 |
| 271 | 2-CH₃O-4-Cl—C₆H₃ | 1 | 0 | 0 | 3-CH₃S(O)₂—C₆H₄ |
| 272 | 2,6-(CH₃)₂-4-Cl—C₆H₂ | 1 | 0 | 0 | 3-CH₃S(O)₂—C₆H₄ |
| 273 | 2,3-Cl₂—C₆H₃ | 1 | 0 | 0 | 3-CH₃S(O)₂—C₆H₄ |
| 274 | 2,5-Cl₂—C₆H₃ | 1 | 0 | 0 | 3-CH₃S(O)₂—C₆H₄ |
| 275 | 2-Cl-4-CH₃—C₆H₃ | 1 | 0 | 0 | 3-CH₃S(O)₂—C₆H₄ |
| 276 | 2-Cl-5-CH₃—C₆H₃ | 1 | 0 | 0 | 3-CH₃S(O)₂—C₆H₄ |
| 277 | 2-CH₃-4-C(O)CH₃—C₆H₃ | 1 | 0 | 0 | 3-CH₃S(O)₂—C₆H₄ |
| 278 | 2-(morpholin-4-yl)-C₆H₄ | 1 | 0 | 0 | 3-CH₃S(O)₂—C₆H₄ |
| 279 | 3-CH₃CH₂-4-Cl—C₆H₃ | 1 | 0 | 0 | 3-CH₃S(O)₂—C₆H₄ |
| 280 | Naphth-7-yl | 1 | 0 | 0 | 3-HC₃S(O)₂—C₆H₄ |
| 281 | 2-tert-butyl-C₆H₄ | 1 | 0 | 0 | 3-CH₃S(O)₂—C₆H₄ |
| 282 | Indan-5-yl | 1 | 0 | 0 | 3-CH₃S(O)₂—C₆H₄ |
| 283 | 2-cyclohexyl-4-Cl—C₆H₄ | 1 | 0 | 0 | 3-CH₃S(O)₂—C₆H₄ |
| 284 | 2-C(O)NH₂-4-Cl—C₆H₃ | 1 | 0 | 0 | 3-CH₃S(O)₂—C₆H₄ |
| 285 | 2-isoxazol-5-yl-4-Cl—C₆H₄ | 1 | 0 | 0 | 3-CH₃S(O)₂—C₆H₄ |
| 286 | 2-CH₃-5-Cl—C₆H₃ | 1 | 0 | 0 | 3-CH₃S(O)₂—C₆H₄ |
| 287 | phenyl | 1 | 0 | 0 | 3-CH₃S(O)₂—C₆H₄ |
| 288 | 2,4-Cl₂-6-CH₂—C₆H₂ | 1 | 0 | 0 | 3-CH₃S(O)₂—C₆H₄ |
| 289 | 3-Cl-4-CH₃—C₆H₃ | 1 | 0 | 0 | 3-CH₃S(O)₂—C₆H₄ |
| 290 | 2-CN-4-CH₃—C₆H₃ | 1 | 0 | 0 | 3-CH₃S(O)₂—C₆H₄ |
| 291 | 2-CN-4-CF₃—C₆H₃ | 1 | 0 | 0 | 3-CH₃S(O)₂—C₆H₄ |
| 292 | 2-CH₃-pyridin-6-yl | 1 | 0 | 0 | 3-CH₃S(O)₂—C₆H₄ |
| 293 | Pyrimidin-2-yl | 1 | 0 | 0 | 3-CH₃S(O)₂—C₆H₄ |
| 294 | 2-Cl-4-F—C₆H₃ | 1 | 0 | 0 | 2-Cl-4-CH₃S(O)₂—C₆H₃ |
| 295 | 2-CH₃-4-Cl—C₆H₃ | 1 | 0 | 0 | 2-CH₃S(O)₂—C₆H₄ |
| 296 | 2-CH₃-4-Cl—C₆H₃ | 1 | 0 | 0 | 2-Cl-4-CH₃S(O)₂—C₆H₃ |
| 297 | 2-CH₃-4-Cl—C₆H₃ | 1 | 0 | 0 | 3-S(O)₂NH₂-4-Cl—C₆H₃ |
| 298 | 2-CH₃-4-Cl—C₆H₃ | 1 | 0 | 0 | 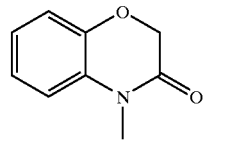 |
| 299 | 2,4-Cl₂-3-CH₃—C₆H₂ | 1 | 0 | 0 | 3-S(O)₂CH₃—C₆H₄ |
| 300 | 2-ethyl-4-F—C₆H₃ | 1 | 0 | 0 | 3-S(O)₂CH₃—C₆H₄ |
| 301 | 2-CH₃-4-Cl—C₆H₃ | 1 | 0 | 0 | 1H-5-S(O)₂CH₃-indol-2-yl |
| 302 | 2-CH₃-4-Cl—C₆H₃ | 1 | 0 | 1 |  |

TABLE IV-continued (If)

![Structure for formula If]

| Compound | R¹ | t | s | n | R³ |
|---|---|---|---|---|---|
| 303 | 3-CH₃-4-Cl—C₆H₃ | 1 | 0 | 1 | [benzoxazinone structure] |
| 304 | 2,4-Cl₂-3-CH₃—C₆H₂ | 1 | 0 | 0 | [fluoro-imidazopyridine structure] |
| 305 | 2,4-Cl₂-3-CH₃—C₆H₂ | 1 | 0 | 0 | 2-(pyrazol-1-yl)-pyridin-5-yl |
| 306 | 2,4-Cl₂-3-CH₃—C₆H₂ | 1 | 0 | 0 | 2-S(O)₂CH₃-thien-5-yl |
| 307 | 2,4-Cl₂-3-CH₃—C₆H₂ | 1 | 0 | 0 | 4-S(O)₂CH₃—C₆H₄ |
| 308 | 5-CF₃-pyridin-2-yl | 1 | 0 | 0 | 3-S(O)₂CH₃—C₆H₄ |
| 309 | 3,4-Cl₂—C₆H₃ | 1 | 1 | 0 | phenyl |
| 310 | 3,4-Cl₂—C₆H₃ | 1 | 1 | 0 | 4-OCH₃—C₆H₄ |
| 311 | 3,4-Cl₂—C₆H₃ | 1 | 1 | 0 | 4-F—C₆H₄ |
| 312 | 3,4-Cl₂—C₆H₃ | 1 | 1 | 0 | 3-SCH₃—C₆H₄ |
| 313 | 3,4-Cl₂—C₆H₃ | 1 | 1 | 1 | phenyl |
| 314 | 3,4-Cl₂—C₆H₃ | 1 | 1 | 1 | 4-OCH₃—C₆H₄ |
| 315 | 3,4-Cl₂—C₆H₃ | 1 | 1 | 1 | 4-F—C₆H₄ |

Examples of compounds of formula (Ig) are listed in Table V below.

TABLE V

| | R¹ | X | R³ |
|---|---|---|---|
| 1 | 3,4-Cl₂—C₆H₃ | CH₂ | 3-S(O)₂CH₃—C₆H₄ |
| 2 | 3,4-Cl₂—C₆H₃ | NH | 3-S(O)₂CH₃—C₆H₄ |
| 3 | 3,4-Cl₂—C₆H₃ | C(O) | 3-S(O)₂CH₃—C₆H₄ |
| 4 | 3,4-Cl₂—C₆H₃ | S(O)₂ | 4-S(O)₂CH₃—C₆H₄ |
| 5 | 3,4-Cl₂—C₆H₃ | S(O)₂ | C₆H₅ |

The compounds of formula (I):

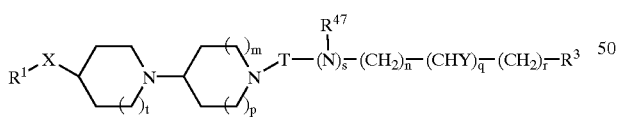

(I)

wherein:

q, s and t are, independently, 0 or 1;
n and r are, independently, 0, 1, 2, 3, 4 or 5;
m and p are, independently, 0, 1 or 2;
X is $CH_2$, $C(O)$, O, S, $S(O)$, $S(O)_2$ or $NR^{37}$;
Y is $NHR^2$ or OH;
T is $C(O)$, $C(S)$, $S(O)_2$ or $CH_2$;
$R^1$ is hydrogen, $C_{1-6}$ alkyl, aryl or heterocyclyl;
$R^2$ and $R^{47}$ are, independently, hydrogen, $C_{1-6}$ alkyl, aryl($C_{1-4}$)alkyl or $CO(C_{1-6}$ alkyl);
$R^3$ is $C_{1-6}$ alkyl {optionally substituted by halogen, $CO_2R^4$ or phthalimide}, $CR^{3a}R^{3b}R^{3c}$, $C_{2-4}$ alkenyl {optionally substituted by aryl or heterocyclyl}, $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl, heterocyclyl, thioaryl or thioheterocyclyl;

$R^{3a}$ is hydrogen, $C_{1-6}$ alkyl, $C_{1-6}$ alkoxy or $C_{3-7}$ cycloalkyl; $R^{3b}$ is aryl, heterocyclyl, $S(O)_2$aryl or $S(O)_2$heterocyclyl; and $R^{3c}$ is $C_{1-6}$ alkyl, $C_{1-4}$ haloalkyl, hydroxy, heterocyclyl($C_{1-4}$ alkyl) or aryl;

wherein, unless stated otherwise, the foregoing aryl and heterocyclyl moieties are optionally substituted by: halogen, OH, SH, $NO_2$, oxo, $C_{1-6}$ alkyl {itself optionally substituted by halogen, $OC(O)C_{1-6}$ alkyl, $S(O)_2R^{48}$, phenyl (itself optionally substituted by halogen (such as one or two chlorine or fluorine atoms), $C_{1-6}$ alkyl, $S(O)_2R^{38}$ or $C(O)NR^{39}R^{40}$), naphthyloxy (itself optionally substituted by halo or $C_{2-6}$ alkenyl), $C_{3-10}$ cycloalkyl (itself optionally substituted by $C_{1-4}$ alkyl or oxo) or $NR^{41}C(O)OCH_2$(fluoren-9-yl)}, $NR^{41}C(O)OCH_2$(fluoren-9-yl), $C_{1-6}$ alkoxy {itself optionally substituted by halogen, $C_{1-6}$ alkoxy, $NHCO_2(C_{1-6}$ alkyl), $CO_2R^4$, $NR^5R^6$ or phenyl (itself optionally substituted by halogen or $NO_2$)}, $C_{1-6}$ alkylthio, $C_{1-6}$ haloalkylthio, $C_{3-10}$ cycloalkyl, $NR^7R^8$, $NR^9C(O)R^{10}$, $CO_2R^{11}$, $C(O)NR^{12}R^{13}$, $C(O)R^{14}$, $S(O)_dR^{15}$, $S(O)_2NR^{42}R^{43}$, $NR^{44}S(O)_2R^{45}$, phenyl {itself optionally substituted by halogen, $C_{1-6}$ alkyl, $C_{1-6}$ haloalkyl, CN, $NO_2$, $C_{1-6}$ alkoxy (itself optionally substituted by halogen, OH or pyridinyl), phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, heterocyclyl {itself optionally substituted by halogen, $C_{1-6}$ alkyl, $C_{1-6}$ haloalkyl, CN, $NO_2$, $C_{1-6}$ alkoxy, $C_{1-6}$ haloalkoxy, phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, phenoxy {itself optionally substituted by halogen, $C_{1-6}$ alkyl, $C_{1-6}$ haloalkyl, CN, $NO_2$, $C_{1-6}$ alkoxy, $C_{1-6}$ haloalkoxy, phenyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy)}, SCN, CN, $SO_3H$ (or an alkali metal salt thereof), methylenedioxy or difluoromethylenedioxy; when aryl is phenyl adjacent substituents may join to form, together with the phenyl ring to which they are attached, a dihydrophenanthrene moiety;

d is 0, 1 or 2;

$R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl, aryl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy);

$R^{15}$, $R^{38}$, $R^{45}$ and $R^{48}$ are, independently, $C_{1-6}$ alkyl (optionally substituted by halogen, hydroxy or $C_{3-10}$ cycloalkyl), $C_{3-6}$ alkenyl, aryl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy) or heterocyclyl (itself optionally substituted by halogen, $C_{1-6}$ alkyl, $C_{1-6}$ haloalkyl, CN, $NO_2$, $C_{1-6}$ alkoxy or $C_{1-6}$ haloalkoxy);

or an N-oxide thereof; or a pharmaceutically acceptable salt thereof; or a solvate thereof; have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

In one aspect examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behçet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

In another aspect examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle.

In a further aspect examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle.

The compounds of formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, are also H1 antagonists and may be used in the treatment of allergic disorders.

The compounds of formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, may also be used to control a sign and/or symptom of what is commonly referred to as a cold (for example a sign and/or symptom of a common cold or influenza or other associated respiratory virus infection).

Thus, in a further aspect the present invention provides a compound of formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, which is both a modulator of chemokine receptor (especially CCR3) activity and an H1 antagonist.

According to a further feature of the invention there is provided a compound of the formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity) in a warm blooded animal, such as man, in need of such treatment, which comprises administering to said animal an effective amount of a compound of the formula (I) (as defined anywhere herein), (I'), (Ia"), (Ia), (Ia'), (Ib), (Ic), (Id), (Ie), (If) or (Ig) or a pharmaceutically acceptable salt thereof or a solvate thereof.

According to another feature of the present invention there is provided a method for antagonising H1 in a warm blooded animal, such as man, in need of such treatment, which comprises administering to said animal an effective amount of a compound of the formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof.

The invention also provides a compound of the formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, for use as a medicament.

In another aspect the invention provides the use of a compound of formula (I) (as defined anywhere herein), (I'), (Ia"), (Ia), (Ia'), (Ib), (Ic), (Id), (Ie), (If) or (Ig), or a pharmaceutically acceptable salt thereof or a solvate thereof, in the manufacture of a medicament for use in therapy (for example modulating chemokine receptor activity (especially CCR3 receptor activity) or antagonising H1 in a warm blooded animal, such as man, or both).

In a further aspect the present invention provides the use of a compound of the formula (I), wherein: q, s and t are, independently, 0 or 1; n and r are, independently, 0, 1, 2, 3, 4 or 5; m and p are, independently, 0, 1 or 2; X is $CH_2$, $C(O)$, O, S, $S(O)$, $S(O)_2$ or $NR^{37}$; Y is $NHR^2$ or OH; T is $C(O)$, $C(S)$, $S(O)_2$ or $CH_2$; $R^1$ is hydrogen, $C_{1-6}$ alkyl, aryl or heterocyclyl; $R^2$ and $R^{47}$ are, independently, hydrogen, $C_{1-6}$ alkyl, aryl($C_{1-4}$)alkyl or $CO(C_{1-6}$ alkyl); $R^3$ is $C_{1-6}$ alkyl {optionally substituted by halogen, $CO_2R^4$ or phthalimide}, $C_{3-7}$ cycloalkyl {optionally substituted by $C_{1-4}$ alkyl or oxo}, $C_{3-7}$ cycloalkenyl {optionally substituted by oxo, $C_{1-6}$ alkyl or aryl}, aryl or heterocyclyl; wherein, unless stated otherwise, the foregoing aryl and heterocyclyl moieties are optionally substituted by: halogen, OH, SH, $NO_2$, oxo, $C_{1-6}$ alkyl (itself optionally substituted by halogen, $OC(O)C_{1-6}$ alkyl, $S(O)_2R^{48}$, phenyl (itself optionally substituted by halo (such as one or two chlorine or fluorine atoms), $C_{1-6}$ alkyl, $S(O)_2R^{38}$ or $C(O)NR^{39}R^{40}$), naphthyloxy (itself optionally substituted by halo or $C_{2-6}$ alkenyl), $C_{3-10}$ cycloalkyl (itself optionally substituted by $C_{1-4}$ alkyl or oxo) or $NR^{41}C(O)OCH_2$(fluoren-9-yl)), $NR^{41}(O)OCH_2$(fluoren-9-yl), $C_{1-6}$ alkoxy (itself optionally substituted by halogen, $C_{1-6}$ alkoxy, $NHCO_2(C_{1-6}$ alkyl), $CO_2R^4$, $NR^5R^6$ or phenyl (itself optionally substituted by halogen or $NO_2$)), $C_{1-6}$ alkylthio, $C_{1-6}$ haloalkylthio, $C_{3-10}$ cycloalkyl, $NR^7R^8$, $NR^9C(O)R^{10}$, $CO_2R^{11}$, $C(O)NR^{12}R^{13}$, $C(O)R^{14}$, $S(O)_dR^{15}$, $S(O)_2NR^{42}R^{43}$, $NR^{44}S(O)_2R^{45}$, phenyl (itself optionally substituted by halo, $C_{1-6}$ alkyl, $C_{1-6}$ haloalkyl, CN, $NO_2$ or $C_{1-6}$ alkoxy (itself optionally substituted by halo, OH or pyridinyl)), heterocyclyl (itself optionally substituted by halo, $C_{1-6}$ alkyl, $C_{1-6}$ haloalkyl, CN, $NO_2$, $C_{1-6}$ alkoxy or $C_{1-6}$ haloalkoxy), phenoxy (itself optionally substituted by halo, $C_{1-6}$ alkyl, $C_{1-6}$ haloalkyl, CN, $NO_2$, $C_{1-6}$ alkoxy or $C_{1-6}$ haloalkoxy), SCN, CN, $SO_3H$ (or an alkali metal salt thereof) or methylenedioxy; when aryl is phenyl adjacent substituents may join to form, together with the phenyl ring to which they are attached, a dihydrophenanthrene moiety; d is 0, 1 or 2; $R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); $R^{15}$, $R^{38}$, $R^{45}$ and $R^{48}$ are, independently, $C_{1-6}$ alkyl (optionally substituted by halogen, hydroxy or $C_{3-10}$ cycloalkyl) or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); or a pharmaceutically acceptable salt thereof; or a solvate thereof; in the manufacture of a medicament for use in therapy (for example modulating chemokine receptor activity (especially CCR3 receptor activity) or antagonising H1 in a warm blooded animal, such as man, or both).

In another aspect the present invention provides the use of a compound of the formula (I'):

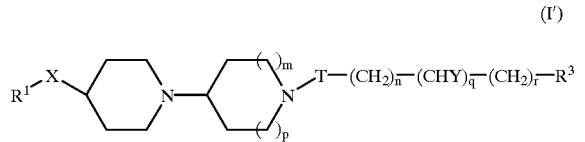

(I')

wherein: q is 0 or 1; n and r are, independently, 0, 1, 2, 3, 4 or 5; m and p are, independently, 0, 1 or 2; X is $CH_2$, CO, O, S, S(O), $S(O)_2$ or $NR^{37}$; Y is $NHR^2$ or OH; T is CO, CS, $SO_2$ or $CH_2$; $R^1$ is hydrogen, $C_{1-6}$ alkyl, aryl or heterocyclyl; $R^2$ is hydrogen, $C_{1-6}$ alkyl, aryl($C_{1-4}$)alkyl or $CO(C_{1-6}$ alkyl); $R^3$ is $C_{1-6}$ alkyl {optionally substituted by halogen, $CO_2R^4$ or phthalimide}, $C_{3-7}$ cycloalkyl {optionally substituted by $C_{1-4}$ alkyl or oxo}, $C_{3-7}$ cycloalkenyl {optionally substituted by $C_{1-6}$ alkyl or aryl}, aryl or heterocyclyl; wherein, unless stated otherwise, the foregoing aryl and heterocyclyl moieties are optionally substituted by: halogen, OH, SH, $NO_2$, oxo, $C_{1-6}$ alkyl (itself optionally substituted by halogen, $OC(O)C_{1-6}$ alkyl, phenyl (itself optionally substituted by halo (such as one or two chlorine or fluorine atoms), $C_{1-6}$ alkyl, $SO_2R^{38}$ or $CONR^{39}R^{40}$), naphthyloxy (itself optionally substituted by halo or $C_{2-6}$ alkenyl) or $NR^4C(O)OCH_2$(fluoren-9-yl)), $NR^{41}C(O)OCH_2$(fluoren-9-yl), $C_{1-6}$ alkoxy (itself optionally substituted by halogen, $CO_2R^4$, $NR^5R^6$ or phenyl (itself optionally substituted by halogen or $NO_2$)), $C_{1-6}$ alkylthio, nitro, $C_{3-7}$ cycloalkyl, $NR^7R^8$, $NR^9COR^{10}$, $CO_2R^{11}$, $CONR^{12}R^{13}$, $COR^{14}$, $SO_dR^{15}$, $SO_2NR^{42}R^{43}$, $NR^{44}SO_2R^{45}$, phenyl (itself optionally substituted by halo, $C_{1-6}$ alkyl, $C_{1-6}$ haloalkyl, CN, $NO_2$ or $C_{1-6}$ alkoxy (itself optionally substituted by halo, OH or pyridinyl)), heterocyclyl (itself optionally substituted by halo, $C_{1-6}$ alkyl, $C_{1-6}$ haloalkyl, CN, $NO_2$, $C_{1-6}$ alkoxy or $C_{1-6}$ haloalkoxy), phenoxy (itself optionally substituted by halo, $C_{1-6}$ alkyl, $C_{1-6}$ haloalkyl, CN, $NO_2$, $C_{1-6}$ alkoxy or $C_{1-6}$ haloalkoxy), SCN, CN, $SO_3H$ (or an alkali metal salt thereof) or methylenedioxy; when aryl is phenyl adjacent substituents may join to form, together with the phenyl ring to which they are attached, a dihydrophenanthrene moiety; d is 0, 1 or 2; $R^4$, $R^5$, $R^6$, $R^7$, $R^8$, $R^9$, $R^{10}$, $R^{11}$, $R^{12}$, $R^{13}$, $R^{14}$, $R^{37}$, $R^{39}$, $R^{40}$, $R^{41}$, $R^{42}$, $R^{43}$ and $R^{44}$ are, independently, hydrogen, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); $R^{15}$, $R^{38}$ and $R^{45}$ are, independently, $C_{1-6}$ alkyl or aryl (itself optionally substituted by halo, $C_{1-6}$ alkyl, $C_{1-6}$ haloalkyl, CN, $NO_2$, $C_{1-6}$ alkoxy or $C_{1-6}$ haloalkoxy); or a pharmaceutically acceptable salt thereof; or a solvate thereof; in the manufacture of a medicament for use in therapy (for example modulating chemokine receptor activity (especially CCR3 receptor activity) in a warm blooded animal, such as man).

The invention further provides the use of a compound of formula (I) (as defined anywhere above), (I'), (Ia"), (Ia), (Ia'), (Ib), (Ic), (Id), (Ie), (If) or (Ig), or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a warm blooded animal, such as man.

In a further aspect a compound of formula (I) (as defined anywhere above), (I'), (Ia"), (Ia), (Ia'), (Ib), (Ic), (Id), (Ie), (If) or (Ig), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I) (as defined anywhere above), (I'), (Ia"), (Ia), (Ia'), (Ib), (Ic), (Id), (Ie), (If) or (Ig), or a pharmaceutically acceptable salt thereof, is useful in the treatment of asthma.

The invention also provides the use of a compound of formula (I) (as defined anywhere above), (I'), (Ia"), (Ia), (Ia'), (Ib), (Ic), (Id), (Ie), (If) or (Ig), or a pharmaceutically acceptable salt thereof, in the manufacture of a medicament for use in the treatment of a sign and/or symptom of what is commonly referred to as a cold (for example a sign and/or symptom of common cold or influenza or other associated respiratory virus infection).

The present invention also provides a the use of a compound of formula (I) (as defined anywhere above), (I'), (Ia"), (Ia), (Ia'), (Ib), (Ic), (Id), (Ie), (If) or (Ig), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) or an H1 mediated disease state (such as an allergic disorder) in a warm blooded animal, such as man, which comprises administering to a mammal in need of such treatment an effective amount of a compound of formula (I), (I'), (Ia"), (Ia), (Ia'), (Ib), (Ic), (Id), (Ie), (If) or (Ig), or a pharmaceutically acceptable salt thereof or solvate thereof.

The present invention also provides a method of treating a sign and/or symptom of a cold (for example a sign and/or symptom of common cold or influenza or other associated respiratory virus infection) in a warm blooded animal, such as man, which comprises administering to a mammal in need of such treatment an effective amount of a compound of formula (I), (I'), (Ia"), (Ia), (Ia'), (Ib), (Ic), (Id), (Ie), (If) or (Ig), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I), (I'), (Ia"), (Ia), (Ia'), (Ib), (Ic), (Id), (Ie), (If) or (Ig), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity, said ingredient is normally formulated in accordance with standard pharmaceutical practice as a pharmaceutical composition.

Therefore in another aspect the present invention provides a pharmaceutical composition which comprises a compound of the formula (I), (I'), (Ia"), (Ia), (Ia'), (Ib), (Ic), (Id), (Ie), (If) or (Ig), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 $mgkg^{-1}$ to 100 $mgkg^{-1}$ of the compound, preferably in the range of 0.1 $mgkg^{-1}$ to 20 $mgkg^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), (I'), (Ia"), (Ia), (Ia'), (Ib), (Ic), (Id), (Ie), (If) or (Ig), or a pharmaceutically-acceptable salt thereof (hereafter Compound X), for therapeutic or prophylactic use in humans:

| (a) | |
|---|---|
| Tablet I | mg/tablet |
| Compound X | 100 |
| Lactose Ph. Eur. | 179 |
| Croscarmellose sodium | 12.0 |

-continued (a)

| Tablet I | mg/tablet |
|---|---|
| Polyvinylpyrrolidone | 6 |
| Magnesium stearate | 3.0 |

(b)

| Tablet II | mg/tablet |
|---|---|
| Compound X | 50 |
| Lactose Ph. Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1.0 |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limiting examples in which, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 (CD$_3$SOCD$_3$) or CDCl$_3$ as the solvent unless otherwise stated;

(ii) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the positive mass ion –(M+H)$^+$;

(iii) the title and sub-titled compounds of the examples and methods were named using the AUTONOM program from Beilstein informationssysteme GmbH;

(iv) unless stated otherwise, reverse phase HPLC was conducted using a Symmetry, NovaPak or Ex-Terra reverse phase silica column; and (v) the following abbreviations are used:

| RPHPLG | reverse phase HPLC |
|---|---|
| RT | room temperature |
| DEAD | diethyl-azodicarboxylate |
| NMP | N-methylpyrrolidone |
| CDI | N,N'-carbonyl diimidazole |
| MTBE | tert-butyl methyl ether |
| DMF | N,N-dimethylformamide |
| Boc or BOC | tert-butoxycarbonyl |
| HPLC | high pressure liquid chromatography |
| PYBROP ™ | bromo-tris-pyrrolidino-phosphonium hexafluorophosphate |
| THF | tetrahydrofuran |
| DCM | dichloromethane |
| TFA | trifluoroacetic acid |
| m. pt. | melting point |
| DMSO | dimethylsulfoxide |
| Ac | Acetate |
| aq | aqueous |
| IPA | iso-propyl alcohol |
| equiv. | equivalents |

EXAMPLE 1

This Example illustrates the preparation of 4-(3,4-dichlorophenoxy)piperidine.

Step a: tert-Butyl 4-(3,4-dichlorophenoxy)-1-piperidinecarboxylate

Diethyl azodicarboxylate (41.0 ml) was added to a solution of triphenylphosphine (62.9 g) in tetrahydrofuran (800 ml) at 0° C. After 15 minutes 3,4-dichlorophenol (39.1 g) was added, after a further 15 minutes tert-butyl 4-hydroxy-1-piperidinecarboxylate (48.3 g) in tetrahydrofuran (400 ml) was added dropwise over 30 min. The solution was stirred at room temperature for 16 hours and concentrated to a small volume. Purification by chromatography (ethyl acetate: isohexane 95:5) gave the sub-title compound as an oil (61.3 g).

MS: APCI(+ve): 246 (M-BOC+2H)

Step b: 4-(3,4-Dichlorophenoxy)piperidine

The product from Step a was dissolved in dichloromethane (600 ml) and trifluoroacetic acid (300 ml) was added. After 24 hours at room temperature the solution was evaporated and the resultant gum triturated under ether to give the sub-titled product as a solid (36.6 g). The free base was liberated by addition of aqueous NaOH (2M) and extraction with ethyl acetate followed by evaporation of solvent to give the title compound as a gum (25 g).

$^1$H NMR: δ(CDCl$_3$) 1.77 (1H, br s), 2.05–2.26 (4H, m), 3.20–3.49 (4H, m), 4.61 (1H, s), 6.69–7.52 (3H, m).

EXAMPLE 2

This Example illustrates the preparation of [4-(3,4-dichloro-phenoxy)-[1,4']bipiperidinyl-1'-yl]-(3- methanesulfonyl-phenyl)-methanone acetate (acetate salt of Compound 281 in Table I).

Step a: 4-(3,4-Dichloro-phenoxy)-[1,4']bipiperidinyl-1'-carboxylic acid tert-butyl ester 4-(3,4-Dichlorophenoxy)piperidine (1.5 g) was dissolved in 1,2-dichloroethane (21 ml). 1-Boc-4-piperidone was added (1.21 g) followed by NaBH(OAc)$_3$ (1.81 g) and acetic acid (0.37 g). After 18 hours at room temperature aqueous NaOH (1M) solution and diethyl ether were added. The product was extracted with diethyl ether, the combined organic extracts dried with MgSO$_4$ and concentrated. Purification by silica chromatography (dichloromethane:methanol 92:8) gave the sub-title product (1.97 g).

MS: APCI(+ve): 429 (M+H)

Step b: 4-(3,4-Dichloro-phenoxy)-[1,4']bipiperidine

The product of Step a was dissolved in dichloromethane (30 ml) and trifluoroacetic acid (15 ml) was added. After 4 hours at room temperature the solution was evaporated and the resultant gum triturated under ether to give the trifluoroacetate salt of the sub-titled product as a solid (1.15 g). The free base was liberated by addition of aqueous NaOH (2M) and extraction with ethyl acetate followed by evaporation of solvent to give the sub-title compound as a solid (0.68 g).

$^1$H NMR: δ(CDCl$_3$) 1.38–1.51 (2H, m), 1.74–2.02 (6H, m), 2.38–2.50 (3H, m), 2.56–2.61 (2H, m), 2.79–2.86 (2H, m), 3.14–3.18 (2H ,m), 4.22–4.28 (1H, m), 6.73–7.32 (3H, m).

Step c: [4-(3,4-Dichloro-phenoxy)-[1,4']bipiperidinyl-1'-yl]-(3-methanesulfonyl-phenyl)-methanone acetate The product of Step b (0.15 g) was dissolved in THF (4 ml), bromo-tris-pyrrolidino-phosphonium hexafluorophosphate (PYBROP™; 0.235 g), 3-methylsulphonylbenzoic acid (0.091 g) and N,N-di-iso-propylethylamine (0.238 ml) were added. After 18 hours at room temperature ethyl acetate and aqueous NaHCO$_3$ solution were added. The product was extracted with ethyl acetate, the combined organic extracts dried with Na$_2$SO$_4$ and concentrated. Purification by reverse phase HPLC (with a gradient eluent system (45% MeCN/NH$_4$OAc$_{aq}$ (0.1%) to 95% MeCN// NH$_4$OAc$_{aq}$ (0.1%)) gave the title compound (0.095 g).

$^1$H NMR: δ( DMSO-D6) 1.44–1.94 (8H, m), 2.37–2.77 (5H, m), 3.07–3.55 (6H, m), 4.40 (1H, m), 4.50–4.53 (1H, m), 6.96–8.02 (7H, m). Melting point: 60–61° C. becomes a gum. Melting point of free base: 154° C.

EXAMPLE 3

This Example illustrates the preparation of (4-amino-3-methoxy-phenyl)-[4-(3,4-dichlorophenoxy)-[1,4']bipiperidinyl-1'-yl]-methanone acetate (Compound 282 of Table I).

The compound was prepared by the method of Example 2, Step c using 4-amino-3-methoxybenzoic acid to give the title compound as a solid (0.016 g).

$^1$H NMR: δ(DMSO-D6) 1.32–2.01 (8H, m), 2.28–2.88 (5H, m), 3.32 (4H, br s), 3.77 (3H, s), 4.13 (2H, br s), 4.39–4.44 (1H, m), 6.59–7.50 (6H, m). Melting point: 171° C. becomes a gum.

EXAMPLE 4

This Example illustrates the preparation of (4-amino-3-methoxy-phenyl)- {3-[4-(3,4-difluoro-phenoxy)-piperidin-1-yl]-pyrrolidin-1-yl}-methanone (Compound 4 of Table II).

Step a: tert-Butyl 4-(3,4-difluorophenoxy)-1-piperidinecarboxylate

This compound was prepared according to the method of Example 1 Step a using 3,4-difluorophenol to afford the compound as an oil (5.4 g).

MS: ESI(+ve): 213 (M-BOC+H)

Step b: 4-(3,4-Difluorophenoxy)piperidine

This compound was prepared according to the method of Example 1 Step b to afford the compound as a pale yellow oil (3 g).

MS: ESI(+ve): 214 (+H)

Step c: 3-[4-(3,4-Difluoro-phenoxy)piperidin-1-yl]-pyrrolidine-1-carboxylic acid tert-butyl ester The product of Step b (0.5 g) was dissolved in 1,2-dichloroethane (7 ml). tert-Butyl 3-oxo-1-pyrrolidinecarboxylate (0.43 g) was added followed by NaBH(OAc)$_3$ (0.7 g) and acetic acid (0.08 g). After 24 hours at room temperature aqueous NaOH (1M) solution and diethyl ether were added. The product was extracted with diethyl ether, the combined organic extracts dried with MgSO$_4$ and concentrated. Purification by silica chromatography (100% ethyl acetate) gave the sub-title product (0.79 g).

MS: ESI(+ve): 383 (M+H)

Step d: 3,4-Difluorophenyl 1-(3-pyrrolidinyl)-4-piperidinyl ether

The product of Step c was dissolved in dioxane (10 ml) and HCl (6N) (10 ml) was added and the reaction stirred for 3 hrs. Organic solvent was evaporated and aqueous NaOH (2M) added. The product was extracted with ethyl acetate, the combined organic extracts dried with Na$_2$SO$_4$ and concentrated to give the sub-title product as an oil (0.54 g).

$^1$H NMR: δ(CDCl$_3$) 1.60–2.39 (9H, m), 2.70–3.13 (6H, m), 4.19–4.22 (1H, m), 6.58–7.52 (3H, m).

Step e: (4-Amino-3-methoxy-phenyl)-{3-[4-(3,4-difluoro-phenoxy)-piperidin-1-yl]-pyrrolidin-1-yl}-methanone This compound was prepared by the method of Example 2 Step c using 4-amino-3-methoxybenzoic acid to give the title compound as a solid (0.151 g).

$^1$H NMR: δ(CDCl$_3$) 1.95–2.43 (5H, m), 2.69–2.81 (3H, m), 3.42–3.91 (10H, m), 4.19–4.23 (1H, m), 6.56–7.25 (6H, m).

Melting point: 138–139° C.

EXAMPLE 5

This Example illustrates the preparation of (4-amino-3-methoxy-phenyl)-[4-(3,4-difluoro-phenoxy)-[1,4']bipiperidinyl-1'-yl]-methanone (Compound 1 in Table II).

Step a: 4-(3,4-Difluoro-phenoxy)-[1,4']bipiperidinyl-1'-carboxylic acid tert-butyl ester This compound was prepared by the method of Example 2, Step a using 4-(3,4-difluorophenoxy)piperidine to give the sub-title compound as a solid (0.48 g).

MS: APCI(+ve): 397 (M+H)

Step b: 4-(3,4-Difluoro-phenoxy)-[1,4']bipiperidinyl

This compound was prepared by the method of Example 2, Step b to give the sub-title compound as a solid (0.36 g).

MS: APCI(+ve): 297 (M+H)

Step c: (4-Amino-3-methoxy-phenyl)-[4-(3,4-difluoro-phenoxy)-[1,4']bipiperidinyl-1'-yl]-methanone This compound was prepared by the method of Example 2, Step c using 4-amino-3-methoxybenzoic acid to give the title compound as a gum (0.133 g).

$^1$H NMR: δ(CDCl$_3$) 1.50–1.60 (2H, m), 1.85–1.93 (4H, m), 2.04–2.08 (2H, m), 2.58–2.62 (2H, m), 2.69–2.75 (1H, m), 2.86–2.90 (4H, m), 3.86 (3H, s), 3.86 (2H, m), 4.25–4.30 (1H, m), 6.50–6.61 (1H , m), 6.65 (1H, dd), 6.70–6.75 (1H, m), 6.85 (1H, dt), 6.94 (1H, s), 7.01–7.09 (1H, m).

EXAMPLE 6

This Example illustrates the preparation of (4-amino-3-methoxy-phenyl)-[4-(3,4-difluoro-phenoxy)-[1,3']bipiperidinyl-1'-yl]-methanone (Compound 2 in Table II).

Step a: 4-(3,4-Difluoro-phenoxy)-[1,3']bipiperidinyl-1'-carboxylic acid tert-butyl ester This compound was prepared by the method of Example 2, Step a using 3-oxo-piperidine-1-carboxylic acid tert-butyl ester to give the sub-title compound as a solid (0.946 g).

MS: APCI(+ve): 397 (M+H)

Step b: 4-(3,4-Difluoro-phenoxy)-[1,3']bipiperidinyl

This compound was prepared by the method of Example 2, Step b to give the sub-title compound as a solid (0.706).

MS: ESI(+ve): 297 (M+H)

Step c: (4-Amino-3-methoxy-phenyl)-[4-(3,4-difluoro-phenoxy)-[1,3']bipiperidinyl-1'-yl]-methanone This compound was prepared by the same method as Example 2, Step c using 4-amino-3-methoxybenzoic acid to give the title compound as a gum (0.070 g).

$^1$H NMR: δ(CDCl$_3$) 1.41–1.67 (4H, m), 1.73–1.80 (2H, m), 1.86–2.00 (2H, m), 2.44 (3H, m), 3.00–3.13 (2H, m), 2.79–2.91 (2H, m), 3.82 (3H, s), 3.97–4.01 (1H, d), 4.14–4.17 (1H, d), 4.32 (1H, sept), 4.89 (2H, s), 6.67 (1H, d), 6.75–6.79 (1H, m), 6.80 (1H, dd), 6.87 (1H, s), 6.98–7.06 (1H, m), 7.27 (1H, q).

EXAMPLE 7

This Example illustrates the preparation of 4-(3,4-dichloro-phenoxy)-1'-(5-pyridin-2-yl-thiophene-2-sulfonyl)-[1,4']bipiperidinyl (Compound 280 in Table I).

The product of Example 2, Step b (0.2 g) was dissolved in acetone (4 ml). Potassium carbonate [0.134 g dissolved in H$_2$O (1.2 ml)] was then added, followed by 5-pyridin-2-yl-thiophene-2-sulfonyl chloride (0.168 g) and the reaction left to stir for 1 hr. Water was then added and the product extracted with ethyl acetate. The combined organic extracts dried with Na$_2$SO$_4$ and concentrated. Purification reverse phase HPLC (with a gradient eluent system (25% MeCN/NH$_4$OAc$_{aq}$ (0.1%) to 95% MeCN//NH$_4$OAc$_{aq}$ (0.1%)) gave the title compound as a solid (0.077 g).

$^1$H NMR: δ(DMSO-D6) 1.45–1.58 (4H, m), 1.79–1.90 (4H, m), 2.28–2.46 (5H, m), 2.66–2.73 (2H, m), 3.67–3.71 (2H, m), 4.35–4.43 (1H, m), 6.93–8.60 (9H, m). Melting point: 139–140° C.

EXAMPLE 8

This Example illustrates the preparation of 4-(3,4-difluoro-phenoxy)-1'-(5-pyridin-2-yl-thiophene-2-sulfonyl)-[1,4']bipiperidinyl (Compound 3 in Table II).

This compound was prepared by the method of Example 7 using product of Example 5, step b to give the title compound as a solid (0.095 g).

$^1$H NMR: δ(CDCl$_3$) 1.67–1.80 (4H, m), 1.87–2.01 (1H, t), 2.30 (1H, t), 2.39–2.50 (2H, m), 2.74–2.78 (2H, m), 3.89 (2H, d), 4.16–4.20 (1H, m), 6.56–6.60 (1H, m), 6.67–6.63 (1H, m), 7.03 (1H, q), 7.26 (1H, t), 7.52 (1H, d), 7.53 (1H, d), 7.70 (1H, d), 7.76 (1H, dt), 8.60 (1H, d). Melting point: 128–129° C.

EXAMPLE 9

This Example illustrates the preparation of [4-(3,4-dichloro-phenoxy)-[1,4']bipiperidinyl-1'-yl]-(2-methanesulfonyl-phenyl)-methanone (Compound 293 Table I).

Step 1: Preparation of 4-hydroxy-[1,4']bipiperidinyl-1'-carboxylic acid tert-butyl ester To 1-tert-butoxycarbonyl-4-piperidone (200 g, 1.01 mol) in tetrahydrofuran (THF) (1500 ml) was added 4-hydroxypiperidine (78.1 g, 0.77 mol). The resultant slurry was stirred for 30 minutes before cooling the reaction mixture with ice/water, acetic acid (47 ml) is then added (exotherm) which caused precipitation. The slurry was allowed to warm to room temperature before the addition of sodium triacetoxyborohydride (236 g, 1.12 mol) which was washed in with THF (500 ml). The resultant slurry was stirred overnight at room temperature. To the reaction mixture was added water (2000 ml) to give a solution. The solution was then extracted with diethyl ether (3×1800 ml). The aqueous phase was basified with 10% aq NaOH (950 ml) and extracted with dichloromethane (DCM) (3×1500 ml). The combined DCM layers are dried (MgSO$_4$), filtered and the solvent removed to give the sub-titled compound as a yellow viscous oil, (177 g, 81%; MS: (M+H) 285).

Step 2: Preparation of 4-(3,4-dichlorophenoxy)-[1,4']bipiperidinyl-1'-carboxylic acid tert-butyl ester To a solution of potassium tert-butoxide (139.0 g, 1.24 mol) in THF (500 ml) was added a solution of the product of Step 1 (176.2 g, 0.62 mol) in THF (1000 ml). The reaction mixture was stirred 10 minutes before the additon of 3,4 dichlorofluorobenzene (122.8 g, 0.74 mol), this caused a green colouration that subsequently faded. The reaction mixture was then heated at reflux for 90 minutes. The reaction mixture was then cooled to room temperature before the addition of saturated NaHCO$_3$ (1600 ml). The layers were separated and the organic layer stripped to leave an orange semi-solid. The solid was dissolved in DCM (1500 ml) and dried (MgSO$_4$), filtered and the solvent removed. To the resultant solid was added methyl tert-butyl ether (MTBE) (54 ml) and iso-hexane (1000 ml) to give a slurry which was stirred overnight. The slurry was then filtered and washed with isohexane (200 ml) and the solid dried in vacuo at 50° C. to give the sub-titled compound as a pale powder, (211.6 g, 80%; MS: (M+H) 429).

Step 3: Preparation of 4-(3,4-dichlorophenoxy)-[1,4']bipiperidine

The product of Step 2 (10.15 g, 23.6 mmol) was dissolved in dichloromethane (150 ml) and trifluoroacetic acid (40 ml, 519 mmol) added and the resultant solution stirred. After 90 minutes the dichloromethane and trifluoroacetic acid were removed on a rotary evaporator. The resultant oil was partitioned between ethyl acetate (100 ml) and 2M aq NaOH (100 ml). The layers were separated and the organics extracted with 10% aq citric acid (100 ml). The layers were separated and the aqueous basified with 2M aq NaOH and extracted with ethyl acetate (200 ml). The organics were dried (MgSO$_4$), filtered and the solvent removed to give the sub-titled product as a pale oil which solidified on standing (4.62 g, 59%; MS: (M+H) 329).

Step 4: Preparation of [4-(3,4-dichloro-phenoxy)-[1,4']bipiperidinyl-1'-yl]-(2-methanesulfonyl-phenyl)-methanone Oxalyl chloride (55 ml, 0.63 mol) was added dropwise over 10 minutes to a stirred suspension of 2-methanesulfonyl-benzoic acid (7.1 g, 0.036 mol) in DCM (550 ml) containing DMF (0.5 ml). The solution was then stirred for 2 hours at room temperature. The solution was then evaporated to give a solid that was redissolved in dichloromethane and again evaporated to give a yellow solid. The solid acid chloride was dissolved in DCM (275 ml) and was added over 10 minutes to a stirred solution of the product of Step 3 (11.0 g, 0.033 mol) and triethylamine (15.4 ml, 0.11 mol) in dichloromethane (125 ml). The resultant solution was stirred at room temperature for 16 hours. The solution was then washed with water (500 ml), 1M aq NaOH (500 ml) and water (2×500 ml). The organic phase was dried (MgSO$_4$), filterered and the solvent removed to give a pale yellow foam. The foam was triturated with diethyl ether to give the title compound (12.96 g, 76%).

Melting point 141° C. $^1$H NMR: (400 MHz, CDCl$_3$) δ1.39–1.63 (1H, m), 1.72–2.04 (6H, m), 2.42–2.68 (2H, m), 2.73–2.92 (3H, m), 3.00–3.08 (1H, m), 3.23 (1H, s), 3.28 (2H, s), 3.34–3.40 (1H, m), 3.46–3.52 (1H, m), 4.21–4.30 (1H, m), 4.62–4.68 (1H, m), 4.80–4.86 (1H, m), 6.72–6.76 (1H, m), 6.97–7.00 (1H, m), 7.28–7.32 (1H, m), 7.32–7.37 (1H, m), 7.56–7.61 (1H, m), 7.64–7.70 (1H, m), 8.05–8.10 (1H, m).

EXAMPLE 10

This Example illustrates the preparation of [4-(3,4-dichloro-phenoxy)-[1,4']bipiperidinyl-1'-yl]-(3-methanesulfonyl-phenyl)-methanone (Compound 281 Table I).

Oxalyl chloride (30 mls, 0.35 mol) was added dropwise over 10 minutes to a stirred suspension of 3-methanesulfonyl-benzoic acid (6 g, 0.03) in DCM (300 ml) containing DMF (0.3 ml). The solution was then stirred for 4 hours at room temperature. The solution was then evaporated under high vacuum to give a solid which was redissolved in dichloromethane and again evaporated to give a yellow solid. The solid acid chloride was dissolved in DCM (100 ml) and was added over 10 minutes to a stirred solution of the product of step 3 of Example 9 (9.3 g, 0.028 mol) and triethylamine (8.4 ml, 0.06 mol) in dichloromethane (100 ml). The resultant solution was stirred at room temperature for 3 hours. The solution was then washed with water (100 ml), 1M aq NaOH (2×100 ml) and water (2×100 ml). The organic phase was dried (MgSO$_4$), filtered and the solvent removed to give a pale yellow foam. The foam was dissolved in methanol (100 ml) and allowed to crystallise. The crystals were filtered, washed with methanol and then dried to give the title compound (12.2 g, 84%).

Melting point 157° C. $^1$H NMR: (400 MHz, CDCl$_3$) δ 1.40–1.65 (2H, m), 1.75–1.85 (3H, m), 1.93–2.03 (3H, m), 2.42–2.51 (2H, m), 2.58 (1H, tt), 2.74–2.91 (3H, m), 3.00–3.14 (1H, m), 3.07 (3H, s), 3.62–3.76 (1H, m), 4.27 (1H, septet), 4.69–4.80 (1H, m), 6.75 (1H, dd), 6.99 (1H, d), 7.31 (1H, d), 7.64 (1H, t), 7.69 (1H, dt), 7.97–7.98 (1H, m), 8.00 (1H, dt).

The hydrochloride salt (melting point 159° C.) was prepared by evaporation to dryness of a clear solution of Compound 281 of Table I and HCl in ethanol.

EXAMPLE 11

This Example illustrates the preparation of [4-(3,4-dichloro-phenoxy)-[1,4']bipiperidinyl-1'-yl]-(2-methanesulfonyl-thiophen-5-yl)-methanone (Compound 332 of Table I).

Oxalyl chloride (32 ml, 0.37 mol) was added dropwise over 10 minutes to a stirred suspension of 5-(methylsulfonyl)-2-thiophenecarboxylic acid (6.64 g, 0.032) in DCM (300 ml) containing DMF (0.3 ml). The solution was then stirred for 2 hours at room temperature. The solution was then removed to give a solid which was redissolved in dichloromethane and the solvent again removed to give a yellow solid. The solid acid chloride was dissolved in DCM (150 ml) and was added over 10 minutes to a stirred solution of the product of step 3 of Example 9 (10 g, 0.03 mol) and triethylamine (9 ml, 0.065 mol) in dichloromethane (300 ml). The resultant solution was stirred at room temperature for 2 hours. The solution was then washed with water (100 ml), 1M aq NaOH (2×100 ml) and water (300 ml). The organic phase was dried (MgSO$_4$), filterered and the solvent removed to give an orange foam. The solid was dissolved in dichloromethane (200 ml) and purified by chromatography using ethyl acetate and then acetone as the eluant. The purified material was precipitated from acetone by the addition of iso-hexane. The crystals were filtered, washed with isohexane and then dried to give the title compound (11.5 g, 74%).

Melting point: 153–154° C. $^1$H NMR (399.98 MHz, DMSO-D6) δ 1.42–1.48 (2H, m), 1.56–1.62 (2H, m), 1.77–1.84 (2H, m), 1.90–1.96 (2H, m), 2.37–2.43 (2H, m), 2.56–2.63 (2H, m), 2.75–2.80 (2H, m), 2.89–3.14 (2H, m), 3.29–3.32 (1H, m), 3.41 (3H, s), 4.41–4.45 (1H, m), 6.98 (1H, dd), 7.25 (1H, d), 7.49 (2H, q), 7.77 (1H, d).

EXAMPLE 12

This Example illustrates the preparation of [4-(4-chloro-2-methyl-phenoxy)-[1,4']bipiperidinyl-1'-yl]-(3-methanesulfonyl-phenyl)-methanone (Compound 1 of Table IV)

A solution of 4-(2-methyl-4-chloro-phenoxy)-piperidine (0.87 mmol) and 1-(3-methanesulfonyl-benzoyl)-piperidin-4-one (0.925 mmol) in NMP (5 ml) and glacial acetic acid (1 mmol) was stirred at room temperature for 1 hour after which sodium triacetoxy borohydride (2 mmol) was added. The resulting mixture was stirred at RT for 24 hours, evaporated on to silica (2 g) and placed on to a Mega Bond elut cartridge (10 g Silica). The product was eluted with DCM/MeOH mixtures and further purified by Reverse Phase preparative chromatography, MeOH/aqueous TFA gradient on a Symmetry column. The free base was isolated by dissolving in EtOAc and washing with sodium bicarbonate solution, drying the organic layer with MgSO$_4$ and evaporation left the product as a white solid (0.047 g; M.pt. 83–84° C.).

$^1$H NMR (300 MHz, DMSO-D6) δ 1.2–2.8 (bm, 14H), 2.15 (s, 3H), 3.1 (bm, 1H), 3.25 (s, 3H), 3.5 (bm, 1H), 4.4 (bm, 1H), 4.5(bm, 1H), 7.0 (d, 1H), 7.12 (m, 1H), 7.2 (d, 1H), 7.7 (m, 2H), 7.9 (s, 1H), 8.0 (dd, 1H).

EXAMPLE 13

This Example illustrates the preparation of (4-amino-3-methoxy-phenyl)-[4-(4-chloro-2-methyl-phenoxy)-[1,4']bipiperidinyl-1'-yl]-methanone ditrifluoroacetate (Compound 23 of Table IV).

A solution of the 4-(4-chloro-2-methyl-phenoxy)-piperidine (0.87 mmol) and 1-(4-nitro-3-methoxy-benzoyl)-piperidin-4-one (0.925 mmol) in NMP (5 ml) and glacial acetic acid (1 mmol) was stirred at RT for 1 hour after which sodium triacetoxy borohydride (2 mmol) was added. The resulting mixture was stirred at RT for 24 hours, evaporated on to silica (2 g) and placed on to a Mega Bond elut cartridge (10 g Si). The product was eluted with DCM/MeOH mixtures and further purified by SCX, eluting the product with 10% aq NH$_3$ in MeOH. The nitro compound was dissolved in THF (10 ml) and hydrogenated over 10% Pd on C at 3 atmospheres in Peteric apparatus. The mixture was filtered and the filtrate evaporated, the residue was then purified by RPHPLC, using a Symmetry column and eluting with MeOH/aqueous TFA mixtures. The product was isolated as the trifluoroacetate by evaporation of the appropriate HPLC fractions (0.046 g; m.pt. 84–85° C.).

$^1$H NMR (400 MHz, DMSO-D6) δ 1.4–2.4 (m, 13H), 2.9 (m, 2H), 3.15 (m, 2H), 3.4 (m, 1H), 3.55 (m, 2H), 3.8 (s, 3H), 4.2 (bs, 2H), 4.55 and 4.8 (2 bm, 1H), 6.68 (d, 1H), 6.82 (d, 1H), 6.85 (s, 1H), 7.0–7.22 (m, 2H), 7.25 (s, 1H), 9.5 (bm, 1H).

EXAMPLE 14

This Example illustrates the preparation of 2-[1'-(3-methanesulfonyl-benzoyl)-[1,4']bipiperidinyl-4-yloxy]-5- trifluoromethyl-benzonitrile trifluoroacetate (Compound 291 of Table IV).

The product of Method E (183 mg, 0.5 mmol) was dissolved in DMSO (2 ml) and treated with sodium hydride (22 mg 1 equiv. of 60%) under an inert atmosphere. After stirring the mixture at RT for 1 hour, 2-fluoro-5-trifluoromethyl-benzonitrile (1 equiv.) was added. After stirring at RT for 24 hours, the reaction mixture was acidified (glacial acetic acid) and filtered. The filtrate was purified by RPHPLC. (MeOH/aqueous TFA, Symmetry column) to give the product as the trifluoroacetate salt (0.06 g; m.pt. 110–111° C.).

$^1$H NMR (400 MHz, DMSO-D6) δ 1.0–3.8 (m, 20 H), 4.5–5.3 (m, 2H), 7.5 (d, 1H), 7.75 (m, 3H), 8.02 (m, 2H).

EXAMPLE 15

This Example illustrates the preparation of (3-methanesulfonyl-phenyl)-[4-(6-methyl-pyridin-2-yloxy)-[1,4']bipiperidinyl-1'-yl]-methanone trifluoroacetate (Compound 292 of Table IV).

The product of Method E (1 mmol) and potassium tert-butoxide (2 mmol) were stirred together in dry THF (20 ml) at RT. After 10 mins 2-fluoro-6-methyl-pyridine (1 mmol) was added and the reaction mixture stirred at reflux overnight. The reaction mixture was cooled, diluted with water and extracted into ethyl acetate (3×50 ml). The combined extracts were dried (MgSO$_4$) and evaporated. The residue was purified by RPHPLC. (MeOH/aqueous TFA, Symmetry column) to give the product as the trifluoroacetate salt (0.03 g; m.pt. 61–62° C.).

$^1$H NMR (400 MHz, DMSO-D6) δ 1.6–3.8 (m, 15H), 2.4 (s, 3H), 3.3 (s, 3H), 4.5–5.4 (m, 3H), 6.6 (m, 1H), 6.02 (dd, 1H), 7.6 (q, 1H), 7.82 (m, 2H), 7.95 (s, 1H), 8.02 (m, 1H), 9.7 (bs, 1H)

EXAMPLE 16

This Example illustrates the preparation of N-{3-[4-(3,4-dichloro-phenoxy)-[1,4']bipiperidinyl-1'-carbonyl]-phenyl}-methanesulfonamide (Compound 583 of Table I).

To (3-amino-phenyl)-[4-(3,4-dichloro-phenoxy)-[1,4'] bipiperidinyl-1'-yl]-methanone (0.133 g) in pyridine (2 mL) was added methanesulfonyl chloride (0.024 ml) and the reaction left to stir for 5 minutes. The solvent was evaporated, water (0.5 mL) added and the solvent re-evaporated. Purification by RPHPLC (with a gradient eluent system (25% MeCN/NH$_4$OAc aq (0.1%) to 95% MeCN//NH$_4$OAc aq (0.1%)) gave the title compound (0.050 g; m.pt. 94–95° C.).

$^1$H NMR (399.978 MHz, CDCl$_3$) δ 1.59–2.09 (8H, m), 2.22 (2H, br s), 2.54–2.60 (1H, m), 2.81 (2H, br s), 3.02 (5H, br s), 3.51–3.75 (1H, br m), 4.25–4.28(1H, m), 4.29 (1H, br s), 6.70–7.52 (8H, m).

EXAMPLE 17

This Example illustrates the preparation of N-{2-[4-(3,4-dichloro-phenoxy)-[1,4']bipiperidinyl-1'-carbonyl]-phenyl}-methanesulfonamide (Compound 587 of Table I).

To a solution of (2-amino-phenyl)-[4-(3,4-dichloro-phenoxy)-[1,4']bipiperidinyl-1'-yl]-methanone (0.2 g) in pyridine (2 ml) at 0° C. was added methane sulphonyl chloride (0.039 ml). The mixture was allowed to warm to room temperature and the pyridine removed by evaporation. The residue was azeotroped with water and the product purified by RPHPLC (Symmetry column, eluting 25% to 95% MeCN/0.1% NH$_4$OAc aq at 20 ml/min over 6 minutes) to give the product as a colourless solid (0.09 g).

$^1$H NMR: (399.978 MHz, CDCl$_3$) δ 1.49–1.69 (5H, m), 1.77–1.84 (2H, m), 1.87–1.94 (1H, m), 1.95–2.02 (2H, m), 2.43–2.50 (2H, m), 2.59 (1H, tt), 2.78–2.84 (2H, m), 2.87–3.03 (1H, m), 3.08 (3H, s), 3.17 (1H, sextet), 4.27 (1H, septet), 6.75 (1H, dd), 6.99 (1H, d), 7.15 (1H, td), 7.24 (1H, d), 7.31 (1H, d), 7.43 (1H, td), 7.62 (1H, d).

EXAMPLE 18

This Example illustrates the preparation of [4-(3,4-dichloro-phenoxy)-[1,4']bipiperidinyl-1'-yl]-(1-methanesulfonyl-1H-indol-3-yl)-methanone hydrochloride (Compound 592 of Table I).

To a solution of Compound 471 of Table I (0.17 g) in dimethylformamide (3 ml) at 0° C. under an atmosphere of nitrogen, was added sodium hydride (0.014 g of a 60% suspension in oil). The mixture was stirred for 5 minutes then methanesulphonyl chloride (0.027 ml in 1 ml of dimethylformamide) was added and then mixture allowed to warm to room temperature over 12 hours. The reaction mixture was partitioned between dichloromethane (10 ml) and water (10 ml). The organic layer was separated, dried (MgSO$_4$) and the solvent removed by evaporation. The residue was purified by RPHPLC (Symmetry, 25% to 95% MeCN/0.1% NH$_4$OAc aq over 6 minutes, 20 ml/min, 220 nm) to give a colourless solid (0.062 g; m.pt. 173–175° C.).

$^1$H NMR: (299.944 MHz DMSO-D6) δ 1.72–1.87 (2H, m), 2.01–2.34 (5H, m), 2.48–2.55 (1H, m), 2.98–3.13 (2H, m), 3.13–3.27 (2H, m), 3.39–3.47 (2H, m), 3.53–3.62 (2H, m), 3.64 (3H, s), 4.35–4.58 (1H, m), 4.65–4.76 (1H, m), 7.12 (1H, dd), 7.39–7.48 (2H, m), 7.52 (1H, t), 7.61 (1H, t), 7.79 (1H, d), 7.88 (1H, s), 7.95 (1H, d).

EXAMPLE 19

This Example illustrates the preparation of 1-[4-(3,4-dichloro-phenoxy)-[1,4']bipiperidinyl-1'-yl]-2-phenyl-3-piperazin-1-yl-propan-1-one (Compound 595 of Table I).

Compound 575 of Table I (0.178 g) was treated with 6N hydrochloric acid (5 ml) and stirred at room temperature for 24 hours. 2N Sodium hydroxide solution was added and the reaction mixture extracted with ethyl acetate. The organic extracts were combined, washed with water, dried (MgSO$_4$) and evaporated to give a white solid. Purification was by reverse phase HPLC (with a gradient eluent system (25% MeCN/NH$_4$OAc aq (0.1%) to 95% MeCN//NH4OAcaq (0.1%)). (Any excess NH$_4$OAc was removed by dissolving the compound in ethyl acetate and washing with aqueous saturated NaHCO$_3$ followed by drying of the organics with MgSO$_4$ and evaporation of solvent.) The title compound was a white solid (0.087 g).

$^1$H NMR (399.98 MHz, DMSO-D6) δ 1.20–1.95 (9H, m), 2.10–2.53 (9H, m), 2.59–2.65 (2H, m), 2.70–2.77 (1H, m), 2.89–3.12 (4H, m), 4.02–4.47 (4H, m), 6.89–7.00 (1H, m), 7.16–7.32 (6H, m), 7.44–7.52 (1H, m).

EXAMPLE 20

This Example illustrates the preparation of [4-(3,4-dichloro-phenoxy)-1-oxy-[1,4']bipiperidinyl-1'-yl]-(3-methanesulfonyl-phenyl)-methanone.

The product Example 10 (0.100 g) in dichloromethane (5 ml) was treated with m-chloroperbenzoic acid (0.043 g) and the reaction stirred at room temperature for 0.5 hours. Saturated aqueous sodium hydrogencarbonate was added and the reaction mixture extracted with dichloromethane. The combined organic extracts were washed with water, dried (MgSO$_4$) and evaporated to give a brown foam.

Purification by RPHPLC (with a gradient eluent system (25% MeCN/NH₄OAc aq (0.1%) to 95% MeCN//NH₄OAc aq (0.1%)) gave the title compound as a white solid (0.021 g).

¹H NMR (299.946 MHz, DMSO-D6) δ 1.70–2.91 (15H, m), 3.24–3.44 (3H, m), 3.55–3.68 (1H, m), 4.55–4.76 (2H, m), 6.99–7.06 (1H, m), 7.29–7.33 (1H, m), 7.53 (1H, dd), 7.71–7.79 (2H, m), 7.93 (1H, s), 7.99–8.05 (1H, m).

EXAMPLE 21

This Example illustrates the preparation of [4-(3,4-dichloro-phenoxy)-[1,4']bipiperidinyl-1'-yl]-phenyl-methanone (Compound 1 of Table I).

To a solution of 4-(3,4-dichloro-phenoxy)-[1,4']bipiperidine (0.1 g, see step b of Example 2) in dichloromethane (5 ml) and triethylamine (0.2 ml) was added benzoyl chloride (0.045 ml) and the reaction mixture was stirred for 2 hours. The mixture was washed with water, dried (MgSO₄), filtered and the solvents evaporated to leave a gum. Purification by RPHPLC [with an eluent system (50% MeCN/0.1% NH₄OAc aq), any excess NH₄OAc was removed by dissolving the compound in ethyl acetate and washing with aqueous saturated NaHCO₃ followed by drying of the organics with MgSO₄ and evaporation of solvent] and trituration of the resulting product with diethyl ether gave a solid which was filtered and dried to give the title compound (0.120 g; m.pt. 122° C.).

¹H NMR (299.944 MHz CDCl₃) δ 1.42–1.62 (2H, m), 1.78–1.82 (3H, m), 1.95–2.01 (3H, m), 2.39–2.69 (3H, m), 2.69–3.09 (4H, m), 3.63–3.95 (1H, m), 4.24–4.29 (1H, m), 4.62–4.89 (1H, m), 6.73–6.77 (1H, m), 6.99 (1H, d), 7.26–7.29 (1H, m), 7.39 (5H, s).

EXAMPLE 22

This Example illustrates the preparation of [4-(3,4-dichloro-benzenesulfonyl)-[1,4']bipiperidinyl-1'-yl]-(4-methanesulfonyl-phenyl)-methanone (Compound 4 of Table V).

Step 1: 4-(3,4-dichloro-phenylsulfanyl)-piperidine-1-carboxylic acid tert-butyl ester 4-Methanesulfonyloxy-piperidine-1-carboxylic acid tert-butyl ester (11.18 g) and 3,4-dichlorothiophenol (6.15 ml) were stirred together in acetonitrile (200 ml) and potassium carbonate (8.86 g) was added. The mixture was heated at reflux for 18 hours after which water was added and the resulting mixture extracted with dichloromethane. The organic extracts were combined, washed with water, dried (MgSO₄) and evaporated to give the sub-title compound (14.58 g).

¹H NMR (299.944 MHz, CDCl₃) δ 1.45 (9H, s), 1.49–1.62 (2H, m), 1.87–1.96 (2H, m), 2.89–2.98 (2H, m), 3.16–3.26 (1H, m), 3.91–4.01 (2H, m), 7.21–7.57 (3H, m).

Step 2: 4-(3,4-dichloro-benzenesulfonyl)-piperidine-1-carboxylic acid tert-butyl ester The product from Step 1(1 g) and m-chloroperbenzoic acid (1.19 g) were stirred at ambient temperature in dichloromethane (10 ml) for 18 hours. Sodium metabisulphite (1.19 g) in water (5 ml) was added and stirring was continued for 0.5 hours after which the reaction mixture was extracted with dichloromethane. The combined organics were washed with saturated sodium bicarbonate solution, dried (MgSO₄) and evaporated to give the sub-title compound (0.34 g).

¹H NMR (399.978 MHz, CDCl₃) δ 1.45 (9H, s), 1.56–1.65 (2H, m), 1.94–2.00 (2H, m), 2.62–2.70 (2H, m), 3.01–3.09 (1H, m), 4.21–4.30 (2H, m), 7.66–7.70 (2H, m), 7.93–7.98 (1H, m).

Step 3: 4-(3,4-dichloro-benzenesulfonyl)-piperidine

The product of step 2 was deprotected following the procedure of Example 1 step b. ¹H NMR (299.944 MHz, CDCl₃) δ 1.64–1.71 (2H, m), 1.96–2.05 (2H, m), 2.55–2.64 (2H, m), 2.99–3.10 (1H, m), 3.19–3.27 (2H, m), 7.66–7.71 (2H, m), 7.92–7.98 (1H, m).

Step 4: 4-(3,4-dichloro-benzenesulfonyl)-[1,4']bipiperidinyl-1'-carboxylic acid tert-butyl ester The product of step 3 was used in a reductive amination with 4-oxo-piperidine-1- carboxylic acid tert-butyl ester following the procedure of Example 2 step a.

Step 5: 4-(3,4-Dichloro-benzenesulfonyl)-[1,4']bipiperidinyl

The product of step 4 was deprotected following the procedure of Example 2 step b. ¹H NMR (299.946 MHz, DMSO-D6) δ 1.22–1.61 (7H, m), 1.77–1.83 (2H, m), 2.09–2.16 (1H, m), 2.25–2.45 (3H, m), 2.87–2.98 (4H, m), 3.35–3.43 (1H, m), 7.81 (1H, dd), 7.96 (1H, d), 8.05 (1H, d)

Step 6: [4-(3,4-dichloro-benzenesulfonyl)-[1,4']bipiperidinyl-1'-yl]-(4-methanesulfonyl-phenyl)-methanone The product of step 5 was coupled to 4-methanesulfonyl-benzoic acid following the procedure of Example 2 step c.

1H NMR (299.946 MHz, DMSO-D6) δ 1.34–1.62 (5H, m), 1.70–1.85 (4H, m), 2.13 (3H, t), 2.72–3.04 (4H, m), 3.27 (3H, s), 3.37–3.48 (1H, m), 4.44–4.52 (1H, m), 7.63 (2H, d), 7.81 (1H, dd), 7.95–8.00 (3H, m), 8.06 (1H, d).

[4-(3,4-Dichloro-benzenesulfonyl)-[1,4']bipiperidinyl-1'-yl]-phenyl-methanone (Compound 5 of Table V). The product of step 5 was coupled to benzoic acid following the procedure of Example 2 step c. ¹H NMR (299.946 MHz, DMSO-D6) δ 1.31–1.69 (5H, m), 1.82 (3H, d), 2.15 (2H, d), 2.69–2.75 (1H, m), 2.90–2.97 (4H, m), 3.33–3.43 (1H, m), 3.48–3.63 (1H, m), 4.42–4.53 (1H, m), 7.39 (5H, dt), 7.81 (1H, dd), 7.96 (1H, d), 8.06 (1H, d).

EXAMPLE 23

This Example illustrates the preparation of 3-[4-(3,4-dichloro-phenoxy)-[1,4']bipiperidinyl-1'-carbonyl]-1-ethyl-7-methyl-1H-[1,8]naphthyridin-4-one (Compound 534 of Table I).

4-(3,4-Dichloro-phenoxy)-[1,4']bipiperidine (0.2 g, see step b of Example 2) was dissolved in dichloromethane (5 ml), bromo-tris-pyrrolidino-phosphonium hexafluorophosphate (PYBROP™; 0.425 g), 1-ethyl-7-methyl-4-oxo-1,4-dihydro-[1,8]naphthyridine-3-carboxylic acid (0.155 g) and triethylamine (0.254 ml) were added. After 16 hours at room temperature dichloromethane and aqueous NaHCO₃ solution were added. The product was extracted with dichloromethane, the combined organic extracts were washed with water, dried with MgSO₄ and concentrated. Purification by RPHPLC (with a gradient eluent system (45% MeCN/NH₄OAc aq (0.1%) to 95% MeCN//NH₄OAc aq (0.1%)) %)) (any excess NH₄OAc was removed by dissolving the compound in ethyl acetate and washing with aqueous saturated NaHCO₃ followed by drying of the organics with Magnesium sulfate and evaporation of solvent) gave the title compound (0.184 g; m.pt. 189–190° C.)

MS: APCI⁺(M+H) 543 ¹H NMR (299.946 MHz, DMSO-D6) δ 1.37 (3H, t), 1.47–1.69 (5H, m), 1.78–1.84 (1H, m), 1.89–1.97 (2H, m), 2.36–2.41 (2H, m), 2.49–2.56 (1H, m), 2.66 (3H, s), 2.70–2.79 (3H, m), 2.95–3.04 (1H, m), 3.52–3.59 (1H, m), 4.38–4.57 (4H, m), 6.95–6.99 (1H, m), 7.22–7.24 (1H, m), 7.35–7.40 (1H, m), 7.46–7.51 (1H, m), 8.37 (1H, s), 8.43–8.45 (1H, m).

EXAMPLE 24

This Example illustrates the preparation of 4-[4-(3,4-dichloro-phenoxy)-[1,4']bipiperidinyl-1'-carbonyl]-2H-isoquinolin-1-one (Compound 572 of Table I).

4-(3,4-Dichloro-phenoxy)-[1,4']bipiperidine (0.2 g, see step b of Example 2) was dissolved in dichloromethane (5 ml), bromo-tris-pyrrolidino-phosphonium hexafluorophosphate (PYBROP™; 0.425 g), 1-oxo-1,2-dihydro-isoquinoline-4-carboxylic acid (0.126 g) and triethylamine (0.254 ml) were added. After 16 hours at room temperature dichloromethane and aqueous NaHCO$_3$ solution were added. The product was extracted with dichloromethane, the combined organic extracts were washed with water, dried with MgSO$_4$ and concentrated. Purification by RPHPLC (with a gradient eluent system (45% MeCN/NH$_4$OAc aq (0.1%) to 95% MeCN//NH$_4$OAc aq (0.1%))) (any excess NH4OAc was removed by dissolving the compound in ethyl acetate and washing with aqueous saturated NaHCO$_3$ followed by drying of the organics with Magnesium sulfate and evaporation of solvent) gave the title compound (0.153 g).

MS: APCI$^+$(M+H) 500 $^1$H NMR (299.944 MHz CDCl$_3$) δ 1.37–1.66 (2H, m), 1.73–1.88 (3H, m), 1.93–2.05 (3H, m), 2.41–2.51 (2H, m), 2.52–2.63 (1H, m), 2.75–2.86 (2H, m), 2.86–3.09 (2H, m), 3.71–3.90 (1H, m), 4.23–4.32 (1H, m), 4.77–4.93 (1H, m), 6.75 (1H, dd), 6.99 (1H, d), 7.27–7.32 (3H, m), 7.54–7.67 (1H, m), 7.57 (1H, t), 7.74 (1H, t), 8.46 (1H, d).

EXAMPLE 25

This Example illustrates the preparation of [4-(3,4-dichloro-phenoxy)-[1,4']bipiperidinyl-1'-yl]-(6-fluoro-imidazo[1,2-a]pyridin-2-yl)-methanone (Compound 579 of Table I).

Step a: 6-Fluoro-imidazo[1,2-a]pyridine-2-carboxylic acid ethyl ester

To a solution of 2-amino-5-fluoropyridine (1.12 g) in diethyl ether (25 ml) was added ethyl bromopyruvate (1.25 ml). the mixture was stirred for 1 hour. The resultant solid was filtered off, suspended in ethanol and heated at reflux for 4 hours. The solvent was removed by evaporation and the residue partitioned between ethyl acetate (100 ml) and aqueous sodium bicarbonate solution (100 ml). The organic layer was separated, dried, (magnesium sulfate) and the solvent removed by evaporation. The residue was purified by flash chromatography (silica) eluting with ethyl acetate:hexane (3:1) to give the sub-title compound as a colourless solid (1.12 g).

MS: ES$^+$(M+H) 209 $^1$H NMR (399.98 MHz, CDCl$_3$) δ 1.44 (3H, t), 4.46 (2H, q), 7.19 (1H, ddd), 7.68 (1H, dd), 8.07–8.09 (1H, m), 8.19 (1H, s).

Step b: 6-Fluoro-imidazo[1,2-a]pyridine-2-carboxylic acid

A solution of 6-fluoro-imidazo[1,2-a]pyridine-2-carboxylic acid ethyl ester (1 g) in 4N HCl was refluxed for 4 hours. The solvent was evaporated to give the sub-title compound as a white solid (0.86 g).

MS: ES$^+$(M+H) 181 $^1$H NMR (399.98 MHz, DMSO-D6) δ 7.81–7.89 (2H, m), 8.71 (1H, s), 9.03 (1H, s).

Step c: [4-(3,4-Dichloro-phenoxy)-[1,4']bipiperidinyl-1'-yl]-(6-fluoro-imidazo[1,2-a]pyridin-2-yl)-methanone 4-(3,4-Dichloro-phenoxy)-[1,4']bipiperidine (0.2 g, see step b of Example 2) was dissolved in dichloromethane (5 ml), bromo-tris-pyrrolidino-phosphonium hexafluorophosphate (PYBROP™; 0.425 g), 6-fluoro-imidazo[1,2-a]pyridine-2-carboxylic acid (0.126 g) and triethylamine (0.254 ml) were added. After 16 hours at room temperature dichloromethane and aqueous NaHCO$_3$ solution were added. The product was extracted with dichloromethane, the combined organic extracts were washed with water, dried with MgSO$_4$ and concentrated. Purification by reverse phase HPLC (with a gradient eluent system (45% MeCN/NH$_4$OAc aq (0.1%) to 95% MeCN//NH$_4$OAc aq (0.1%)) (any excess NH$_4$OAc was removed by dissolving the compound in ethyl acetate and washing with aqueous saturated NaHCO$_3$ followed by drying of the organics with magnesium sulfate and evaporation of solvent) gave the title compound (0.104 g).

MS: APCI$^+$(M+H) 491 $^1$H NMR (399.978 MHz, CDCl$_3$) δ 1.61 (1H, qd), 1.75–2.02 (7H, m), 2.42–2.51 (2H, m), 2.59–2.67 (1H, m), 2.75–2.86 (3H, m), 3.12–3.21 (1H, m), 4.23–4.29 (1H, m), 4.76–4.85 (1H, m), 5.23–5.32 (1H, m), 6.75 (1H, dd), 6.99 (1H, d), 7.16 (1H, ddd), 7.30 (1H, d), 7.58 (1H, dd), 8.07 (2H, s).

EXAMPLE 26

This Example illustrates the preparation of 4-(3,4-dichloro-phenoxy)-[1,4']bipiperidinyl-1'-carboxylic acid phenylamide (Compound 309 of Table IV).

Phenylisocyanate(0.078 ml) was added to a solution of 4-(3,4-dichloro-phenoxy)-[1,4']bipiperidine (0.2 g, see Example 2 step b) in dichloromethane (5 ml). The mixture was stirred at 23° C. for 16 hours. The resulting precipitate was filtered, washed with dichloromethane (2×5 ml) then crystallised from acetonitrile to afford the title compound as a solid (0.2 g; melting point 215–216° C.).

$^1$H NMR (DMSO-D6) δ 1.35 (2H, qd), 1.53–1.62 (2H, m), 1.72–1.78 (2H, m), 1.89–1.96 (2H, m), 2.36–2.42 (2H, m), 2.44–2.52 (1H, m), 2.72–2.78 (4H, m), 4.15 (2H, d), 4.39–4.45 (1H, m), 6.91 (1H, tt), 6.98 (1H, dd), 7.19–7.23 (2H, m), 7.25 (1H, d), 7.43–7.46 (2H, m), 7.49 (1H, d), 8.46 (1H, s).

4-(3,4-Dichloro-phenoxy)-[1,4']bipiperidinyl-1'-carbothioic acid phenylamide was prepared using the methodology of Example 26 and employing phenylisothiocyanate, (melting point 162–163° C.). $^1$H NMR: (DMSO-d6) δ 1.39–1.49 (2H, m), 1.53–1.62 (2H, m), 1.79 (2H, d), 1.89–1.96 (2H, m), 2.39 (2H, t), 2.54–2.63 (1H, m), 2.73–2.80 (2H, m), 3.04 (2H, t), 4.39–4.46 (1H, m), 4.72 (2H, d), 6.98 (1H, dd), 7.06–7.10 (1H, m), 7.23–7.30 (5H, m), 7.49 (1H, d), 9.24 (1H, s).

EXAMPLE 27

This Example illustrates the preparation of 4-(3,4-dichloro-phenoxy)-[1,4']bipiperidinyl-1'-carboxylic acid (3-methanesulfonyl-phenyl)-amide (Compound 54 of Table IV).

Hydrogen peroxide (100 μl, 30%) was added to a cooled (0° C.) solution of Compound 312 of Table IV (0.13 g) in trifluoroacetic acid (1 ml). The mixture was allowed to reach ambient temperature and stirred for a further 1 hour. The solution was quenched with water(5 ml), basified to pH11 with 2M sodium hydroxide solution and extracted with ethyl acetate. The organic solution was separated, washed with water(2×5 ml), dried (MgSO$_4$), filtered and the filtrate evaporated to leave a gum. The gum was dissolved in acetonitrile and purified by RPHPLC (Nova Pak column) eluting with acetonitrile/0.1% ammonium acetate aq (1:1). The required fractions were evaporated and then lyophilised to give the title compund as a colourless powder (0.03 g).

$^1$H NMR (DMSO-D6) δ 1.31–1.42 (2H, m), 1.53–1.62 (2H, m), 1.77 (2H, d), 1.89–1.96 (2H, m), 2.36–2.43 (3H, m), 2.74–2.82 (4H, m), 3.16 (3H, s), 4.18 (2H, d), 4.42 (1H, septet), 6.98 (1H, dd), 7.25 (1H, d), 7.44–7.52 (3H, m), 7.80–7.83 (1H, m), 8.09 (1H, t), 8.90 (1H, s).

Selected proton NMR data and/or melting point data are provided for certain further compounds in Tables VI and VII below.

TABLE VI

| Compound (Table no.) | NMR data |
|---|---|
| 3 (I) | δ(D₂O) 1.97–1.69(2H, m), 2.21–2.08(2H, m), 2.51–2.23(4H, m), 3.07–2.96(1H, m), 3.31 –3.17(2H, m), 3.45 –3.32(2H, m), 3.56–3.45(1H, m), 3.75–3.56(2H, m), 4.88–4.70(3H, m), 7.07–7.02(1H, m), 7.36–7.30(1H, m), 7.46–7.37(1H, m), 7.55(2H, d), 7.74–7.72(1H, m) |
| 8 (I) | δ(CDCl₃) 1.67–1.41(2H, m), 1.86–1.76(3H, m), 2.04–1.93(3H, m), 2.51–2.42(3H, m), 2.62–2.56(1H, m), 2.88–2.76(3H, m), 3.06(1H, t), 3.66(1H, d), 4.28(1H, septet), 4.76(1H, d), 6.75(1H, dd), 6.99(1H, d), 7.31(1H, d), 7.56(2H, d), 8.28(2H, d) |
| 18 (I) | δ(CD₃OD) 1.59–1.41(2H, m), 1.83–1.68(2H, m), 2.08–1.93(4H, m), 2.56–2.48(4H, m), 2.68–2.61(1H, m), 2.91–2.80(3H, m), 3.15–3.02 (1H, m), 3.71–3.57(1H, m), 4.23–4.14(1H, m), 4.40(1H, septet), 4.50 (3H, s), 4.75–4.57(1H, m), 6.91(1H, dd), 7.12(1H, d), 7.40(1H, d), 7.66(2H, d), 8.04(2H, d) |
| 36 (I) | δ(CD₃OD) 1.62–1.42(2H, m), 1.94–1.72(5H, m), 2.11–1.98(3H, m), 2.61–2.52(2H, m), 2.95–2.82(3H, m), 3.15(1H, t), 3.68–3.63(1H, m), 4.42(1H, septet), 4.71–4.67(2H, m), 6.91(1H, dd), 7.11(1H, d), 7.40(1H, d), 7.60(2H, d), 7.86(2H, d) |
| 37 (I) | δ(CD₃OD) 2.06–1.76(3H, m), 2.45–2.12(5H, m), 3.05–2.88(1H, m), 3.42–3.25(3H, m), 3.71–3.50(2H, m), 3.93–3.74(2H, m), 4.63(1H, septet), 4.94–4.82(2H, m), 7.03–6.95(1H, m), 7.24(1H, dd), 7.47–7.42(1H, m), 7.71–7.66(1H, m), 7.78(1H, td), 7.90–7.86(2H, m) |
| 149 (I) | δ(CDCl₃) 1.50–1.27(2H, m), 1.90–1.75(5H, m), 2.02–1.92(2H, m), 2.56–2.39(4H, m), 2.63(1H, t), 2.81–2.72(2H, m), 3.09–3.01(3H, m), 3.82(3H, s), 3.91(1H, d), 4.25(1H, septet), 4.67(1H, d), 6.75(1H, dd), 6.99(1H, d), 7.31(1H, dd), 7.45(2H, d), 7.90(2H, d) |
| 203 (I) | δ(DMSO-D6) 1.61–1.44(2H, m), 2.24–2.01(4H, m), 2.61–2.53(2H, m), 3.16–2.99(2H, m), 3.60–3.30(5H, m), 3.67(2H, s), 3.77(3H, s), 4.13(1H, d), 4.53(1H, d), 4.69–4.60(1H, m), 7.05(1H, ddd), 7.14(1H, d), 7.42–7.25(3H, m), 7.55(2H, dd), 10.98–10.78(3H, m) |
| 205 (I) | δ((CD₃)₂CO) 1.26(2H, quintet), 1.76–1.58(4H, m), 1.98–1.90(2H, m), 2.42–2.35(2H, m), 2.58–2.45(2H, m), 2.81–2.71(2H, m), 3.00(1H, t), 3.70(2H, s), 4.00(1H, d), 4.39(2H, septet), 4.51(1H, d), 6.92(1H, dd), 7.07–7.01(2H, m), 7.13(1H, d), 7.30–7.25(2H, m), 7.40(1H, d) |
| 220 (I) | δ(DMSO-D6) 1.58–1.44(2H, m), 2.28–1.97(5H, m), 2.59–2.53(2H, m), 3.18–2.93(3H, m), 3.34–3.25(1H, m), 3.51–3.36(2H, m), 3.66–3.56(2H, m), 4.11(1H, d), 4.53(1H, d), 4.64(1H, septet), 6.92–6.82(2H, m), 6.99(1H, d), 7.10–7.03(1H, m), 7.36(1H, dd), 7.55(1H, ddd), 10.99–10.87(1H, m) |
| 225 (I) | δ((CD₃)₂CO) 1.71–1.51(2H, m), 2.13–2.08(2H, m), 2.40–2.21(3H, m), 2.61–2.54(1H, m), 3.05(1H, t), 3.55–3.15(6H, m), 3.69–3.61(2H, m), 4.16(1H, d), 4.76–4.63(1H, m), 4.91–4.86(1H, m), 6.78–6.76(2H, m), 7.12–7.02(3H, m), 7.32(1H, dd), 7.51(1H, dd) |
| 244 (I) | δ(DMSO-D6) 1.55–1.42(2H, m), 2.25–1.96(6H, m), 2.66–2.54(2H, m), 3.14–2.96(1H, m), 3.32–3.26(1H, m), 3.51–3.35(3H, m), 3.62(3H, s), 3.71–3.64(2H, m), 3.74(6H, s), 4.14(1H, d), 4.54(1H, d), 4.66 4.58(1H, m), 6.53(2H, s), 7.04(1H, dd), 7.35(1H, d), 7.54(1H, tt) |
| 253 (I) | δ(CDCl₃) 1.47–1.19(2H, m), 2.00–1.76(6H, m), 2.62–2.37(4H, m), 2.80–2.70(2H, m), 2.98(1H, t), 3.65(2H, s), 3.88(3H, s), 3.92–3.89(1H, m), 4.25(1H, septet), 4.68(1H, d), 6.77–6.72(1H, m), 6.89(1H, d), 6.94–6.92(2H, m), 7.01–6.96(2H, m), 7.30(1H, dd) |
| 258 (I) | δ(DMSO-D6) 1.40–1.26(3H, m), 1.78–1.59(5H, m), 1.98–1.92(1H, m), 2.17(3H, s), 2.21(3H, s), 2.45–2.37(2H, m), 2.60–2.48(3H, m), 3.01(1H, t), 3.70–3.57(2H, m), 3.89(1H, d), 4.39(1H, septet), 4.55(1H, d), 7.00(1H, d), 7.13(1H, d), 7.41(1H, d), 7.95–7.89(3H, m) |
| 267 (I) | δ(CDCl₃) 1.74–1.61(2H, m), 2.21–2.09(3H, m), 2.32–2.25(1H, m), 2.48(1H, t), 2.67–2.53(2H, m), 2.89(1H, t), 3.31–3.05(5H, m), 3.71(4H, m), 3.82(2H, s), 4.08(1H, d), 4.59–4.53(1H, m), 4.94(1H, d), 6.89 (1H, dd), 6.93(1H, d), 6.97(1H, d), 7.34(1H, d), 7.40(1H, d), 7.58–7.54(1H, m) |
| 268 (I) | δ(CDCl₃) 1.24(1H, dq), 1.41(1H, dq), 1.88–1.72(4H, m), 2.00–1.91(2H, m), 2.53–2.37(3H, m), 2.59(1H, dt), 2.78–2.70(2H, m), 2.98(1H, t), 3.73(2H, s), 3.89(1H, d), 4.24(1H, septet), 4.68(1H, d), 6.74(1H, dd), 7.03–6.91(4H, m), 7.29–7.25(1H, m), 7.30(1H, d) |
| 272 (I) | δ(CDCl₃) 1.18(1H, dq), 1.40(1H, dq), 1.86–1.68(4H, m), 2.00–1.91(2H, m), 2.43–2.35(2H, m), 2.48(1H, td), 2.57(1H, dt), 2.77–2.68(2H, m), 2.95(1H, dt), 3.74(2H, s), 3.91(1H, d), 4.23(1H, septet), 4.69(1H, d), 6.74(1H, dd), 6.98(1H, d), 7.35–7.23(6H, m) |
| 274 (I) | δ(DMSO-D6) 1.74–1.59(5H, m), 1.77(3H, dq), 2.65–2.36(4H, m), 2.86–2.74(6H, m), 2.95(1H, t), 3.74(3H, s), 3.93(1H, d), 4.40(1H, septet), 4.53(1H, d), 6.73–6.70(1H, m), 6.80–6.78(2H, m), 6.93(1H, dd), 7.18–7.13(2H, m), 7.41(1H, d) |
| 276 (I) | δ((CD₃)₂CO) 1.63–1.51(2H, m), 2.02–1.98(2H, m), 2.21–2.15(2H, m), 2.58–2.31(4H, m), 2.96(1H, t), 3.40–3.03(4H, m), 3.60–3.49(2H, m), 3.72(3H, s), 4.02(1H, d), 4.63–4.55(1H, m), 4.77–4.72(1H, m), 6.76(1H, t), 6.84(1H, d), 6.96–6.93(1H, m), 7.03(1H, d), 7.11–7.07(1H, m), 7.16–7.15(1H, m), 7.37–7.31(1H, m) |
| 286 (I) | δ(CD₃OD) 1.90–1.63(2H, m), 2.49–2.05(6H, m), 3.28–2.87(7H, m), 3.84–3.44(5H, m), 4.69–4.56(1H, m), 4.85–4.78(2H, m), 7.04–6.94(1H, m), 7.28–7.21(1H, m), 7.45(1H, t), 7.60–7.55(3H, m), 7.64–7.61(1H, m), 7.66(1H, t), 7.77–7.73(2H, m), 7.85–7.81(2H, m) |
| 291 (I) | δ(CD₃OD) 1.98–1.71(3H, m), 2.46–2.11(5H, m), 3.18–2.98(1H, m), 3.45–3.26(2H, m), 3.70–3.46(4H, m), 3.86(3H, s), 4.66–4.56(1H, m), 4.84–4.80(2H, m), 7.04–6.94(3H, m), 7.27–7.20(1H, m), 7.47–7.42(3H, m) |
| 293 (I) | δ(CD₃OD) 1.88–1.73(2H, m), 2.22–1.92(5H, m), 2.31(1H, d), 2.87–2.79(1H, m), 3.06–2.97(1H, m), 3.17(3H, s), 3.57–3.31(5H, m), 4.55–4.44(1H, m), 4.73–4.65(2H, m), 6.92–6.82(1H, m), 7.12(1H, td), 7.40–7.31(2H, m), 7.63(1H, dt), 7.75–7.68(1H, m), 7.99(1H, dt) |
| 294 (I) | δ(CD₃OD) 1.98–1.70(2H, m), 2.45–2.08(6H, m), 2.97(1H, t), 3.21(3H, s), 3.41–3.21(3H, m), 3.72–3.49(3H, m), 4.67–4.56(1H, m), 4.95–4.81(2H, m), 7.03–6.94(1H, m), 7.27–7.20(1H, m), 7.47–7.42(1H, m), 7.74–7.62(1H, m), 8.02(1H, ddd), 8.13(1H, dd) |
| 295 (I) | δ(CD₃OD) 2.04–1.74(4H, m), 2.36–2.12(4H, m), 2.48–2.40(1H, m), 3.03–2.87(1H, m), 3.43–3.15(3H, m), 3.80–3.47(3H, m), 4.68–4.58(1H, m), 4.85–4.80(2H, m), 5.13(2H, s), 7.03–6.96(1H, m), 7.27–7.21(1H, m), 7.46–7.42(1H, m), 7.63–7.56(3H, m), 7.79–7.69(4H, m), 8.12(1H, d) |
| 296 (I) | δ(CD₃OD) 2.46–1.75(8H, m), 2.96(1H, t), 3.32(2H, s), 3.72–3.19(4H, m), 3.97–3.92(1H, m), 4.69–4.56(1H, m), 4.98–4.79(2H, m), 7.03–6.94(1H, m), 7.24(1H, d), 7.69–7.35(10H, m) |
| 297 (I) | δ(CD₃OD) 1.66–1.51(2H, m), 1.89–1.69(3H, m), 2.08–1.96(3H, m), 2.71–2.50(3H, m), 3.01–2.81(3H, m), 3.24–3.10(1H, m), 3.84–3.71(1H, m), 4.46–4.38(1H, m), 4.79–4.67(1H, m), 6.92(1H, dd), 7.14(1H, d), 7.41(1H, d), 7.81(1H, dd), 8.39(1H, d), 8.71(1H, s) |
| 298 (I) | δ(CD₃OD) 1.33(3H, t), 1.62–1.41(2H, m), 1.95–1.74(3H, m), 2.11–1.98(3H, m), 2.73–2.52(3H, m), 2.95–2.79(3H, m), 3.03(2H, q), 3.26–3.09(1H, m), 3.93–3.78(1H, m), 4.48–4.39(1H, m), 4.78–4.56(1H, m), 6.91(1H, dd), 7.11(1H, d), 7.42–7.34(5H, m) |
| 299 (I) | δ(CD₃OD) 1.99–1.72(3H, m), 2.36–2.11(4H, m), 2.44(1H, d), 3.06–2.87(1H, m), 3.42–3.23(4H, m), 3.71–3.46(4H, m), 3.95–3.77(1H, m), 4.67–4.55(1H, m), 4.84–4.80(1H, m), 7.03–6.94(1H, m), 7.27–7.20(1H, m), 7.47–7.43(1H, m), 7.66–7.61(2H, m), 7.87–7.81(2H, m) |
| 300 (I) | δ(CD₃OD) 1.96–1.72(3H, m), 2.33–2.09(4H, m), 2.46–2.41(1H, m), 3.02–2.87(1H, m), 3.43–3.22(3H, m), 3.72–3.47(3H, m), 3.93–3.78(1H, m), 4.66–4.56(1H, m), 4.84–4.80(1H, m), 7.03–6.94(1H, m), 7.28–7.21(1H, m), 7.47–7.43(1H, m), 7.59(2H, d), 7.83(2H, d) |
| 301 (I) | (500.076MHz, DMSO-D6) δ 1.33–1.44(m, 2H), 1.55–1.60(m, 2H), 1.66–1.73(m, 1H), 1.78–1.86(m, 1H), 1.91(s, 3H), 1.91–1.96(m, 2H), 2.05(s, 3H), 2.39(t, 2H), 2.55(t, 1H), 2.74–2.79(m, 3H), 2.94–3.04(m, 1H), 3.56–3.66(m, 1H), 4.42(septet, 1H), 4.45–4.52(m, 1H), 6.98(dd, 2H), 7.02(d, 2H), 7.25(d, 1H), 7.35(t, 1H), 7.49(d, 1H), 7.58(d, 1H), 7.66(s, 1H) |
| 302 (I) | (500.076MHz, DMSO-D6) δ 1.36(dq, 2H), 1.54–1.60(m, 2H), 1.72–1.75(m, 2H), 1.91(s, 3H), 1.91–1.95(m, 2H), 2.05(s, 3H), 2.39(t, 2H), 2.74–2.78(m, 2H), 2.80–2.87(m, 1H), |

TABLE VI-continued

| Compound (Table no.) | NMR data |
|---|---|
| | 4.05–4.19(m, 2H), 4.42(septet, 1H), 5.22(s, 2H), 6.58(d, 1H), 6.97–6.99(m, 2H), 7.00(s,1H), 7.25(d, 1H), 7.49(d, 1H) |
| 303 (I) | (500.076MHz, DMSO-D6) δ 1.54–1.63(m, 4H), 1.69–1.82(m, 4H), 1.91–1.96(m, 2H), 1.91(s, 3H), 2.35–2.44(m, 2H), 2.73–3.04(m, 7H), 4.39–4.46(m, 2H), 6.48–6.49(m, 1H), 6.98(d, 1H), 7.02–7.07(m, 3H), 7.26(s, 1H), 7.34(t, 1H), 7.49(d, 1H), 7.62(d, 1H) |
| 304 (I) | (500.076MHz, DMSO-D6) δ 1.33(t, 3H), 1.36–1.43(m, 2H), 1.54–1.60(m, 2H), 1.70–1.80(m, 2H), 1.91–1.96(m, 2H), 1.91(s, 3H), 2.39(t, 2H), 2.51–2.55(m, 1H), 2.74–2.79(m, 2H), 3.79(s, 3H), 4.01–4.05(m, 1H), 4.02(q, 2H), 4.42(septet, 1H), 4.47–4.53(m, 1H), 6.94(s, 2H), 6.97–6.99(m, 2H), 7.25(d, 1H), 7.49(d, 1H) |
| 305 (I) | (500.076MHz, DMSO-D6) δ 1.37–1.46(m, 2H), 1.54–1.61(m, 2H), 1.67–1.83(m, 2H), 1.91–1.96(m, 2H), 1.91(s, 3H), 2.40(t, 2H), 2.53–2.58(m, 1H), 2.74–2.80(m, 2H), 2.99–3.10(m, 1H), 3.63–3.74(m, 1H), 4.42(septet, 1H), 4.46–4.54(m, 1H), 6.29–6.30(m, 1H), 6.98(dd, 1H), 7.25(d, 1H), 7.43–7.44(m, 1H), 7.48(t, 3H), 7.64(d, 1H) |
| 306 (I) | (500.076MHz, DMSO-D6) δ 1.22–1.40(m, 2H), 1.54–1.61(m, 2H), 1.75(t, 2H), 1.91–1.96(m, 2H), 2.38(t, 2H), 2.53–2.60(m, 1H), 2.71–2.77(m, 2H), 3.03(t, 1H), 3.79(s, 2H), 3.98–4.03(m, 1H), 4.36–4.40(m, 1H), 4.40–4.45(m, 1H), 6.98(dd, 1H), 7.25(d, 1H), 7.50(d, 1H), 8.34(s, 1H), 8.57(d, 1H) |
| 307 (I) | (500.076MHz, DMSO-D6) δ 1.17–1.31(m, 2H), 1.53–1.59(m, 2H), 1.69(t, 2H), 1.88–1.94(m, 2H), 2.35(t, 2H), 2.45–2.52(m, 1H), 2.68–2.74(m, 2H), 2.95(t,1H), 3.50(s, 2H), 3.59(s, 3H), 4.06–4.10(m, 1H), 4.36–4.43(m, 2H), 6.88(s, 1H), 6.97(dd, 1H), 7.25(d, 1H), 7.45(s, 1H), 7.49(d, 1H) |
| 308 (I) | (500.076 MHz, DMSO-D6) δ 1.03(dq, 1H), 1.18(dq, 1H), 1.49–1.58(m, 3H), 1.68(d, 1H), 1.83–1.90(m, 1H), 1.91(s, 3H), 2.23–2.30(m, 2H), 2.41–2.49(m, 3H), 2.57–2.67(m, 2H), 2.90(t, 1H), 3.66(q, 2H), 4.01(d, 1H), 4.38(septet, 1H), 4.43(d, 1H), 6.58(dd, 1H), 6.88(d, 1H), 6.96(dd, 1H), 7.07(d, 1H), 7.12(d, 1H), 7.23(d, 1H), 7.49(d, 1H), 8.58(s, 1H) |
| 309 (I) | (500.076MHz, DMSO-D6) δ 1.46–1.56(m, 2H), 1.89–1.98(m, 2H), 2.03–2.18(m, 4H), 2.23(d, 1H), 2.55–2.61(m, 1H), 3.02–3.17(m, 4H), 3.42–3.51(m, 1H), 3.98(s, 2H), 4.16(d, 1H), 4.54(d, 1H), 4.60–4.66(m, 1H), 6.93–6.97(m, 1H), 7.01–7.09(m, 1H), 7.15(s, 1H), 7.25(s, 1H), 7.34–7.38(m, 1H), 7.54–7.58(m, 1H) |
| 310 (I) | (500.076MHz, DMSO-D6) δ 1.11(t, 3H), 1.39–1.48(m, 2H), 1.55–1.60(m, 2H), 1.65–1.72(m, 1H), 1.81–1.87(m, 1H), 1.90–1.95(m, 2H), 1.90(s, 3H), 2.39(t, 2H), 2.53–2.59(m, 1H), 2.74–2.83(m, 2H), 3.03–3.10(m, 1H), 3.36(q, 2H), 3.47–3.55(m, 1H), 4.42(septet, 1H), 4.46–4.54(m, 1H), 6.98(dd, 1H), 7.25(d, 1H), 7.49(d, 1H), 7.72–7.78(m, 2H), 7.86(s, 1H), 7.96(d, 1H) |
| 311 (I) | (500.076MHz, DMSO-D6) δ 0.92(t, 3H), 1.40–1.49(m, 2H), 1.55–1.64(m, 2H), 1.57(sextet, 2H), 1.65–1.73(m, 1H), 1.81–1.88(m, 1H), 1.91(s, 3H), 1.91–1.96(m, 2H), 2.36–2.44(m, 2H), 2.54–2.61(m, 1H), 2.73–2.84(m, 2H), 3.02–3.11(m, 1H), 3.45–3.53(m, 1H), 4.40–4.46(m, 1H), 4.50–4.54(m, 1H), 6.98(dd, 1H), 7.25(d, 1H), 7.49(d, 1H), 7.72–7.78(m, 2H), 7.86(s, 1H), 7.96(d, 1H) |
| 312 (I) | (500.076MHz, DMSO-D6) δ 0.98(d, 6H), 1.39–1.49(m, 2H), 1.54–1.61(m, 2H), 1.64–1.71(in. 1H), 1.81–1.87(m, 1H), 1.90–1.95(m, 2H), 1.91(s, 3H), 2.02(septet, 1H), 2.39(t, 2H), 2.53–2.59(m, 1H), 2.74–2.79(m, 2H), 3.03–3.11(m, 1H), 3.45–3.52(m, 1H), 4.42(septet, 1H), 4.47–4.53(m, 1H), 6.98(dd, 1H), 7.25(d, 1H), 7.49(d, 1H), 7.71–7.77(m, 2H), 7.88(s, 1H), 7.98(d, 1H) |
| 313 (I) | (500.076MHz, DMSO-D6) δ 1.41–1.53(m, 2H), 1.54–1.62(m, 2H), 1.66–1.74(m, 1H), 1.84–1.89(m, 1H), 1.91–1.96(m, 2H), 1.91(s, 3H), 2.36–2.44(m, 2H), 2.54–2.62(m, 1H), 2.73–2.87(m, 4H), 3.10(t, 1H), 3.50(s, 3H), 3.52(s, 3H), 3.52–3.58(m, 1H), 4.40–4.46(m, 1H), 4.48–4.54(m, 1H), 6.97–7.00(m, 1H), 7.23–7.29(m, 1H), 7.50(d, 1H), 8.06(d, 1H), 8.16(s, 1H), 8.29(d, 1H) |
| 314 (I) | (500.076MHz, DMSO-D6) δ 1.34(t, 3H), 1.35–1.41(m, 2H), 1.54–1.60(m, 2H), 1.74(d, 2H), 1.90–1.96(m, 2H), 1.90(s, 3H), 2.39(t, 2H), 2.50–2.55(m, 1H), 2.73–2.79(m, 1H), 2.80–2.89(m, 1H), 4.01(q, 2H), 4.08–4.19(m, 2H), |
| 315 (I) | 4.42(septet, 2H), 5.06(s, 2H), 6.62(d, 1H), 6.77(d, 1H), 6.81(s, 2H), 6.98(dd, 1H), 7.25(d, 1H), 7.49(d, 1H) (DMSO-D6) δ 1.53–1.82(m, 2H), 2.02–2.36(m, 5H), 2.60–2.67(m, 1H), 3.07–3.15(m, 2H), 3.31–3.38(m, 1H), 3.43–3.53(m, 2H), 4.12–4.19(m, 4H), 4.51(d, 1H), 4.68(septet, 1H), 4.85(s, 1H), 7.06(dd, 1H), 7.37(dd, 1H), 7.56(t, 1H), 7.94(d, 2H), 8.86(d, 1H), 11.47(s, 1H) |
| 316 (I) | (DMSO-D6) δ 1.58–2.28(m, 4H), 2.67–2.84(m, 1H), 2.91–3.04(m, 2H), 2.97(s, 3H), 3.06–3.26(m, 2H), 3.24–3.42(m, 1H), 3.44–3.67(m, 3H), 3.57(s, 3H), 4.55–4.77(m, 2H), 4.83(s, 1H), 7.00–7.09(m, 2H), 7.35–7.58(m, 5H) |
| 317 (I) | (DMSO-D6) δ 1.52(dq, 2H), 1.74–1.92(m, 2H), 1.93–2.04(m, 4H), 2.42–2.50(m, 2H), 2.55(m, 1H), 2.77–2.85(m, 2H), 2.87–2.96(m, 2H), 4.22–4.30(m, 3H), 6.69–6.74(m, 2H), 6.76(d, 1H), 6.99(d, 1H), 7.07(dd, 1H), 7.16(dt, 1H), 7.29(s, 2H), 7.32(s, 1H) |
| 318 (I) | (DMSO-D6) δ 1.7 1(m, 2H), 2.18(m, 3H), 2.70(s, 3H), 3.02(m, 1H), 3.15(m, 2H), 3.32(m, 3H), 3.50(m, 2H), 4.63(m, 1H), 7.05(ddd, 1H), 7.36(m, 4H), 7.56(t, 1H), 7.66(d, 1H), 8.11(s, 1H), 8.37(d, 1H) |
| 319 (I) | (DMSO-D6) δ 1.40(m, 2H), 1.57(m, 2H), 1.79(m, 2H), 1.90(m, 2H), 2.40(m, 2H), 2.58(m, 1H), 2.79(m, 2H), 2.87(m, 2H), 4.30(d, 2H), 4.43(m, 1H), 6.97(dd, 1H), 7.13(m, 2H), 7.25(d, 1H), 7.43(d, 1H), 7.49(d, 1H), 7.65(m, 2H) |
| 321 (I) | (DMSO-D6) δ 1.67–1.78(m, 2H), 1.95–2.09(m, 3H), 2.18–2.27(m, 2H), 2.44(d, 3H), 2.77–2.88(m, 1H), 3.08–3.19(m, 3H), 3.33–3.52(m, 5H), 3.59–3.67(m, 1H), 4.60–4.68(m, 1H), 4.84(s, 1H), 7.05(ddd, 1H), 7.14–7.27(m, 1H), 7.37(dd, 1H), 7.55(t, 1H), 7.61(q, 1H), 7.70–7.71(m, 1H), 7.78–7.80(m, 1H), 7.86–7.89(m, 1H) |
| 322 (I) | (DMSO-D6) δ 1.65–1.80(m, 2H), 1.99–2.09(m, 2H), 2.19–2.30(m, 3H), 2.77–2.90(m, 1H), 3.07–3.21(m, 3H), 3.30–3.37(m, 3H), 3.47–3.57(m, 2H), 3.59–3.71(m, 1H), 4.59–4.69(m, 1H), 4.82–4.86(m, 1H), 7.05(ddd, 1H), 7.37(dd, 1H), 7.49(s, 2H), 7.55(t, 1H), 7.64–7.69 (m, 2H), 7.84–7.86(m, 1H), 7.92(td, 1H) |
| 323 (I) | (DMSO-D6) δ 1.64–1.78(m, 2H), 1.99–2.09(m, 2H), 2.17–2.29(m, 3H), 2.70–2.85(m, 1H), 3.04–3.19(m, 3H), 3.28–3.38(m, 3H), 3.31(s, 3H), 3.46–3.55(m, 2H), 3.66(t, 2H), 4.12(t, 2H), 4.56–4.68(m, 1H), 4.81–4.86(m, 1H), 6.94–6.97(m, 2H), 7.04(dd, 1H), 7.05(ddd, 1H), 7.34–7.39(m, 2H), 7.55(t, 1H) |
| 324 (I) | (CDCl₃) δ 1.45(s, 9H), 1.48–1.67(m, 4H), 1.75–1.85(m, 2H), 1.90–2.03(m, 3H), 2.42–2.51(m, 2H), 2.56(m, 1H), 2.71–2.84(m, 3H), 2.91–3.06(m, 1H), 3.54(q, 2H), 3.75–3.88(m, 1H), 4.03(t, 2H), 4.27(septet, 1H), 4.68–4.82(m, 1H), 4.93–5.01(m, 1H), 6.75(dd, 1H), 6.90–7.00(m, 3H), 7.25–7.32(m, 3H) |
| 325 (I) | (DMSO-D6) δ 1.70–1.84(m, 2H), 2.00–2.09(m, 2H), 2.20–2.29(m, 3H), 2.81–2.91(m, 1H), 3.09–3.21(m, 3H), 3.28–3.38(m, 3H), 3.48–3.57(m, 2H), 3.61–3.70(m, 1H), 4.61–4.72(m, 1H), 4.82–4.86(m, 1H), 7.05(ddd, 1H), 7.14–7.27(m, 1H), 7.37(dd, 1H), 7.56(t, 1H), 7.76–7.79(m, 1H), 8.51(s, 1H), 8.80(d, 1H) |
| 326 (I) | (DMSO-D6) δ 1.70–1.78(m, 2H), 2.00–2.09(m, 2H), 2.18–2.26(m, 3H), 3.05–3.17(m, 2H), 3.24–3.40(m, 2H), 3.97–4.06(m, 2H), 4.44–4.52(m, 2H), 4.59–4.70(m, 2H), 4.73(s, 2H), 4.81–4.86(m, 1H), 4.91–4.93 (m, 2H), 6.90–6.93(m, 1H), 6.96–7.04(m, 1H), 7.07–7.11(m, 1H), 7.17–7.20(m, 1H), 7.34–7.43(m, 2H), 7.52–7.55(m, 1H) |
| 327 (I) | (CDCl₃) δ 1.52–1.63(m, 4H), 1.77–1.86(m, 2H), 1.92–2.03(m, 4H), 2.44–2.50(m, 2H), 2.58–2.67(m, 1H), 2.77–2.83(m, 3H), 3.05(bs, 1H), 3.36(s, 3H), 4.26–4.31(m, 2H), 6.74–6.77(m, 1H), 6.99–7.01(m, 1H), 7.30–7.33(m, 1H), 7.47(s, 1H) |
| 328 (I) | (CDCl₃) δ 1.43–1.67(m, 4H), 1.73–1.91(m, 4H), 1.95–2.02(m, 2H), 2.42–2.50(m, 2H), 2.52–2.62(m, 1H), 2.77–2.85(m, 3H), 2.92(bs, 1H), 3.06(m, 3H), 4.23–4.30(m, 1H), 5.26(s, 2H), 6.73–6.79(m, 2H), 6.99–7.00(m, 1H), 7.29–7.32(m, 1H), 7.47–7.50(m, 1H), 7.82–7.82(m, 1H) |
| 329 (I) | (CDCl₃) δ 1.50–1.69(m, 4H), 1.77–1.86(m, 2H), 1.92–2.02(m, 4H), 2.45–2.49(m, 2H), 2.59–2.65(m, 1H), 2.79–2.83(m, 3H), 3.02(bs, 1H), 3.39(s, 3H), 4.26–4.30(m, |

TABLE VI-continued

| Compound (Table no.) | NMR data |
|---|---|
| | 2H), 5.88(bs, 1H), 6.74–6.77(m, 1H), 6.99–7.00(m, 1H), 7.30–7.32(m, 1H), 7.46(bs, 1H), 7.65(s, 1H) |
| 330 (I) | (DMSO-D6) δ 1.73–3.63(m, 17H), 4.57–4.70(m, 1H), 7.01–7.88(m, 7H) |
| 331 (I) | (DMSO-D6) δ 1.21(d, 6H), 1.37–2.03(m, 8H), 2.33–3.42(m, 7H), 4.15–4.19(m, 1H), 4.37–4.45(m, 1H), 5.89(s, 2H), 6.96–8.34(m, 4H) |
| 332 (I) | (DMSO-D6) δ 1.41–1.94(m, 8H), 2.37–2.78(m, 8H), 3.32(s, 3H), 4.38–4.46(m, 1H), 6.96–7.78(m, 5H) |
| 333 (I) | (CDCl₃) δ 1.80–1.96(m, 5H), 2.38(s, 4H), 2.41–3.00(m, 12H), 3.57–3.60(m, 1H), 4.26(s, 1H), 4.73–4.76(m, 1H), 6.73–7.32(m, 3H) |
| 334 (I) | (DMSO-D6) δ 1.33–1.93(m, 8H), 2.33–3.27(m, 7H), 4.39–4.45(m, 1H), 4.49–4.53(m, 1H), 6.96–8.98(m, 5H) |
| 335 (I) | (CDCl₃) δ 1.16–1.30(m, 1H), 1.33–1.48(m, 1H), 1.76–2.75(m, 12H), 2.96–3.05(m, 1H), 3.72(s, 2H), 3.89–3.93(m, 1H), 4.21–4.30(m, 1H), 4.66–4.71(m, 1H), 6.72–7.32(m, 7H) |
| 336 (I) | (DMSO-D6) δ 1.37–2.83(m, 17H), 4.38–4.47(m, 1H), 5.76(s, 1H), 6.96–7.96(m, 6H) |
| 337 (I) | (DMSO-D6) δ 1.33–1.99(m, 8H), 2.36–2.60(m, 4H), 2.73–2.82(m, 2H), 2.94(s, 3H), 2.98–3.09(m, 1H), 3.55–3.66(m, 1H), 4.38–4.46(m, 1H), 4.56(s, 2H), 6.96–7.00(m, 1H), 7.23–7.27(m, 1H), 7.41–7.52(m, 5H) |
| 338 (I) | (DMSO-D6) δ 1.35–1.99(m, 8H), 2.37–2.46(m, 2H), 2.55–2.63(m, 2H), 2.73–2.85(m, 2H), 2.92(s, 3H), 2.97–3.06(m, 1H), 3.55–3.65(m, 1H), 4.41–4.49(m, 1H), 4.56(s, 2H), 6.96–7.01(m, 1H), 7.25–7.27(m, 1H), 7.39–7.52(m, 5H) |
| 1(III) | δ(DMSO-D6) 1.57–1.36(2H, m), 2.25–1.87(5H, m), 2.45–2.33(2H, m), 3.16–2.97(2H, m), 3.37–3.17(4H, m), 3.45–3.40(1H, m), 4.12(0H, t), 4.53(1H, d), 4.67–4.58(1H, m), 4.84–4.77(1H, m), 5.45(1H, d), 7.03(1H, ddd), 7.19(2H, t), 7.42–7.33(3H, m), 7.55(1H, m), 10.59–10.38(1H, m) |
| 2(III) | δ(DMSO-D6) 1.60–1.36(2H, m), 2.27–1.93(5H, m), 2.61–2.57(1H, m), 2.90–2.73(1H, m), 3.13–2.94(2H, m), 3.41–3.23(3H, m), 4.17–3.85(2H, m), 4.68–4.47(2H, m), 4.84–4.77(1H, m), 5.43(1H, d), 7.09–6.99(1H, m), 7.40–7.27(6H, m), 7.55(1H, t), 11.13–10.92(1H, m) |
| 3(III) | δ(DMSO-D6) 1.27–1.07(1H, m), 1.57–1.36(1H, m), 2.24–1.89(5H, m), 2.66–2.56(1H, m), 2.93–2.79(1H, m), 3.16–3.00(2H, m), 3.51–3.39(2H, m), 4.18(1H, t), 4.67–4.46(2H, m), 4.84–4.78(1H, m), 5.51–5.43(1H, m), 6.05(1H, s), 7.04(1H, dd), 7.24–7.17(1H, m), 7.48–7.33(3H, m), 7.55(1H, dd), 10.41–10.23(1H, m) |

TABLE VII

| Compound (Table) | MS | MP (° C.) | ¹HNMR | Can be prepared using: |
|---|---|---|---|---|
| 3 (IV) | 495 (M + H) | 181–182 | (DMSO-D6) δ 1.2–2.8(bm, 14H), 3.1(bm, 1H), 3.35(s, 3H), 3.5(bm, 1H), 4.4(m, 1H), 4.5(bm, 1H), 6.82(dd, 1H), 7.1(dd, 1H), 7.4(t, 1H), 7.7(m, 2H), 7.9(s, 1H), 8.0(dd, 1H) | Example 12 |
| 2 (IV) | 495 (M + H) | 111–112 | (DMSO-D6) δ 1.6–2.3(bm, 8H), 3.0–3.6(bm, 8H), 3.3(s, 3H), 4.5–4.8(m, 2H), 6.9–7.1(m, 1H), 7.2–7.4(m, 2H), 7.8(m, 2H), 7.94(d, 1H), 8.03(d, 1H), 10.9(bm, 1H) | Example 12 and final product isolated as Hydrochloride by treatment with a solution of HCl in dioxan and evaporation |
| 7 (IV) | 459 (M + H) | 149–150 | (DMSO-D6) δ 1.2–3.7(bm, 16H), 3.75(s, 3H), 3.85(bm, 1H), 4.6(bm, 1H), 5.05(bm, 1H), 6.9(m, 4H), 7.78(m, 2H), 7.92(d, 1H), 8.05(m, 1H), 11.0 and 11.8(bm, 1H) | As for 2 (IV) above |
| 8 (IV) | 463 (M + H) | 126–127 | (DMSO-D6) δ 1.2–3.6(bm, 16H), 3.9(bm, 1H), 4.6 bm, 1H), 5.14(bm, 1H), 7.0(d, 2H), 7.38(d, 2H), 7.75(m, 2H), 7.9(m, 1H), 8.05(m, 1H), 11.3 and 11.95(bm, 1H) | As for 2 (IV) above |
| 9 (IV) | 497 (M + H) | 78–80 | (DMSO-D6) δ 1.2–4.0(bm, 17H), 4.6(bm, 1H), 5.2(bm, 1H), 7.0(dd, 1H), 7.3(m, 1H), 7.58(d, 1H), 7.78(d, 2H), 7.95(d, 1H), 8.05(m, 1H) 11.0 and 11.65(bm, 1H) | As for 2 (IV) above |
| 10 (IV) | 454 (M + H) | 78–80 | (DMSO-D6) δ 1.2–3.6(m, 17H), 4.25(bm, 1H), 4.98(m, 1H), 7.03(d, 2H), 7.72(m, 4H), 7.9(s, 1H), 8.0(m, 1H) | Example 12 |
| 11 (IV) | 465 (M + H) | 82–83 | (DMSO-D6) δ 1.2–3.4(m, 16H), 3.5(bm, 1H), 4.3(bm, 1H), 4.85(m, 1H), 6.7(m, 1H), 7.0(m, 1H), 7.3(q, 1H), 7.7(m, 2H), 7.9(s, 1H), 8.0(m, 1H) | Example 12 |
| 12 (IV) | 447 (M + H) | 64–65 | (DMSO-D6) δ 1.2–3.3(m, 16H), 3.45(bm, 1H), 4.25(m, 1H), 4.8(m, 1H), 6.9(m, 2H), 7.1(t, 2H), 7.75(m, 2H), 7.9 (s, 1H), 8.0(dd, 1H) | Example 12 |
| 13 (IV) | 500 (M + H) | 110–111 | (DMSO-D6) δ 1.2–4.8(bm, 24H), 6.95(dd, 2H), 7.5(m, 2H), 7.8(m, 2H), 7.95(s, 1H) 8.02(d. 1H), 9.85(d, 1H), 10.7(bm, 1H) | As for 2 (IV) above |
| 14 (IV) | 457 (M + H) | 140–142 | (DMSO-D6) δ 1.2–4.8(m, 24H), 6.86(bm, 2H), 7.02(m, 2H), 7.75(bm, 2H), 7.90(s, 1H), 8.03(m, 1H) | Example 12 |
| 15 (IV) | 491 (M + H) | 94–95 | (DMSO-D6) δ 1.2–4.8(bm, 24H). 6.8(bd, 1H), 7.0(bs, 1H), 7.3(d, 1H), 7.75(m, 2H), 7.9(s, 1H), 8.0(m, 1H) | Example 12 |
| 16 (IV) | 477 (M + H) | 150–152 | (DMSO-D6) δ 1.2–4.6(bm, 21H), 7.0(bm, 2H), 7.3(bm, 2H), 7.75(m, 2H), 7.9(s, 1H), 8.0(m, 1H) | Example 12. |
| 17 (IV) | 461 (M + H) | 219–220 | (DMSO-D6) δ 1.2–4.8(bm, 21H), 6.9–7.3(m, 4H), 7.75(m, 2H), 7.92(s, 1h), 8.02(m. 1H). | As for 2 (IV) above |
| 18 (IV) | 511 (M + H) | 104–105 | (DMSO-D6) δ 1.2–5.0(bm, 21H), 7.3(d, 1H)7.4(dd, 1H), 7.6(dd, 1H), 7.75(m, 2H), 7.95(s, 1H), 8.0(d, 1H), 9.5 and 9.7(bs, 1H) | Example 12 and final product isolated as trifluoroacetate by evaporation of Reverse Phase HPLC fractions. |
| 19 (IV) | 495 (M + H) | 76–77 | (DMSO-D6) δ 1.2–5.0(bm, 21H), 7.2(m, 1H), 7.3(m, 1H), 7.45(m, 1H), 7.75(m, 2H), 7.95(s, 1H), 8.05(m, 1H), 9.5(bm, 1H) | As for 18 (IV) above |
| 20 (IV) | 479 | 230–232 | (DMSO-D6) δ 1.2–3.7(bm, | As for 2 |

TABLE VII-continued

| Compound (Table) | MS | MP (° C.) | ¹HNMR | Can be prepared using: |
|---|---|---|---|---|
| (IV) | (M + H) | | 19H), 4.4–4.7(bm, 2H), 7.02(t, 1H), 7.3(m, 2H), 7.75(m, 2H), 7.95(s, 1H), 8.02(d, 1H) | (IV) above |
| 21 (IV) | 495 (M + H) | 69–70 | (DMSO-D6) 1.2–4.0(m, 19H), 4.4–4.8(m, 2H), 7.3(m, 2H), 7.5(m, 1H), 7.75(m, 2H), 7.98(s, 1H), 8.0(m, 1H), 9.5(bm, 1H) | As for 18 (IV) above |
| 22 (IV) | 475 (M + H) | 130–132 | (CDCl₃) δ 1.0–3.6(m, 19H), 3.7(s, 3H), 4.6(m, 2H), 6.6–6.9(m, 3H), 7.7(m, 2H), 8.0(m, 2H) | As for 2 (IV) above |
| 24 (IV) | 462 (M + H) | 72–73 | (DMSO-D6) 1.6(m, 2H), 1.8(m, 1H), 2.01(m, 4H), 2.3(m, 1H), 2.5(m, 2H), 2.9(m, 2H), 3.2(m, 2H), 3.4(m, 1H), 3.58(m, 2H), 3.8(s, 3H), 4.3(bs, 2H), 4.6 and 4.8(m, 1H), 6.7(d, 1H), 6.8–7.0(m, 3H), (m, 1H), 7.5(m, 1H), 9.5(bs, 1H) | Example 13 |
| 26 (IV) | 458 (M + H) | 111–112 | (DMSO-D6) δ 1.4–3.6(m, 17H), 3.8(2s, 6H), 4.2–4.5(m, 3H), 6.7(m, 2H), 6.82(m, 2H), 6.9–7.2(m, 2H) | Example 13 |
| 27 (IV) | 440 (M + H) | 73–75 | (DMSO-D6) δ 1.6–1.9(m, 3H), 2.0–2.3(m, 5H), 2.4–2.6(m, 2H), 2.9(m, 2H), 3.18(m, 2H), 3.4(m, 1H), 3.5(m, 2H), 3.7(s, 3H), 3.8(s, 3H), 4.2(bs, 2H), 4.4 and 4.6(2m, 1H), 6.7(d, 1H), 6.9(m, 5H), 7.0(d, 1H), 9.7(bm, 1H) | Example 13 |
| 28 (IV) | 462 (M + H) | 81–83 | (DMSO-D6) δ 1.6(m, 2H), 1.8(m, 1H), 2.05(m, 4H), 2.3(m, 1H), 2.5(m, 1H), 2.9(m, 2H), 3.2(m, 2H), 3.3(m, 2H), 3.4(m, 1H), 3.55(m, 2H), 3.8(s, 3H), 4.3(bs, 2H), 4.6 and 4.8(m, 1H), 6.62(d, 1H), 6.81(d, 1H), 6.9(s, 1H), 7.05(m, 1H), 7.35(m, 2H), 9.76(bm, 1H) | Example 13 |
| 29 (IV) | 424 (M + H) | 97–99 | (DMSO-D6) δ 1.4–2.6(m, 14H), 2.9(m, 2H), 3.2(m, 2H), 3.4(m, 1H), 3.55(m, 2H), 3.8(s, 3H), 4.3(bs, 2H), 4.5 and 4.7(m, 1H), 6.65(d, 1H), 6.9(m, 4H), 7.1(m, 1H), 9.5(bs, 1H) | Example 13 |
| 30 (IV) | 458 (M + H) | 78–79 | (DMSO-D6) δ 1.5–2.6(m, 13H), 2.3(s, 3H), 2.9(m, 2H), 3.2(m, 2H), 3.4(m, 1H), 3.55(m, 2H), 4.3(bs, 2H), 4.55 and 4.75(m, 1H), 6.62(d, 1H), 6.85(m, 3H), 7.0(dd, 1H), 7.32(t, 1H), 9.5(bs, 1H) | Example 13 |
| 31 (IV) | 444 (M + H) | 100–101 | (DMSO-D6) δ 1.6(m, 2H), 1.8(m, 1H), 2.0(m, 4H), 2.3(m, 1H), 2.5(m, 2H), 2.9(m, 2H), 3.18(m, 2H), 3.4(m, 1H), 3.5(m, 2H), 3.8(s, 3H), 4.2(bs, 2H), 4.6 and 4.8(m, 1H), 6.62(d, 1H), 6.8(m, 2H), 7.0(m, 2H), 7.36(m, 2H), 9.7(bs, 1H) | Example 13 |
| 32 (IV) | 428 (M + H) | 74–75 | (DMSO-D6) 1.6(m, 2H), 1.8(m, 1H), 2.0(m, 4H), 2.3(m, 1H), 2.5(m, 2H), 2.9(m, 2H), 3.2(m, 2H), 3.4(m, 1H), 3.5(m, 2H), 3.8(s, 3H), 4.2(bs, 2H), 4.5 and 4.7(m, 1H), 6.7(d, 1H), 6.85(d, 1H), 6.9(s, 1H), 7.02(m, 1H), 7.04(m, 1H), 7.18(m, 2H), 9.6(m, 1H) | Example 13 |
| 33 (IV) | 478 (M + H) | 117–119 | (DMSO-D6) δ 1.6–3.6(m, 17H), 3.8(s, 3H), 4.25(bs, 2H), 4.6 and 4.9(m, 1H), 6.6(d, 1H), 6.8(m, 2H), 7.3(m, 1H), | Example 13 |
| 34 (IV) | 462 (M + H) | 109–110 | (DMSO-D6) δ 1.6–3.6(m, 17H), 3.8(s, 3H), 4.25(bs, 2H), 4.55 and 4.85(m, 1H), 6.6(d, 1H), 6.8(m, 2H), 7.2(m, 1H), 7.3(m, 1H), 7.45(m, 1H), 9.5(bs, 1H) | Example 13 |
| 37 (IV) | 442 (M + H) | 89–90 | (DMSO-D6) δ 1.6–3.6(m, 20H), 3.8(s, 3H), 4.25(bs, 2H), 4.45 and 4.75(m, 1H), 6.6(d, 1H), 6.8(m, 2H), 7.0(m, 3H), 9.6(bs, 1H) | Example 13 |
| 38 (IV) | 471 (M + H) | 143–145 | (DMSO-D6) δ 1.6–3.6(m, 19H), 4.2–4.8(m, 2H), 7.0(m, 1H), 7.2(d, 1H), 7.22(s, 1H), 7.8(d, 1H), 8.5(d, 1H), 8.8(s, 1H) | As for 18 (IV) above |
| 39 (IV) | 475 (M + H) | 141–142 | (DMSO-D6) δ 1.6–3.6(m, 16H), 4.2–4.8(m, 2H), 6.9(m, 1H), 7.2(m, 1H), 7.5(m, 1H), 7.8(d, 1H), 8.5(d, 1H), 8.8(d, 1H) | As for 18 (IV) above |
| 41 (IV) | 471 (M + H) | 160–162 | (DMSO-D6) δ 1.6–3.6(m, 16H), 3.8(s, 3H), 4.2–4.8(m, 2H), 6.7(m, 1H), 6.9–7.2(m, 2H), 7.8(d, 1H), 8.5(d, 1H), 8.8(d, 1H) | As for 18 (IV) above |
| 42 (IV) | 453 (M + H) | 116–118 | (DMSO-D6) δ 1.6–3.6(m, 16H), 3.7(s, 3H), 4.2–4.8(m, 2H), 6.8–7.1(m, 3H), 7.82(d, 1H), 8.52(d, 1H), 8.8(d, 1H), 9.6(bs, 1H) | As for 18 (IV) above |
| 43 (IV) | 475 (M + H) | 109–110 | (DMSO-D6) δ 1.6–3.6(m, 16H), 4.2–4.8(m, 2H), 7.07(m, 1H), 7.35(m, 2H), 7.82(d, 1H), 8.52(d, 1H), 8.8(d, 1H), 9.6(bs, 1H) | As for 18 (IV) above |
| 44 (IV) | 437 (M + H) | 136–137 | (DMSO-D6) δ 1.6–3.2(m, 15H), 3.3(s, 3H), 3.6(m, 1H), 4.22(m, 1H), 4.5(m, 1H), 6.8(m, 2H), 7.10(d, 2H), 7.82(d, 1H), 8.52(d, 1H), 8.8(d, 1H) | Example 12 |
| 89 (IV) | 471 (M + H) | 100–102 | (DMSO-D6) δ 1.0–4.2(m, 21H), 6.0(m, 1H), 6.18(m, 1H), 6.42(m, 1H), 7.02(d, 1H), 7.6(d, 1H), 7.85(d, 1H) | As for 18 (IV) above |
| 47 (IV) | 441 (M + H) | 133–136 | (DMSO-D6) δ 1.6–4.8(m, 18H), 6.9–7.2(m, 4H), 7.82(d, 1H), 8.52(d, 1H), 8.8(d, 1H) | As for 18 (IV) above |
| 48 (IV) | 491 (M + H) | 105–106 | (DMSO-D6) δ 1.6–4.8(m, 18H), 6.3(m, 1H), 6.4(d, 1H), 6.58(s, 1H), 6.9(d, 1H), 7.52(d, 1H), 7.8(d, 1H) | As for 18 (IV) above |
| 49 (IV) | 475 (M + H) | 123–125 | (DMSO-D6) δ 1.6–4.8(m, 18H), 7.2(m, 1H), 7.3(m, 1H), 7.45(m, 1H), 7.82(d, 1H), 8.52(d, 1H), 8.8(d, 1H) | As for 18 (IV) above |
| 50 (IV) | 459 (M + H) | 93–94 | (DMSO-D6) δ 1.6–4.8(m, 18H), 7.05(m, 1H), 7.3(m, 2H), 7.82(d, 1H), 8.52(d, 1H), 8.8(d, 1H), 9.7(bm, 1H) | As for 18 (IV) above |
| 271 (IV) | 507 (M + H) | 102–103 | (DMSO-D6) δ 1.6–3.8(m, 16H), 3.3(s, 3H), 3.8(d, 3H), 4.4–4.7(m, 2H), 6.95(m, 1H), 7.1(m, 2H), 7.78(m, 2H), 7.95(s, 1H), 8.03(d, 1H) | Example 12 |
| 272 (IV) | 505 (M + H) | 97–98 | (DMSO-D6) δ 1.6–4.8(m, 27H), 7.1(s, 2H), 7.6(m, 2H), 7.95(s, 1H), 8.03(d, 1H) | As for 18 (IV) above |
| 273 | 511 | 110–112 | (DMSO-D6) δ 1.4–3.8(m, | As for 18 |

TABLE VII-continued

| Compound (Table) | MS | MP (° C.) | ¹HNMR | Can be prepared using: |
|---|---|---|---|---|
| (IV) | (M + H) | | 16H), 3.3(s, 3H), 4.4–5.0(m, 2H), 7.22(m, 2H), 7.3(m, 1H), 7.75(m, 2H), 7.95(s, 1H), 8.02(d, 1H) | (IV) above |
| 274 (IV) | 511 (M + H) | 114–115 | (DMSO-D6)6 1.4–3.8(m, 16H), 3.3(s, 3H), 4.4–5.0(m, 2H), 7.02(m, 1H), 7.4(m, 2H), 7.75(m, 2H), 7.95(s, 1H), 8.02(d, 1H) | Example 12 |
| 275 (IV) | 491 (M + H) | 88–89 | (DMSO-D6) δ 1.4–3.8(m, 16H), 2.25(s, 3H), 3.3(s, 3H), 4.2–4.8(m, 2H), 7.02(m, 2H), 7.22(m, 1H), 7.75(m, 2H), 7.95(s, 1H), 8.02(d, 1H) | Example 12 |
| 276 (IV) | 491 (M + H) | 182–183 | (DMSO-D6) δ 1.4–3.8(m, 16H), 2.25(s, 3H), 3.3(s, 3H), 4.4–4.6(m, 2H), 6.74(d, 1H), 7.02(s, 1H), 7.22(d, 1H), 7.75(m, 2H), 7.90(s, 1H), 8.0(d, 1H) | Example 12 |
| 277 (IV) | 499 (M + H) | 162–164 | (DMSO-D6) δ 1.6–3.8(m, 19H), 2.25(s, 3H), 3.3(s, 3H), 4.5–5.0(m, 2H), 7.14(t, 1H), 7.8(m, 4H), 7.95(m, 1H), 8.02(d, 1H), 10.9(bm, 1H) | As for 2 (IV) above |
| 278 (IV) | 528 (M + H) | 120–122 | (DMSO-D6) δ 1.5–5.0(m, 29H), 6.9–7.2(m, 4H), 7.75(m, 2H), 7.9(s, 1H), 8.02(d, 1H), 10.2(bs, 1H), 11.0–11.3(bm, 1H) | As for 2 (IV) above |
| 279 (IV) | 505 (M + H) | 97–99 | (DMSO-D6) δ 1.18(t, 3H), 1.6–3.7(m, 17H), 2.62(q, 2H), 3.3(s, 3H), 4.4–4.8(m, 1H), 6.8–7.1(m, 2H), 7.3(m, 1H), 7.75(m, 2H), 7.95(s, 1H), 8.02(m, 1H), 9.4(bs, 1H) | Example 12 |
| 280 (IV) | 494 (M + H) | 138–140 | (DMSO-D6) δ 1.8(m, 2H), 2.1–4.4(m, 14H), 3.3(s, 3H), 4.62(bm, 1H), 4.9 and 5.1(m, 1H), 7.65(m, 1H), 7.8(m, 2H), 7.85(m, 2H), (d, 1H), 8.01(d, 1H), 8.3(t, 1H), 9.0(t, 1H), 9.15(t, 1H), 10.35(bs, 1H), 11.5(bs, 1H) | As for 2 (IV) above |
| 281 (IV) | 499 (M + H) | 98–99 | (DMSO-D6) δ 1.2(s, 9H), 1.3–3.6(m, 20H), 4.5(m, 1H), 6.8(t, 1H), 6.9(d, 1H), 7.1(t, 1H), 7.2(d, 1H), 7.7(m, 2H), 7.9(s, 1H), 8.0(d, 1H) | Example 12 |
| 282 (IV) | 483 (M + H) | 79–80 | (DMSO-D6) δ 1.2–3.6(m, 22H), 3.3(s, 3H), 4.22 and 4.5(m, 2H), 6.67(d, 1H), 6.8(s, 1H), 7.08(d, 1H), 7.75(m, 2H), 7.9(s, 1H), 8.0(d, 1H) | Example 12 |
| 283 (IV) | 559 (M + H) | 113–115 | (DMSO-D6) δ 1–1.48(m, 29H), 3.3(s, 3H), 7.0(m, 1H), 7.18(m, 2H), 7.75(m, 2H), 7.9(s, 1H), 8.0(m, 1H) | Example 12 |
| 284 (IV) | 520 (M + H) | 111–112 | (DMSO-D6) δ 1.6–4.0(m, 19H), 4.6 and 4.9(m, 2H), 7.2(m, 1H), 7.4–7.8(m, 6H), 7.95(s, 1H), 8.02(d, 1H), 9.5(bm, 1H) | As for 18 (IV) above |
| 285 (IV) | 544 (M + H) | 111–112 | (DMSO-D6) 5 1.6–3.2(m, 15H), 3.3(s, 3H), 3.5(m, 1H), 4.5 and 4.6(m, 2H), 6.9(d, 1H), 7.35(d, 1H), 7.5(dd, 1H), 7.75(m, 2H), 7.81(d, 1H), 7.9(s, 1H), 8.0(dd, 1H), 8.68(d, 1H) | Example 12 |
| 286 (IV) | 491 (M + H) | 115–117 | (DMSO-D6) δ 1.6–3.2(m, 16H), 3.3(s, 3H), 3.35–3.6(m, 3H), 4.9(m, 2H), 6.9(m, 1H), 7.0–7.2(m, 2H), 7.75(m, 2H), 7.92(s, 1H), 8.02(m, 1H) | Example 12 |
| 287 (IV) | 443 (M + H) | 142–144 | (DMSO-D6) δ 1.6–3.4(m, 14H), 3.3(s, 3H), 3.4–3.7(m, 2H), 4.6–4.8(m, 2H), 7.0(m, 3H), 7.3(m, 2H), 7.75(m, 2H), 7.92(s, 1H), 8.04(dd, 1H) | Example 12 |
| 288 (IV) | 525 (M + H) | 84–86 | (DMSO-D6) δ 1.6–3.4(m, 22H), 4.2–4.7(m, 2H), 7.38(d, 1H), 7.5( d, 1H), 7.75(m, 2H), 7.95(s, 1H), 8.02(m, 1H) | As for 18 (IV) above |
| 289 (IV) | 491 (M + H) | 149–151 | (DMSO-D6) δ 1.3–2.0(m, 8H), 2.22(s, 3H), 2.3–2.6(m, 4H), 2.8(m, 2H), 3.1(m, 1H), 3.3(s, 3H), 3.5(m, 1H), 4.3–4.6(m, 2H), 6.84(dd, 1H), 7.0(d, 1H), 7.2(m, 1H), 7.75(m, 2H), 7.9(s, 1H), 8.0(dd, 1H) | Example 12 |
| 290 (IV) | 502 (M + H) | 93–95 | (DMSO-D6) δ 1.6–4.0(m, 16H), 3.3(s, 3H), 4.4–5.1(m, 2H), 7.4(t, 1H), 7.8(m, 3H), 7.9–8.1(m, 3H), 9.5–10.0(bm, 1H) | As for 18 (IV) above |
| 293 (IV) | 445 (M + H) | 66–68 | (DMSO-D6) δ 1.6–3.0(m, 7H), 2.8(m, 1H), 3.2(m, 3H), 3.3(s, 3H), 3.4–3.7(m, 4H), 4.62(m, 1H), 5.1–5.4(m, 2H), 7.2(m, 11–1), 7.8(m, 2H), 7.95(m, 1H), 8.02(d, 1H), 8.6(m, 2H), 9.5(bs, 1H) | Example 15 |
| 339 (I) | (M + H) 458 | foam | (DMSO-D6) δ 1.42–1.70(m, 5H), 1.84–1.94(m, 3H), 2.35–2.42(m, 2H), 2.54–2.62(m, 1H), 2.73–2.87(m, 3H), 3.02–3.10(m, 1H), 3.30–3.36(m, 1H), 4.39–4.44(m, 1H), 4.53–4.57(m, 1H), 6.95–6.99(m, 1H), 7.24–7.25(m, 1H), 7.47–7.50(m, 1H), 7.56–7.67(m, 1H), 7.77–7.82(m, 1H), 7.94–7.96(m, 1H) | Example 2 step c |
| (340) (I) | (M + H) 484 | 156–157 | (DMSO-D6) δ 1.40–1.99(m, 8H), 2.35–2.46(m, 2H), 2.54–2.62(m, 1H), 2.73–2.85(m, 3H), 3.02–3.13(m, 1H), 3.60–3.72(m, 1H), 4.39–4.47(m, 1H), 4.51–4.64(m, 1H), 6.96–7.00(m, 1H), 7.25–7.26(m, 1H), 7.50(d, 1H), 7.59–7.63(m, 1H), 7.74–7.78(m, 1H), 8.06–8.09(m, 2H), 8.45–8.48(m, 1H), 8.96–8.98(m, 1H) | Example 2 step c |
| 341 (I) | (M + H) 485 | 127–129 | (DMSO-D6) δ 1.44–1.99(m, 8H), 2.40–2.48(m, 2H), 2.58–2.67(m, 1H), 2.75–2.90(m, 3H), 3.04–3.16(m, 1H), 3.56–3.69(m, 1H), 4.40–4.49(m, 1H), 4.53–4.63(m, 1H), 6.96–7.00(m, 1H), 7.26–7.27(m, 1H), 7.48–7.51(m, 1H), 7.85–7.88(m, 1H), 8.09–8.11(m, 1H), 8.16–8.19(m, 1H), 9.01(s, 2H) | Example 2 step c using Quinoxa- line-6- carboxylic acid (obtained from hydrolysis of the commer- cially available Quinoxa- line-6- carboxylic acid methyl ester) |

TABLE VII-continued

| Compound (Table) | MS | MP (° C.) | ¹HNMR | Can be prepared using: |
|---|---|---|---|---|
| 342 (I) | (M + H) 532 | foam | (DMSO-D6) δ 1.36–1.44(2H, m), 1.55–1.61(2H, m), 1.76–1.82(2H, m), 1.89–1.96(2H, m), 2.34–2.41(3H, m), 2.72–2.80(2H, m), 2.95(2H, t), 3.21(3H, s), 4.15–4.22(2H, m), 4.38–4.46(1H, m), 5.87(2H, s), 6.96–6.99(2H, m), 7.24–7.26(2H, m), 7.49(1H, d), 8.34(1H, s) | Example 2 step c using 3-Amino-4-methanesulfonyl-thiophene-2-carboxylic acid (obtained from hydrolysis of the commercially available 3-Amino-4-methanesulfonyl-thiophene-2-carboxylic acid methyl ester) |
| 63 (IV) | 491 (M + H) | 127–129 | (DMSO-D6) δ 1.42–1.96(8H, m), 2.26(3H, s), 2.32–2.41(2H, m), 2.53–2.59(2H, m), 2.67–3.11(4H, m), 3.24(3H, s), 4.28–4.35(2H, m), 6.77–6.81(1H, m), 6.95(1H, d), 7.26(1H, dd), 7.50(1H, ddd), 7.70(1H, d), 7.76–7.82(1H, m), 7.98(1H, ddd) | Example 2 step c |
| 79 (IV) | 497 (M + H) | 168–169 | (DMSO-D6) δ 1.41–1.49(2H, m), 1.53–1.60(2H, m), 1.80(2H, d), 1.92(2H, dz), 2.27(3H, s), 2.38(2H, t), 2.54–2.62(2H, m), 2.77(2H, t), 2.93–3.12(2H, m), 3.40(3H, s), 4.33(2H, dt), 6.80(1H, dd), 6.95(1H, d), 7.26(1H, d), 7.49(1H, d), 7.77(1H, d) | Example 2 step c |
| 423 (I) | (M + H 499 | 181–183 | (DMSO-D⁶) δ 1.44–1.63(6H, m), 1.91–1.98(3H, m), 2.36–2.39(2H, m), 2.53–2.62(4H, m), 2.76–2.90(2H, m), 3.03–3.11(1H, m), 3.34–3.42(1H, m), 4.40–4.45(1H, m), 4.56–4.64(1H, m), 6.96–6.99(1H, m), 7.24(1H, s), 7.48–7.51(1H, m), 7.61–7.65(1H, m), 8.39–8.47(2H, m), 9.06–9.08(1H, m) | Example 2 step c |
| 578 (I) | (M + H) 473 | 145–147 | (DMSO-D⁶) δ 1.33–1.45(2H, m), 1.53–1.64(2H, m), 1.76–1.94(4H, m), 2.36–2.44(2H, m), 2.55–2.64(1H, m), 2.70–2.80(3H, m), 3.03–3.15(1H, m), 4.35–4.44(1H, m), 4.51–4.61(1H, m), 5.08–5.20(1H, m), 6.93–7.00(2H, m), 7.25–7.34(2H, m), 7.45–7.50(1H, m), 7.57–7.63(1H, m), 8.33(1H, s), 8.50–8.62(1H, m) | Example 2 step c |
| 580 (I) | (M + H), 500 | >200 | (DMSO-D⁶) δ 1.43–1.65(4H, m), 1.85–1.96(3H, m), 2.32–2.41(2H, m), 2.54–2.62(2H, m), 2.73–3.14(4H, m), 3.40–3.47(1H, m), 4.37–4.45(1H, m), 4.53–4.62(1H, m), 6.45(1H, d), 6.93–7.00(1H, m), 7.17–7.26(2H, m), 7.33–7.59(4H, m), 11.99(1H, s) | Example 2 step c |
| 419 (I) | (M + H) 464 | >200 | (DMSO-D⁶) δ 1.25–1.68(5H, m), 1.72–1.81(2H, m), 1.88–1.95(2H, m), 2.22(3H, s), 2.31–2.40(2H, m), 2.60–2.78(3H, m), 2.92–3.00(1H, m), 3.44–3.52(1H, m), 4.36–4.49(2H, m), 5.92–6.11(1H, m), 6.91–7.06(1H, m), 7.25(1H, s), 7.30–7.41(1H, m), 7.44–7.54(1H, m) 11.86(1H, s) | Example 2 step c |
| 550 (I) | (M + H) 484 | 80–85 | (DMSO-D⁶) δ 1.40–1.65(5H, m), 1.83–1.96(3H, m), 2.31–2.43(2H, m), 2.50–2.56(1H, m), 2.69–2.92(4H, m), 3.08–3.17(1H, m), 4.36–4.42(1H, m), 4.65–4.73(1H, m), 6.94–7.00(1H, m), 7.19–7.25(1H, m), 7.45–7.50(1H, m), 7.58–7.71(2H, m), 8.00–8.05(1H, m), 8.39–8.46(1H, m), 8.91–8.96(1H, m) | Example 2 step c |
| 426 (I) | (M + H) 464 | 158–159 | (DMSO-D6) δ 1.36–1.45(2H, m), 1.53–1.61(2H, m), 1.72–1.79(2H, m), 1.88–1.96(2H, m), 2.35–2.43(2H, m), 2.52–2.57(1H, m), 2.72–2.79(2H, m), 2.85–2.94(2H, m), 3.32–3.38(1H, m), 3.49(3H, s), 3.99–4.12(1H, m), 4.34–4.51(1H, m), 6.36(1H, d), 6.90–7.06(1H, m), 7.21–7.29(1H, m), 7.42–7.54(2H, m), 7.91–8.03(1H, m) | Example 2 step c |
| 416 (I) | (M+ H) 448 | 133–135 | (DMSO-D6) δ 1.38–1.45(2H, m), 1.53–1.60(2H, m), 1.66–1.84(2H, m), 1.88–1.95(2H, m), 2.34–2.41(2H, m), 2.51–2.58(1H, m), 2.73–2.78(3H, m), 3.01–3.10(1H, m), 3.29–3.36(3H, m), 3.53–3.63(1H, m), 4.38–4.53(2H, m), 6.94–7.01(1H, m), 7.21–7.28(1H, m), 7.29–7.35(1H, m), 7.47–7.52(1H, m), 7.68–7.75(1H, m), 8.42–8.50(1H, m) | Example 2 step c |
| 575 (I) | (M + H) 645 | 140–142 | | Example 2 step c |
| 534 (M + | | 189–190 | | Example |

TABLE VII-continued

| Compound (Table) | MS | MP (° C.) | ¹HNMR | Can be prepared using: |
|---|---|---|---|---|
| 294 (IV) | (M + H) 543 529 | foam | (CDCl₃) δ 1.32–1.45(1H, m), 1.56–1.71(2H, m), 1.79–2.01(5H, m), 2.46–2.61(3H, m), 2.79–2.87(3H, m), 2.92–3.16(4H, m), 3.36–3.42(1H, m), 4.28–4.33(1H, m), 4.79(1H, t), 6.90(2H, dd), 7.12(1H, dt), 7.49(1H, dd), 7.89(1H, ddd), 8.01(1H, dd) | 2 step c Example 2 step c |
| 67 (IV) | (M + H) 495 | 132–133 | (CDCl₃) δ 1.38–1.65(2H, m), 1.73–2.04(6H, m), 2.40–2.67(3H, m), 2.72–2.89(3H, m), 2.99–3.08(1H, m), 3.23–3.28(3H, m), 3.33–3.53(1H, m), 4.21–4.33(1H, m), 4.61–4.86(1H, m), 6.87–6.92(2H, m), 7.10–7.14(1H, m), 7.31–7.37(1H, m), 7.55–7.70(2H, m), 8.07(1H, td) | Example 2 step c |
| 83 (IV) | (M + H) 501 | foam | (CDCl₃) δ 1.50–1.63(2H, m), 1.85–2.00(6H, m), 2.44–2.51(2H, m), 2.56–2.66(1H, m), 2.80–2.88(2H, m), 3.01(2H, s), 3.20(3H, s), 4.27–4.51(3H, m), 6.91(2H, dd), 7.13(1H, dt), 7.23(1H, d), 7.63(1H, d) | Example 2 step c |
| 295 (IV) | (M + H) 491 | | (CDCl₃) δ 1.75–2.03(10H, m), 2.18–2.19(3H, m), 2.44–2.54(2H, m), 2.77–2.89(3H, m), 3.00–3.09(1H, m), 3.23–3.28(3H, m), 3.36–3.52(1H, m), 4.63–4.85(1H, m), 6.70–6.75(1H, m), 7.05–7.11(2H, m), 7.31–7.37(1H, m), 7.56–7.68(2H, m), 8.05–8.10(1H, m) | Example 2 step c |
| 568 (I) | (M + H) 558 | | (DMSO-D6) δ 1.21–1.95(8H, m), 2.35–2.42(2H, m), 2.57–2.66(1H, m), 2.72–2.77(2H, m), 3.08–3.17(1H, m), 4.08–4.13(1H, m), 4.29(2H, d), 4.40–4.46(3H, m), 6.96–7.00(1H, m), 7.25–7.26(1H, m), 7.48–7.51(1H, m), 7.58–7.62(1H, m), 8.01–8.07(1H, m), 8.40–8.43(1H, m), 8.75–8.78(1H, m) | Example 2 step c |
| 296 (IV) | (M + H) 525 | | (CDCl₃) δ 1.58–1.68(4H, m), 1.85(2H, s), 2.00(2H, s), 2.19(3H, 2.51–2.59(3H, m), 2.80–2.92(3H, m), 2.98–3.16(4H, m), 3.37–3.43(1H, m), 4.33(1H, s), 4.76–4.85(1H, m), 6.72–6.74(1H, m), 7.06–7.12(2H, m), 7.45–7.53(1H, m), 7.88–7.91(1H, m), 8.00–8.02(1H, m) | Example 2 step c |
| 471 (I) | 472 (M + H) | | δ 1.40(m, 2H), 1.57(m, 2H), 1.79(m, 2H), 1.90(m, 2H), 2.40 (m, 2H), 2.58(m, 1H), 2.79(m, 2H), 2.87(m, 2H), 4.30(d, 2H), 4.43(m, 1H), 6.97(dd, 1H), 7.13 (m, 2H), 7.25(d, 1H), 7.43(d, 1H), 7.49(d, 1H), 7.65(m, 2H) | Example 2 step c |
| 475 (I) | 526 (M + H) | | (DMSO-D6) δ 1.67–1.78(m, 2H), 1.95–2.09(m, 3H), 2.18–2.27(m, 2H), 2.44(d 3H), 2.77–2.88(m, 1H), 3.08–3.19(m, 3H), 3.33–3.52(m, 5H), 3.59–3.67(m, 1H), 4.60–4.68(m, 1H), 4.84(s, 1H), 7.05(ddd, 1H), 7.14–7.27(m, 1H), 7.37(dd, 1H), 7.55(t, 1H), 7.61(q, 1H), 7.70–7.71(m, 2H), 7.78–7.80(m, 1H), 7.86–7.89(m, 1H), | Example 2 step c |
| 569 (I) | 512 (M + H) | | (DMSO-D6) δ 1.65–1.80(m, 2H), 1.99–2.09(m, 2H), 2.19–2.30(m, 2H), 2.77–2.90(m, 1H), 3.07–3.21(m, 3H), 3.30–3.37(m, 2H), 3.47–3.57(m, 2H), 3.59–3.71(m, 1H), 4.59–4.69(m, 1H), 4.82–4.86(m, 1H), 7.05(ddd, 1H), 7.37(dd, 1H), 7.49(s, 2H), 7.55(t, 1H), 7.64–7.69(m, 2H), 7.84–7.86(m, 1H), 7.92(td, 1H) | Example 2 step c |
| 477 (I) | 507 (M + H) | | (DMSO-D6) δ 1.64–1.78(m, 2H), 1.99–2.09(m, 3H), 2.17–2.29(m, 3H), 2.70–2.85(m, 1H), 3.04–3.19(m, 3H), 3.28–3.38(m, 3H), 3.31(s, 3H), 3.46–355(m, 2H), 3.66(t, 2H), 4.12(t, 2H), 4.56–4.68(m, 1H), 4.81–4.86(m, 1H), 6.94–6.97(m, 2H), 7.04(dd, 1H), 7.05(ddd, 1H), 7.34–7.39(m, 2H), 7.55(t, 1H), | Example 2 step c |
| 584 (I) | 592 (M + H) | | (CDCl₃) δ 1.45(s, 9H), 1.48–1.67(m, 4H), 1.75–1.85(m, 2H), 2.03(m, 3H), 2.42–2.51(m, 2H), 2.56(m, 1H), 2.71–2.84(m, 3H), 2.91–3.06(m, 1H), 3.54(q, 2H), 3.75–3.88(m, 1H), 4.03(t, 2H), 4.27(septet, 1H), 4.68–4.82(m, 1H), 4.93–5.01(m, 1H), 6.75(dd, 1H), 6.90–7.00(m, 3H), 7.25–7.32(m, 3H) | Example 2 step c |
| 325 (I) | 491 (M + H) | | (DMSO-D6) δ 1.69–1.83(2H, m), 1.98–2.11(3H, m), 2.17–2.28 (3H, m), 2.81–2.92(1H, m), 3.08–3.21(3H, m), 3.47–3.59(2H, m), 3.61–3.71(1H, m), 4.61–4.73(2H, m), 4.82–4.86(1H, m), 7.05(1H, ddd), 7.37(1H, dd), 7.56(1H, t), 7.77(1H, ddd), 8.51(1H, s), 8.80(1H, d) | Example 2 step c using acid prepared according to Journal of Heterocyclic chemistry, 1972, p1149 |
| 585 (I) | 507 (M + | | (DMSO-D6) δ 1.70–1.78(m, 2H), 2.00–2.09(m, 2H), | Example 2 step c, |

TABLE VII-continued

| Compound (Table) | MS | MP (° C.) | ¹HNMR | Can be prepared using: |
|---|---|---|---|---|
| | H) | | 2.18–2.26(m, 2H), 3.05–3.17(m, 2H), 3.24–3.40(m, 2H), 3.97–4.06(m, 2H), 4.44–4.52(m, 2H), 4.59–4.70(m, 2H), 4.73(s, 2H), 4.81–4.86(m, 1H), 4.91–4.93(m, 2H), 6.90–6.93(m, 1H), 6.96–7.04(m, 1H), 7.07–7.11(m, 1H), 7.17–7.20(m, 1H), 7.34–7.43(m, 2H), 7.55(m, 1H), | using 3-tert-butoxycarbonylmethoxybenzoic acid, followed by the addition of (1M) HCl in ether to form final compound as hydrochloride salt. (HCl cleaved tert-butyl ester to leave acid.) |
| 586 (I) | 492 (M + H) | | (DMSO-D6) δ 1.56–1.87(3H, m), 1.94–2.17(5H, m), 3.06–3.27(7H, m), 3.50–3.78(3H, m), 4.19(2H, t), 4.57–4.69(1H, m), 4.80–4.85(1H, m), 6.98–7.10(4H, m), 7.34–7.44(2H, m), 7.57(1H, dd) | Prepared by deprotection of 584 (I) using trifluoroacetic acid in dichloromethane |
| 588 (I) | 551 (M + H) | 145 | (CDCl₃) δ 0.09(2H, dd), 0.44(2H, dd), 0.83–0.89(1H, m), 1.78(2H, m), 1.96–2.09(3H, m), 2.18–2.28(4H, m), 2.78–2.89(1H, m), 3.08–3.20(4H, m), 3.34(2H, s), 3.47–3.65(3H, m), 4.59–4.68(1H, m), 4.84(1H, s), 7.05(1H, ddd), 7.36(1H, dd), 7.55(1H,t), 7.73–7.81(2H, m), 7.90(1H, t), 8.00(1H, d) | Example 2 step c |
| 71 (IV) | 497 (M + H) | | (CDCl₃) δ 1.56(2H, qd), 1.79–1.99(8H, m), 2.19(3H, s), 2.45–2.52(2H, m), 2.60(1H, tt), 2.76–2.83(2H, m), 2.91–3.11(2H, m), (3H, s), 4.28–4.35(1H, m), 6.74(1H, d), 7.05–7.12(3H, m), (1H, d), 7.63(1H, d) | Example 2 step c |
| 245 (IV) | 486 (M + H) | 120–126 | (CDCl₃) δ 1.45–1.61(2H, m), 1.80–2.03(6H, m), 2.19(3H, s), 2.45–2.53(2H, m), 2.54–2.62(1H, m), 2.79–3.09(4H, m), 3.80–3.99(1H, m), 4.28–4.34(1H, m), 4.62–4.81(1H, m), 6.73(1H, d), 7.05–7.12(3H, m), 7.30(1H, dd), 7.47(1H, d) | Example 2 step c using 2-Oxo-2,3-dihydrobenzothiazole-6-carboxylic acid prepared according to Chem. Pharm. Bull. 1988, 36 p2253 |
| 297 (IV) | 526 (M + H) | 115–117 | (CDCl₃) δ 1.42–1.64(2H, m), 1.78–1.87(3H, m), 1.93–2.01(3H, m), 2.19(3H, s), 2.44–2.51(2H, m), 2.57(1H, tt), 2.75–2.88(3H, m), 3.01–3.14(1H, m), 3.64–3.73(1H, m), 4.27–4.33(1H, m), 4.65–4.74(1H, m), 6.73(1H, d), 7.07(1H, dd), 7.11(1H, d), 7.52(1H, dd), 7.58(1H, d), 8.11(1H, d) | Example 2 step c |
| 298 (IV) | 480 (M + H) | 120–126 | (CDCl₃) δ 1.31–1.66(2H, m), 1.70–2.05(6H, m), 2.19(3H, s), 2.38–2.60(3H, m), 2.73–2.83(2H, m), 2.85–3.11(2H, m), 3.71–3.86(1H, m), 4.26–4.34(1H, m), 4.76–4.92(1H, m), 6.73(1H, d), 7.07(1H, dd), 7.11(1H, s), 7.19–7.34(1H, m), 7.57(1H, t), 7.59–7.68(1H, m), 7.73(1H, t), 8.46(1H, d) | Example 2 step c |
| 214 (IV) | 514 (M + H) | 96 | (CDCl₃) δ 1.42–1.62(2H, m), 1.74–2.02(6H, m), 2.19(3H, s), 2.44–2.61(3H, m), 2.75–2.85(3H, m), 2.95–3.11(2H, m), 3.42(21H, s), 3.45(3H, s), 3.78–3.93(1H, m), 4.26–4.36(1H, m), 4.64–4.81(1H, m), 6.74(1H, d), 7.02–7.15(3H, m), 7.27(1H, s), 7.38(1H, d) | Example 2 step c |
| 589 (I) | 540 (M + H) | | (CDCl₃) δ 1.52–1.62(2H, m), 1.68(1H, d), 1.84(1H, d), 1.92(2H, d), 2.35–2.42(2H, m), 2.52–2.55(1H, m), 2.63(6H, s), 2.72–2.83(3H, m), 2.99–3.13(2H, m), 3.46–3.56(2H, m), 4.38–4.45(1H, m), 4.49(1H, d), 6.98(1H, dd), 7.25(1H, d), 7.49(1H, d), 7.73–7.75(2H, m), 7.81–7.83(1H, m), 8.31(1H, s) | Example 2 step c |
| 590 (I) | 556 (M + H) | | (DMSO-D6) δ 1.43–1.62(4H, m), 1.66(1H, d), 1.85(1H, d), 1.89–1.97(2H, m), 2.35–2.44(3H, m), 2.73–2.87(3H, m), 3.11(1H, t), 3.42(3H, s), 3.52(1H, d), 4.39–4.46(1H, m), 4.50(1H, d), 6.98(1H, d), 7.25(1H, d), 7.49(1H, d), 8.36(1H, t), 8.54(1H, t), 8.67(1H, t) | Example 2 step c |
| 591 (I) | 526 (M + H) | | (DMSO-D6) δ 1.29–1.39(2H, m), 1.90(2H, d), 2.11–2.18(1H, m), 2.39(2H, t), 3.13(2H, t), 3.44–3.52(2H, m), 3.65–3.73(2H, m), 3.82–3.91(4H, m), 3.94–4.01(2H, m), 4.47–4.57(1H, m), 6.15 (1H, d), 6.88–6.93(1H, m), 6.95(1H, dd), 7.03(1H, d), 7.31(1H, t), 7.62–7.65(1H, m), 8.32–8.51(2H, m), 8.95(1H, t) | Example 2 step c |
| 593 (I) | 536 (M + H) | | (DMSO-D6) δ 1.42–1.63(4H, m), 1.66(1H, d), 1.84(1H, d), 1.89–1.97(2H, m), 2.32–2.45(1H, m), 2.50–2.61(2H, m), 2.72–2.87(3H, m), 3.08(1H, t), 3.37(3H, s), 3.48(1H, t), 4.37–4.46(1H, m), 4.46–4.55(1H, m), 6.98(1H, dd), 7.25(1H, d), 7.49(1H, d), 8.21(1H, t), 8.30(1H, t), 8.48(1H, t) | Example 2 step c |

TABLE VII-continued

| Compound (Table) | MS | MP (° C.) | ¹HNMR | Can be prepared using: |
|---|---|---|---|---|
| 594 (I) | 550 (M + H) | | (DMSO-D6) δ 1.38–1.52(2H, m), 1.53–1.64(2H, m), 1.84(2H, d), 1.88–1.98(2H, m), 2.37–2.45(4H, m), 2.58–2.68(1H, m), 2.74–2.82(3H, m), 3.17(3H, s), 4.37–4.50(2H, m), 6.99(1H, dd), 7.00–7.02(1H, m), 7.26(1H, d), 7.49(1H, d), 7.61(1H, d), 7.70(1H, dd), 8.23(1H, d) | Example 2 step c |
| 299 (IV) | 525 (M + H) | | (DMSO-D6) δ 1.38–1.5(2H, m), 1.60–1.70(2H, m), 1.81–2.00(2H, m), 2.40(3H, s), 2.41–3.31(9H, m), 3.35(3H, s), 3.41–3.58(1H, m), 4.4–4.55(2H, m), 7.09(1H, d), 7.34(1H, d), 7.71(2H, m), 7.90(1H, s), 8.0(1H, m) | Example 12 |
| 300 (IV) | 489 (M + H) | | (DMSO-D6) δ 1.10(3H, t), 1.35–1.50(2H, m), 1.58–1.70(2H, m), 1.81–1.97(2H, m), 2.25–3.20(11H, m), 3.32(3H, s), 3.4–3.6(1H, m), 4.25–4.6(2H, m), 6.85–7.00(3H, m), 7.63–7.78(2H, m), 7.90(1H, s), 7.98–8.02(1H, m) | Example 12 |
| 143 (IV) | 465 (M + H) | | (CDCl₃) δ 1.63–1.74(2H, m), 1.78–1.88(3H, m), 1.92–2.04(3H, m), 2.19(3H, s), 2.43–2.55(2H, m), 2.64(1H, tt), 2.76–2.94(3H, m), 3.13–3.27(1H, m), 4.25–4.35(2H, m), 4.82–4.90(1H, m), 6.74(1H, d), 7.07(1H, dd), 7.11(1H, d), 7.56(1H, dd), 7.85(1H, d), 8.25(1H, dd), 8.32(1H, d), 9.19(1H, dd) | Example 2 step c |
| 301 (IV) | 530 (M + H) | | (CDCl₃) δ 1.57–1.71(2H, m), 1.80–1.91(3H, m), 1.95–2.06(3H, m), 2.20(3H, s), 2.47–2.55(2H, m), 2.61–2.72(1H, m), 2.79–2.86(2H, m), 2.91–3.35(2H, m), 3.08(3H, s), 4.28–4.37(1H, m), 4.69–4.80(2H, m), 6.74(1H, d), 6.90(1H, d), 7.07(1H, dd), 7.12(1H, d), 7.57(1H, d), 7.79(1H, dd), 8.32(1H, d) | Example 2 step c |
| 572 (I) | 500 (M + H) | | (CDCl₃) δ 1.37–1.66(2H, m), 1.73–1.88(3H, m), 1.93–2.05(3H, m), 2.41–2.51(2H, m), 2.52–2.63(1H, m), 2.75–2.86(2H, m), 2.86–3.09(2H, m), 3.71–3.90(1H, m), 4.23–4.32(1H, m), 4.77–4.93(1H, m), 6.75(1H, dd), 6.99(1H, d), 7.27–7.32(3H, m), 7.54–7.67(1H, m), 7.57(1H, t), 7.74(1H, t), 8.46(1H, d) | Example 2 step c |
| 120 (IV) | 480 (M + H) | | (CDCl₃) δ 1.46–1.66(2H, m), 1.79–2.01(6H, m), 2.19(3H, s), 2.45–2.52(2H, m), 2.59(1H, tt), 2.75–2.84(2H, m), 2.92–3.20(2H, m) 3.74–4.00(1H, m), 4.27–4.35(1H, m), 4.55–4.90(1H, m), 6.49(1H, dd), 6.74(1H, d), 7.07(1H, dd), 7.11(1H, d), 7.76(1H, d), 7.8(1H, dd), 8.03(1H, d), 8.48(1H, d), 8.57(1H, d) | Example 2 step c using acid available from Bionet Research Ltd., Highfield Industrial Estate, Camelford, Cornwall, PL32 9QZ, United Kingdom |
| 145 (IV) | 538 (M + H) | | (CDCl₃) δ 1.35–1.73(2H, m), 1.77–1.89(3H, m), 1.92–2.06(3H, m), 2.19(3H, s), 2.43–2.64(3H, m), 2.74–2.83(2H, m), 2.83–2.94(1H, m), 3.00–3.12(1H, m), 3.38–3.54(1H, m), 4.26–4.35(1H, m), 4.76–4.92(1H, m), 6.73(1H, d), 7.07(1H, dd), 7.11(1H, d), 7.70(1H, d), 7.98(1H, dd), 8.19(1H, d) | Example 2 step c using acid available from Peakdale Inc. 109 East Scotland Drive Bear, DE, 19701-1756 USA |
| 240 (IV) | 465 M + H) | | (CDCl₃) δ 1.62–1.74(2H, m), 1.77–1.86(3H, m), 1.93–2.03(3H, m), 2.33(3H, s), 2.41–2.54(2H, m), 2.65(1H, tt), 2.78–2.86(1H, m), 2.89(2H, td), 3.21(1H, td), 4.21–4.35(2H, m), 4.81–4.90(1H, m), 6.67(1H, dd), 6.78(1H, d), 7.20(1H, d), 7.57(1H, dd), 7.85(1H, d), 8.25(1H, dd), 8.32(1H, d), 9.19(1H, dd) | Example 2 step c |
| 267 (IV) | 453 (M + H) | | (CDCl₃) δ 1.62(2H, qd), 1.79–2.01(6H, m), 2.19(3H, s), 2.4(2H, m), 2.64(1H, tt), 2.74–2.85(2H, m), 3.12–3.22(1H, m), 4.26–4.32(1H, m), 4.77–4.86(1H, m), 5.24–5.33(1H, m), 6.74(1H, d), 6.84(1H, td), 7.07(1H, dd), 7.11(1H, d), 7.21(1H, dd), 7.23(1H, dd), 7.60(1H, dd), 8.06(1H, d), 8.13(1H, dt) | Example 2 step c |
| 199 (IV) | 470 (M + H) | | (CDCl₃) δ 1.57–1.67(2H, m), 1.81–1.88(2H, m), 1.93–2.01(4H, m), 2.20(3H, s), 2.50(2H, td), 2.65(1H, tt), 2.82(2H, td), 2.96–3.20(2H, m), 4.28–4.35(1H, m), 4.74(2H, d), 6.73–6.75(2H, m), 7.12(3H, m), 7.28(1H, d), 7.35(1H, dd), 9.35(1H, s) | Example 2 step c |
| 181 (IV) | 538 (M + H) | | (CDCl₃) δ 1.50–1.65(2H, m), 1.70–1.83(3H, m), 1.93–2.04(3H, m), 2.32(3H, s), 2.40–2.50(2H, m), 2.52–2.62(1H, m), 2.76–2.92(3H, m), 3.01–3.10(1H, m), 3.38–3.52(1H, m), 4.22–4.30(1H, m), 4.77–4.90(1H, m), 6.67(1H, dd), 6.77(1H, d), 7.20(1H, d), 7.70(1H, d), 7.98(1H, dd), 8.19(1H, d) | Example 2 step c |
| 216 (IV) | 526 (M + H) | | (CDCl₃) δ 1.47–1.66(2H, m), 1.79–1.88(3H, m), 1.95–2.04(3H, m), 2.32(3H, s), 2.53–2.61(2H, m), 2.70(1H, tt), 2.76–2.89(3H, m), 2.99–3.13(1H, m), | Example 2 step c |

TABLE VII-continued

| Compound (Table) | MS | MP (° C.) | ¹HNMR | Can be prepared using: |
|---|---|---|---|---|
| 266 (IV) | 480 (M + H) | | 3.63–3.74(1H, m), 4.27–4.33(1H, m), 4.63–4.77(114, m), 6.67(1H, dd), 6.77(1H, d), 7.20(1H, d), 7.50(1H, dd), 7.56(1H, d), 8.09(1H, d) (CDCl₃) δ 1.37–1.67(2H, m), 1.76–1.85(3H, m), 1.93–2.01(3H, m), 2.32(3H, s), 2.41–2.48(2H, m), 2.50–2.60(1H, m), 2.77–2.85(2H, m), 2.86–3.10(2H, m), 3.73–3.85(1H, m), 4.23–4.29(1H, m), 4.77–4.92(1H, m), 6.67(1H, dd), 6.77(1H, d), 7.20(1H, d), 7.21–7.31(1H, m), 7.54–7.68(1H, m), 7.56(2H, t), 7.73(1H, t), 8.46(1H, d) | Example 2 step c |
| 540 (I) | 485 (M + H) | | (CDCl₃) δ 1.69–1.84(4H, m), 1.95–2.02(4H, m), 2.43–2.53(2H, m), 2.65(1H, tt), 2.79–2.93(3H, m), 3.18–3.25(1H, m), 4.23–4.35(2H, m), 4.82–4.90(1H, m), 6.75(1H, dd), 7.00(1H, d), 7.31(1H, d), 7.57(1H, dd), 7.86(1H, d), 8.25(1H, dd), 8.32(1H, d), 9.19(1H, dd) | Example 2 step c |
| 204 (IV) | 470 (M + H) | | (CDCl₃) δ 1.57–1.67(2H, m), 1.77–1.85(2H, m), 1.94–2.02(4H, m), 2.33(3H, s), 2.45–2.52(2H, m), 2.61–2.69(1H, m), 2.81–2.86(2H, m), 2.97–3.18(2H, m), 4.24–4.30(1H, m), 4.74(2H, d), 6.68(1H, dd), 6.73(1H, d), 6.78(1H, d), 7.04(1H, td), 7.20(1H, d), 7.28(1H, d), 7.35(1H, dd), 9.34(1H, s). | Example 2 step c |
| 104 (IV) | 480 (M + H) | | (CDCl₃) δ 1.49–1.63(2H, m), 1.76–2.00(6H, m), 2.33(3H, s), 2.43–2.49(2H, m), 2.59(1H, tt), 2.79–2.85(3H, m), 3.00–3.18(1H, m), 3.81–3.96(1H, m), 4.24–4.29(1H, m), 4.67–4.83(1H, m), 6.49(1H, dd), 6.67(1H, dd), 6.78(1H, d), 7.20(1H, d), 7.76(1H, d), 7.88(1H, dd), 8.03(1H, d) 8.48(1H, d), 8.57(1H, d) | Example 2 step c |
| 243 (IV) | 486 (M + H) | | (DMSO-D6/CDCl₃) δ 1.43–1.59(2H, m), 1.73–1.98(6H, m), 2.32(3H, s), 2.43–2.48(2H, m), 2.79–2.87(2H, m), 2.91–3.40(5H, m), 4.23–4.30(1H, m), 6.68(1H, dd), 6.78(1H, d), 7.14(1H, d), 7.19(1H, d), 7.26(1H, dd), 7.43(1H, d), 7.51(1H, s). | Example 2 step c |
| 191 (IV) | 514 (M + H) | | (CDCl₃) δ 1.46–1.59(2H, m), 1.76–2.00(6H, m), 2.32(3H, s), 2.44–2.48(2H, m), 2.54–2.59(1H, m), 2.78–2.85(3H, m), 3.42(3H, s), 3.45(3H, s), 3.79–3.92(1H, m), 4.23–4.30(1H, m), 4.67–4.79(1H, m), 6.67(1H, dd), 6.77(1H, d), 7.02(1H, d), | Example 2 step c |
| 519 (I) | 490 (M + H) | | 7.15(1H, s), 7.20(1H, d), 7.37(1H, d) (CDCl₃) δ 1.61(2H, qd), 1.77–1.85(2H, m), 1.94–2.02(4H, m), 2.38–2.51(2H, m), 2.65(1H, tt), 2.80–2.85(2H, m), 2.95–3.14(2H, m), 4.25–4.30(1H, m), 4.73–4.77(2H, m), 6.73(1H, d), 6.75(1H, dd), 7.00(1H, d), 7.03(1H, td), 7.27(1H, dd), 7.31(1H, d), 7.35(1H, d 9.49(1H, s) | Example 2 step c |
| 494 (I) | 558 (M + H) | | (CDCl₃) δ 1.48–1.71(2H, m), 1.74–1.83(3H, m), 1.93–2.03(3H, m), 2.42–2.50(2H, m), 2.55–2.62(1H, m), 2.76–2.93(3H, m), 3.01–3.10(1H, m), 3.40–3.50(1H, m), 4.22–4.31(1H, m), 4.77–4.90(1H, m), 6.75(1H, dd), 6.98(1H, d), 7.30(1H, d), 7.67(1H, d), 7.98(1H, dd), 8.19(1H, d) | Example 2 step c |
| 238 (IV) | 511 (M + H) | 172–173 | (CDCl₃) δ 1.53–1.63(2H, m), 1.82–1.89(3H, m), 2.00–2.05(3H, m), 2.05–2.61(3H, m), 2.80–2.84(3H, m), 2.98–3.09(1H, m), 3.03(3H, s), 3.77(1H, br s), 4.41–4.45(1H, m), 4.70(1H, hr s), 6.99(2H, d), 7.21–7.26(1H, m), 7.44–7.54(2H, m), 7.86(2H, d) | Example 21 |
| 496 (I) | 500 (M + H) | | (DMSO-D6) δ 1.46(2H, qd), 1.54–1.61(2H, m), 1.65–1.88(3H, m), 1.89–1.97(2H, m), 2.37–2.42(2H, m), 2.54–2.61(1H, m), 2.73–2.83(2H, m), 3.04–3.17(1H, m), 3.61–3.72(1H, m), 4.39–4.56(2H, m), 6.62(1H, dd), 6.98(1H, dd), 7.25(1H, d), 7.49(1H, d), 7.87(1H, dd), 7.97(1H, dd), 8.04(1H, dd), 8.52(1H, dd), 8.65(1H, dd) | Example 2 step c |
| 483 (I) | 506 (M + H) | | (DMSO-D6) δ 1.41(2H, qd), 1.53–1.62(2H, m), 1.68–1.82(2H, m), 1.89–1.96(2H, m), 2.36–2.43(3H, m), 2.53–2.59(3H, m), 2.74–2.80(3H, m), 4.39–4.45(1H, m), 6.97(1H, dd), 7.13(1H, d), 7.25(1H, d), 7.30(1H, dd), 7.49(1H, d), 7.66(1H, d) | Example 2 step c |
| 302 (IV) | 498 (M + H) | | (CDCl₃) δ 1.40–1.74(2H, m), 1.79–2.02(6H, m), 2.20(3H, s), 2.42–2.61(3H, m), 2.67(1H, td), 2.74–2.84(2H, m), 3.16(1H, t), 3.91–4.00(1H, m), 4.26–4.36(1H, m), 4.58–4.78(5H, m), 6.74(1H, d), 6.76–6.79(1H, m), 6.98–7.02(3H, m), 7.07(1H, dd), 7.12(1H, d) | Example 2 step c |
| 303 (IV) | 498 (M + H) | | (CDCl₃) δ 1.42–1.61(2H, m), 1.77–1.90(3H, m), 1.93–2.03(3H, m), 2.33(3H, | Example 2 step c |

TABLE VII-continued

| Compound (Table) | MS | MP (° C.) | ¹HNMR | Can be prepared using: |
|---|---|---|---|---|
| | | | s), 2.41–2.49(2H, m), 2.57(1H, tt), 2.67(1H, t), 2.77–2.84(2H, m), 3.16(1H, t), 3.95(1H, d), 4.24–4.29(1H, m), 4.59–4.77(5H, m), 6.68(1H, dd), 6.75–6.79(2H, m), 6.97–7.00(3H, m), 7.21(1H, d) | |
| 596 (I) | 518 (M + H) | | (CDCl₃) δ 1.43–1.64(2H, m), 1.77–1.89(3H, m), 1.94–2.01(3H, m), 2.41–2.50(2H, m), 2.57(1H, tt), 2.68(1H, t), 2.76–2.83(2H, m), 3.16(1H, t), 3.94–3.97(1H, m), 4.24–4.30(1H, m), 4.58–4.63(1H, m), 4.68(2H, s), 4.76(2H, d), 6.76–6.78(2H, m), 6.98–7.00(3H, m), 7.26(1H, s), 7.31(1H, d) | Example 2 step c |
| 467 (I) | 534 (M + H) | | (DMSO-D6) δ 1.35–1.50(2H, m), 1.52–1.65(3H, m), 1.68–1.84(2H, m), 1.88–1.98(2H, m), 2.35–2.44(2H, m), 2.54–2.61(1H, m), 2.73–2.82(3H, m), 3.37(3H, s), 3.57(2H, s), 3.60–3.71(1H, m), 4.38–4.56(2H, m), 6.98(1H, dd), 7.07(1H, dd), 7.24(1H, d), 7.26(1H, d), 7.47(1H, d), 7.50(1H, d) | Example 2 step c |
| 269 (IV) | 453 (M + H) | | (CDCl₃) δ 1.55–1.68(4H, m), 1.75–2.01(4H, m), 2.33(3H, s), 2.41–2.51(2H, m), 2.64(1H, tt), 2.78–2.87(3H, m), 3.12–3.24(1H, m), 4.21–4.29(1H, m), 4.76–4.88(1H, m), 5.23–5.34(1H, m), 6.67(1H, dd), 6.78(1H, d), 6.84(1H, t), 7.19–7.26(2H, m), 7.60(1H, d), 8.06(1H, s), 8.13(1H, dd) | Example 2 step c |
| 597 (I) | 546 (M + H) | | (CDCl₃) δ 1.39–1.66(2H, m), 1.73–1.86(4H, m), 1.92–2.03(2H, m), 2.41–2.50(2H, m), 2.53–2.63(1H, m), 2.76–2.88(2H, m), 2.98–3.12(1H, m), 3.62–3.77(1H, m), 4.24–4.29(1H, m), 4.62–4.78(1H, m), 6.75(1H, dd), 6.99(1H, d), 7.31(2H, d), 7.53(1H, dd), 7.57(1H, t), 8.12(1H, d) | Example 2 step c |
| 598 (I) | 474 (M + H) | | (CDCl₃) δ 1.58–1.75(2H, m), 1.80–1.88(2H, m), 1.91–2.05(4H, m), 2.53–2.61(2H, m), 2.71–2.90(4H, m), 3.18–3.22(1H, m), 4.27–4.33(1H, m), 4.84(1H, d), 5.55(1H, d), 6.75(1H, dd), 6.95(1H, dd), 7.00(1H, d), 7.31(1H, d), 8.09(1H, s), 8.46(1H, dd), 8.62(1H, dd) | Example 2 step c |
| 579 (I) | 491 (M + H) | | (CDCl₃) δ 1.61(1H, qd), 1.75–2.02(7H, m), 2.42–2.51(2H, m), 2.59–2.67(1H, m), 2.75–2.86(3H, m), 3.12–3.21(1H, m), 4.23–4.29(1H, m), 4.76–4.85(1H, m), 5.23–5.32(1H, m), 6.75(1H, dd), 6.99(1H, d), 7.16(1H, ddd), 7.30(1H, d), 7.58(1H, dd), 8.07(2H, s) | Example 2 step c |
| 599 (I) | 487 (M + H) | | (CDCl₃) δ 1.58–1.67(1H, m), 1.75–2.02(7H, m), 2.43–2.51(3H, m), 2.59–2.68(1H, m), 2.61(3H, s), 2.76–2.85(3H, m), 3.12–3.23(1H, m), 4.23–4.28(1H, m), 4.78–4.87(1H, m), 5.30–5.38(1H, m), 6.67(1H, d), 6.75(1H, dd), 7.20(1H, dd), 7.30(1H, d), 7.51(1H, d), 8.01(1H, s) | Example 2 step c |
| 600 (I) | 507 (M + H) | | (CDCl₃) δ 1.61(1H, qd), 1.70–2.04(7H, m), 2.41–2.53(2H, m), 2.63(1H, t), 2.73–2.88(3H, m), 3.09–3.23(1H, m), 4.21–4.31(1H, m), 4.74–4.86(1H, m), 5.20–5.30(1H, m), 6.75(1H, dd), 6.99(1H, d), 7.19(1H, d), 7.30(1H, d), 7.55(1H, d), 8.04(1H, s), 8.19(1H, s) | Example 2 step c |
| 304 (IV) | 505 (M + H) | | (CDCl₃) δ 1.57–1.68(2H, m), 1.82–2.01(6H, m), 2.46–2.54(2H, m), 2.46(3H, s), 2.59–2.69(1H, m), 2.73–2.90(3H, m), 3.10–3.23(1H, m), 4.32–4.39(1H, m), 4.76–4.85(1H, m), 5.22–5.32(1H, m), 6.75(1H, d), 7.14–7.27(2H, m), 7.58(1H, dd), 8.07(2H, s) | Example 2 step c |
| 601 (I) | 487 (M + H) | | (CDCl₃) δ 1.55–1.65(1H, m), 1.75–2.01(7H, m), 2.40(3H, s), 2.44–2.50(2H, m), 2.63(1H, qt), 2.73–2.86(3H, m), 3.10–3.22(1H, m), 4.22–4.28(1H, m), 4.75–4.86(1H, m), 5.22–5.34(1H, m), 6.66(1H, dd), 6.75(1H, dd), 6.99(1H, d), 7.30(1H, d), 7.34(1H, s), 7.97(1H, s), 7.99(1H, d) | Example 2 step c |
| 343 (I) | 566 (M + H) | | (CDCl₃) δ 1.39–1.65(1H, m), 1.77–1.89(4H, m), 1.94–2.03(3H, m), 2.43–2.50(2H, m), 2.54–2.62(1H, m), 2.77–2.90(3H, m), 3.03–3.13(1H, m), 3.53(3H, s), 3.65–3.74(1H, m), 4.26–4.31(1H, m), 4.26(2H, s), 4.69–4.79(1H, m), 6.75(1H, dd), 6.99(1H, d), 7.26–7.35(3H, m), 8.00(1H, d) | Example 2 step c |
| 603 (I) | 526 (M + H) | | (CDCl₃) δ 1.49–1.58(2H, m), 1.76–1.84(3H, m), 1.90–2.01(4H, m), 2.44–2.48(2H, m), 2.53–2.59(1H, m), 2.78–2.82(2H, m), 2.78–3.00(5H, m), 3.15–3.19(1H, m), 4.24–4.29(1H, m), 4.96(2H, s), 6.74–6.80(2H, m), 6.99(1H, d), 7.31(1H, d), 7.66–7.70(2H, m) | Example 2 step c |
| 534 (I) | 543 M + H) | | (CDCl₃) δ 1.49(3H, t), 1.57–2.00(6H, m), 2.43–2.52(2H, m), | |

TABLE VII-continued

| Compound (Table) | MS | MP (° C.) | ¹HNMR | Can be prepared using: |
|---|---|---|---|---|
| | | | 2.56–2.62(3H, m), 2.67(3H, s), 2.78–2.84(3H, m), 3.10–3.19(1H, m),3.74(1H, d), 4.25(1H, dquintet), 4.42–4.49(2H, m), 4.76(1H, d), 6.75(1H, dd), 6.99(1H, d), 7.23(1H, d), 7.30(1H, d), 8.09(1H, s), 8.60(1H, d) | |
| 5 (II) | 474 (M + H) | | | Example 2 step c |
| 6 (II) | 468 (M + H) | | (DMSO-D6) δ 1.39–1.45(1H, m), 1.54–1.93(6H, m), 2.32–2.39(2H, m), 2.49–2.53(2H, m), 2.72–3.02(4H, m), 3.29–3.32(2H, m), 4.31–4.34(1H, m), 6.75–6.79(1H, m), 7.08(1H, ddd), 7.30(2H, dt), 7.49–7.56(2H, m), 7.76(1H, t), 8.24(1H, dd) | Example 2 step c |
| 7 (II) | 453 (M + H) | | (DMSO-D6) δ 1.45–1.69(5H, m), 1.84–1.99(3H, m), 2.40(2H, t), 2.59–2.66(1H, m), 2.73–2.92(3H, m), 3.03–3.14(1H, m), 3.69–3.76(1H, m), 4.31–4.37(1H, m), 4.55–4.61(1H, m), 6.78(1H, dd), 7.09(1H, ddd), 7.31(1H, dt), 7.69–7.78(2H, m), 8.49–8.65(2H, m), 9.15(1H, dd) | Example 2 step c |
| 8 (II) | 441 (M + H) | | (DMSO-D6) δ 1.34–1.45(2H, m), 1.52–1.61(2H, m), 1.76–1.86(2H, m), 1.87–1.96(2H, m), 2.33–2.44(2H, m), 2.56–2.63(1H, m), 2.72–2.81(3H, m), 3.05–3.14(1H, m), 4.29–4.38(1H, m), 4.51–4.61(1H, m), 5.09–5.19(1H, m), 6.73–6.79(1H, m), 6.94–6.99(1H, m), 7.04–7.12(1H, m), 7.28–7.34(2H, m), 7.61(1H, dd), 8.30(1H, s), 8.56(1H, dt) | Example 2 step c |
| 305 (IV) | 514 (M + H) | | (DMSO-D6) δ0 1.42–1.51(2H, m), 1.60–1.93(6H, m), 2.41–2.47(2H, m), 2.41(3H, s), 2.54–2.60(1H, m), 2.72–2.80(2H, m), 3.05–3.15(1H, m), 3.29–3.35(1H, m), 3.60–3.71(1H, m), 4.44–4.54(2H, m), 6.59–6.64(1H, m), 7.07–7.13(1H, m), 7.31–7.38(1H, m), 7.89(1H, m), 7.95–7.99(1H, m), 8.01–8.07(1H, m), 8.50–8.54(III, m), 8.63–8.67(1H, m) | Example 2 step c |
| 306 (IV) | 531 (M + H) | | (DMSO-D6) δ 1.39–1.95(8H, m), 2.40(3H, s), 2.42–2.47(2H, m), 2.55–2.63(2H, m), 2.72–2.81(2H, m), 2.94–3.09(2H, m), 3.42(3H, s), 4.14–4.32(1H, m), 4.46–4.54(1H, m), 7.10(1H, d), 7.36(1H, d), 7.49(1H, d), 7.78(1H, d) | Example 2 step c |
| 307 | 525 | | (DMSO-D6) δ 1.39–1.95(9H, m), 2.42(3H, s), 2.44–2.48(1H, m), 2.55–2.61(1H, m), 2.70–2.83(2H, m), 2.99–3.10(1H, m), 3.29(3H, s), 3.41–3.52(2H, m), 4.46–4.58(2H, m), 7.11(1H, d), 7.36(1H, d), 7.66(2H, dd), 7.99(2H, dd) | Example 2 step c |
| 308 (IV) | 512 (M + H) | | (DMSO-D6) δ 1.60–4.25(18H, m), 4.55–4.80(1H, m), 5.22–5.45(1H, m), 7.05(1H, t), 7.75–7.82(2H, m), 7.85(1H, s), 8.00–8.18(2H, m), 8.60(1H, s), 9.63(1H, br s) | Prepared in a similar manner to Example 15 and isolated as the trifluoroacetate salt |
| 1 (V) | 509 (M + H) | 87–88 | (DMSO-D6) δ 1.11–1.18(2H, m), 1.36–1.53(4H, m), 1.63–1.78(2H, m), 2.07(2H, t), 2.48–2.52(2H, m), 2.81–2.84(4H, m), 3.01–3.04(2H, m), 3.27–3.27(3H, m), 3.49–3.50(1H, m), 4.44–4.53(1H, m), 7.15–7.18(1H, m), 7.44–7.45(1H, m), 7.50–7.53(1H, m), 7.69–7.76(2H, m), 7.90(1H, t), 7.98–8.02(1H, m) | Example 2 step c |
| 2 (V) | 510 (M + H) | | (CDCl₃) δ 1.38–1.48(3H, m), 1.59(1H, brs), 1.81–2.07(4H, m), 2.34(2H, t), 2.55–2.60(1H, m), 2.84–2.92(3H, m), 3.07(4H, s), 3.21(1H, hr s), 3.60(1H, d), 3.68(1H, br s), 4.74(1H, br s), 6.41(1H, dd), 6.64(1H, d), 7.16(1H, d), 7.62–7.70(2H, m), 7.97–8.02(2H, m) | Example 12 |
| 3 (V) | 523 (M + H) | | (DMSO-D6) δ 1.42–1.56(4H, m), 1.64–1.86(4H, m), 2.33(2H, t), 2.54–2.61(1H, m), 2.76–2.85(1H, m), 2.87–2.93(2H, m), 3.04–3.12(1H, m), 3.28(3H, s), 3.36–3.44(1H, m), 3.48–3.57(1H, m), 4.47–4.55(1H, m), 7.70–7.77(2H, m), 7.80(1H, d), 7.91–7.95(2H, m), 8.00(1H, dt), 8.14–8.16(1H, m) | Prepared in a similar maner to Example 12 using (3,4-Dichlorophenyl)-piperidin-4-yl-methanone hydrochloride free base was made insitu using triethylamine |
| 310 (IV) | 478 (M + H) | 169–170 | (DMSO-D6) δ 1.29–1.40(2H, m), 1.53–1.62(2H, m), 1.71–1.77(2H, m), 1.89–1.96(2H, m), 2.35–2.42(2H, m), 2.45–2.49(1H, m), 2.68–2.79(4H, m), 3.70(3H, s), 4.10–4.17(2H, m), 4.38–4.45(1H, m), 6.78–6.82(2H, m), 6.98(1H, dd), 7.25(1H, d), 7.30–7.34(2H, | Example 26 using 4-Methoxyphenylisocyanate |

TABLE VII-continued

| Compound (Table) | MS | MP (° C.) | ¹HNMR | Can be prepared using: |
|---|---|---|---|---|
| 311 (IV) | 466 (M+ | 217 | (DMSO-D6) δ 1.29–1.40(2H, m), 1.53–1.62(2H, m), 1.72–1.78(2H, m), 1.89–1.96(2H, m), 2.36–2.42(2H, m), 2.44–2.49(1H, m), 2.71–2.79(4H, m), 4.11–4.17(2H, m), 4.38–4.45(1H, m), 6.98(1H, dd), 7.05(2H, t), 7.25(1H, d), 7.45(2H, tt), 7.49(1H, d), 8.50(1H, s), 7.49(1H, d), 8.30(1H, s) | Example 26 using 4-Fluoro-phenyl-isocyanate |
| 312 (IV) | 494 (M+H) | 170–172 | (DMSO-D6) δ 1.29–1.40(2H, m), 1.52–1.62(2H, m), 1.72–1.78(2H, m), 1.89–1.96(2H, m), 2.36–2.42(2H, m), 2.43(3H, s), 2.44–2.48(1H, m), 2.71–2.79(4H, m), 4.15(2H, d), 4.38–4.45(1H, m), 6.81(1H, d), 6.98(1H, dd), 7.15(1H, t), 7.24–7.27(2H, m), 7.43(1H, t), 7.49(1H, d), 8.48(1H, s) | Example 26 using 3-(Methylthio)-phenyl-isocyanate |
| 313 (IV) | 462 (M+H) | 178–179 | (DMSO-D6) δ 1.22–1.34(2H, m), 1.52–1.61(2H, m), 1.65–1.72(2H, m), 1.88–1.95(2H, m), 2.33–2.46(3H, m), 2.61–2.76(4H, m), 3.99–4.05(2H, m), 4.22(2H, d), 4.37–4.44(1H, m), 6.97(1H, dd), 7.04(1H, t), 7.18–7:31(6H, m), 7.49(1H, d) | Example 26 using Benzyl-isocyanate |
| 314 (IV) | 492 (M+H) | 166–167 | (DMSO-D6) δ 1.21–1.32(2H, m), 1.51–1.61(2H, m), 1.64–1.71(2H, m), 1.88–1.95(2H, m), 2.32–2.46(3H, m), 2.59–2.67(2H, m), 2.69–2.76(2H, m), 3.71(3H, s), 4.01(2H, d), 4.14(2H, d), 4.37–4.44(1H, m), 6.83–6.87(2H, m), 6.94–6.99(2H, m), 7.14–7.18(2H, m), 7.25(1H, d), 7.49(1H, d) | Example 26 using 4-Methoxybenzyl-isocyanate |
| 315 (IV) | 480 (M+H) | 209–210 | (DMSO-D6) δ 1.21–1.32(2H, m), 1.52–1.61(2H, m), 1.65–1.71(2H, m), 1.88–1.95(2H, m), 2.32–2.46(3H, m), 2.60–2.68(2H, m), 2.70–2.76(2H, m), 4.01(2H, d), 4.19(2H, d), 4.38–4.44(1H, m), 6.97(1H, dd), 7.05(1H, t), 7.11(2H, t), 7.24–7.29(3H, m), 7.49(1H, d) | Example 26 using 4-Fluorobenzyl-isocyanate |

MS = Mass Spectrum has been obtained using either APCI+ or ES+ or ES−

The preparations of certain intermediates are now presented.

Method A
1-(3-Methoxy-4-nitro-benzoyl)-piperidin-4-one

CDI (9 g) added to a solution of 3-methoxy-4-nitrobenzoic acid (10 g) stirring in THF (200 ml) at RT. After 1 hour, 4-piperidone hydrochloride (6.9 g) and triethylamine (7.8 ml) were added and the mixture stirred overnight. The mixture was diluted with ethyl acetate, washed with 2N HCl (100 ml) then saturated NaHCO₃ solution (200 ml) then saturated brine (200 ml). The organic layer was dried (MgSO₄) and evaporated to leave a residue which was purified by column chromatography (silica, mixtures of MeOH in dichloromethane) to give the product as a yellow solid (8.5 g; MS: APCI⁺(M+H) 279).

Method B
1-(3-Methanesulfonyl-benzoyl)-piperidin-4-one

PyBrOP™ (17.3 g) was added to a stirred mixture of 3-methanesulphonyl benzoic acid (7.35 g), 4-piperidone hydrochloride (5 g) and Hunig's base (25 ml) in dichloromethane (250 ml) with stirring at RT. The mixture was stirred overnight then washed with saturated NaHCO₃ solution (200 ml) and then with saturated brine (200 ml). The organic layer was evaporated and the resulting residue purified by column chromatography (silica, 1:1 ethyl acetate: dichloromethane) to give the product as a thick oil (9.6 g; MS: APCI⁺(M+H) 282).

Method C
1-(Benzo[1,2,3]thiadiazole-5-carbonyl)-piperidin-4-one

CDI (4.5 g) added to a solution of the benzo[1,2,3]thiadiazole-5-carboxylic acid (5 g) stirring in THF (100 ml) at RT. After 1 hour 4-piperidone hydrochloride (3.7 g) and triethylamine (4.3 ml) were added and the mixture stirred overnight. The resulting mixture was diluted with ethyl acetate, washed with 2M HCl (100 ml), saturated NaHCO₃ solution (200 ml) and then with saturated brine (200 ml). The organic layer was dried (MgSO₄) and evaporated to leave a residue which was purified by column chromatography (silica, eluting with mixtures of ethyl acetate in dichloromethane) to give the product as a yellow oil (2.1 g; MS: APCI⁺(M+H)262).

Method D
[1,4']Bipiperidinyl-4-ol

4-Oxo-piperidine-1-carboxylic acid tert-butyl ester (20 g) and 4-hydroxypiperidine (6.7 g) were stirred together in dichloroethane (200 ml) with acetic acid (4 ml) at RT for 30 minutes. Sodium triacetoxyborohydride (23 g) was then added and the mixture stirred at RT overnight. The mixture was evaporated to dryness and the residue taken into water, extracted with diethyl ether (3×200 ml), the aqueous was basified to pH 9–10 and extracted with dichloromethane (3×200 ml). The dichloromethane extracts were combined, dried (MgSO₄) and evaporated to leave an oil (19 g; same compound as Example 9 step 1). The oil was dissolved in methanol (300 ml) and treated with concentrated hydrochloric acid (5 ml). The mixture was stirred overnight and then evaporated to dryness to leave the title compound as the hydrochloride salt (15 g).

¹H NMR (400 MHz, DMSO-D6) δ 1.6–2.4 (m, 9H), 2.8–3.5 (m, 8H), 3.62 (m, 1H), 3.95 (s, 1H), 9.29 and 9.059 (bs, 2H), 10.9 and 11.09 (bs, 1H).

Method E
(4-Hydroxy-[1,4']bipiperidinyl-1'-yl)-(3-methanesulfonyl-phenyl)-methanone PyBrOP™ (25.3 g) was added to a stirred solution of 3-methanesulphonyl benzoic acid (10 g), [1,4']bipiperidinyl-4-ol dihydrochloride (13 g, see Method D) and Hunig's base (34 ml) in dichloromethane (500 ml). The resulting mixture was stirred at RT overnight, then washed with saturated NaHCO₃ solution (300 ml) followed by saturated brine (300 ml). The organic layer was dried (MgSO₄) and evaporated to leave an oily residue. Column chromatography (silica, 20% methanol in DCM) gave the product as a white solid (16 g; MS: APCI⁺(M+H) 367).

Method F
4-(3-Chloro-4-fluoro-phenoxy)-piperidine

DEAD (0.43 ml) was added to a solution of triphenylphosphine (0.72 g), 3-chloro-4-fluorophenol (0.403 g) and 4-hydroxy-piperidine-1-carboxylic acid tert-butyl ester (0.5 g) in THF at RT. The resulting mixture was stirred overnight, HCl in dioxan (2 ml of 4M) was added and the mixture stirred at RT overnight. The mixture was then evaporated to dryness and triethylamine (5 ml) was added. The mixture was evaporated and the residue was dissolved in methanol (10 ml), placed onto a SCX cartridge (Varian, 10 g, SCX cartridge available from International Sorbent Technology Isolute® Flash SCX-2) and eluted: first with methanol then with 10% $NH_3$ in methanol. The basic fractions were combined and evaporated to give the product as an oil (0.6 g).

$^1$H NMR (299.946 MHz, DMSO-D6) δ 1.34–1.46 (2H, m), 1.83–1.91 (2H, m), 2.53–2.59 (2H, m), 2.87–2.96 (2H, m), 3.22–3.39 (1H, m), 4.39 (1H, septet), 6.92–6.98 (1H, m), 7.17–7.20 (1H, m), 7.30 (1H, t).

The following intermediates were prepared in similar manner to Method F:

| | MS: (M + H) |
|---|---|
| 4-(4-chloro-2-methyl-phenoxy)-piperidine | 226 |
| 4-(4-chloro-3-fluoro-phenoxy)-piperidine | 230 |
| 4-(4-chloro-2-methoxy-phenoxy)-piperidine | 242 |
| 4-(4-fluoro-2-methoxy-phenoxy)-piperidine | 226 |
| 4-(4-methoxy-phenoxy)-piperidine | 208 |
| 4-p-tolyloxy-piperidine | 192 |
| 4-(4-chloro-3-methyl-phenoxy)-piperidine | 226 |
| 4-(4-chloro-phenoxy)-piperidine | 212 |
| 4-(4-fluoro-phenoxy)-piperidine | 196 |
| 4-(2,4-dichloro-phenoxy)-piperidine | 246 |
| 4-(2-chloro-4-fluoro-phenoxy)-piperidine | 230 |
| 4-(2,4-difluoro-phenoxy)-piperidine | 214 |
| 4-(4-chloro-2-fluoro-phenoxy)-piperidine | 230 |
| 4-(4-fluoro-2-methyl-phenoxy)-piperidine | 210 |
| 4-(4-chloro-2,6-dimethyl-phenoxy)-piperidine | 240 |
| 4-(2,3-dichloro-phenoxy)-piperidine | 246 |
| 4-(2,5-dichloro-phenoxy)-piperidine | 246 |
| 4-(2-chloro-4-methyl-phenoxy)-piperidine | 226 |
| 4-(2-chloro-5-methyl-phenoxy)-piperidine | 226 |
| 1-[3-methyl-4-(piperidin-4-yloxy)-phenyl]-ethanone | 234 |
| 4-(2-chloro-6-methyl-phenoxy)-piperidine | 226 |
| 4-[2-(piperidin-4-yloxy)-phenyl]-morpholine | 263 |
| 4-(4-chloro-2-ethyl-phenoxy)-piperidine | 240 |
| 7-(piperidin-4-yloxy)-quinoline | 229 |
| 4-(2-tert-butyl-phenoxy)-piperidine | 234 |
| 4-(indan-5-yloxy)-piperidine | 218 |
| 4-(4-chloro-2-cyclohexyl-phenoxy)-piperidine | 294 |
| 5-chloro-2-(piperidin-4-yloxy)-benzamide | 255 |
| 4-(4-chloro-2-isoxazol-5-yl-phenoxy)-piperidine | 279 |
| 4-(5-chloro-2-methyl-phenoxy)-piperidine | 226 |
| 4-phenoxy-piperidine | 178 |
| 4-(2,4-dichloro-6-methyl-phenoxy)-piperidine | 260 |
| 4-(3-chloro-4-methyl-phenoxy)-piperidine | 226 |
| 5-chloro-2-(piperidin-4-yloxy)-benzonitrile | 237 |
| 4-(2,4-dichloro-3-methyl-phenoxy)-piperidine | 260 |
| 4-(2-ethyl-4-fluoro-phenoxy)-piperidine | 224 |
| 4-(4-methanesulfonyl-phenoxy)-piperidine | 297 |

Method G
4-Amino-3-ethoxy-benzoic acid

Potassium hydroxide (0.278 g) was added to a solution of 3-fluoro-4-nitrobenzoic acid (0.4 g) in ethanol (7 ml) and the reaction treated with microwaves (300W, 100° C.) for 5 minutes. The reaction mixture was acidified using 2N HCl and extracted with ethyl acetate. The extracts were combined, washed with water, dried ($MgSO_4$) and evaporated to give 3-ethoxy-4-nitro-benzoic acid (0.325 g).

3-Ethoxy-4-nitrobenzoic acid (0.31 g) was treated with 5% palladium on charcoal under an atmosphere of hydrogen (1 bar) for 3 hours. The reaction mixture was filtered and the filtrate was evaporated to leave the product as a beige solid (0.245 g; MS: ES$^-$ (M-H) 180).

Method H
3,4-bis-Methanesulfonyl-benzoic acid

To 3-fluoro-4-nitro-benzoic acid tert-butyl ester (0.5 g) in DMSO was added $NaSO_2Me$. The reaction mixture was heated to 100° C. for 24 hours. A mixture of water, diethyl ether and ethyl acetate (1:1:1) was added and the resulting mixture was extracted with diethyl ether/ethyl acetate (1:1). The organic extracts were combined, dried with $MgSO_4$ and concentrated to leave a residue which was purified by chromatography (using 80% ethyl acetate/20% hexane) to give 3,4-bis-methanesulfonyl-benzoic acid tert-butyl ester (366 mg). $^1$H NMR (399.98 MHz, DMSO-D6) 1.59 (9H, s), 3.50 (3H, s) 3.52 (3H, s), 8.37–8.65 (3H, m).

To 3,4-bis-methanesulfonyl-benzoic acid tert-butyl ester (0.366 g) in dichloromethane was added trifluoroacetic acid and the reaction mixture was stirred for 3 hours. The mixture was evaporated and trituration of the residue with diethyl ether gave the title compound (0.29 g; MS: APCI$^+$(M+H) 279).

Method I
4-Carbamoyl-5-methanesulfonyl-thiophene-2-carboxylic acid

To 4-cyano-5-methanesulfonyl-thiophene-2-carboxylic acid methyl ester (0.5 g) in THF/$H_2O$ (3:1; 16 ml) was added LiOH (0.102 g). Hydrochloric acid (2M) was added and the resulting mixture was extracted with ethyl acetate. The extracts were combined and the solvent evaporated to leave a mixture of 4-cyano-5-methanesulfonyl-thiophene-2-carboxylic acid and the title compound. This mixture was used without further purification. $^1$H NMR (299.944 MHz, DMSO-D6) δ 3.62 (3H, s), 7.99 (1H, s).

Method J
3-(2-Methyl-propane-1-sulfonyl)-benzoic acid

To a suspension of 3-sulfo-benzoic acid (1 g) and potassium carbonate (1.2 g) in dimethylacetamide (10 ml) was added iso-butyl iodide (0.65 ml). The mixture was heated by microwaves (600W) at 150° C. for 15 minutes. The reaction mixture was partitioned between water (100 ml) and ethyl acetate (100 ml), the aqueous layer was separated, acidified to pH 1 with HCl (2N) and extracted with ethyl acetate (100 ml). The extract was evaporated to leave a residue which was purified by flash chromatography (Biotage 12S eluting with ethyl acetate:hexane:acetic acid, 29:70:1) to give the title product as a white solid (0.34 g).

$^1$H NMR: (399.98 MHz, DMSO-D6) δ 0.98 (6H, d), 2.03 (1H, septet), 3.29 (2H, d), 7.81 (1H, t), 8.16 (1H, ddd), 8.27 (1H, dt), 8.38 (1H, t).

3-Cyclopropylmethanesulfonyl-benzoic acid was prepared in a similar manner to that described in Method J. MS: (M-H) 239; $^1$H NMR: (DMSO-d6) δ 0.06–0.10 (2H, m), 0.40–0.45 (2H, m), 0.82–0.89 (1H, m), 3.34 (2H, d), 7.80 (1H, t), 8.14 (1H, d), 8.28 (1H, d), 8.39 (1H, s).

Method K
3-(2-Methoxy-ethoxy)-benzoic acid methyl ester

To a solution of methyl 3-hydroxybenzoate (5.7 g) and 2-bromoethylmethyl ether (5.2 g) in dimethylformamide (100 ml) was added caesium carbonate (24.3 g). The reaction mixture was stirred for 12 hours. The mixture was then patitioned between ethyl acetate (400 ml) and water (400 ml). The organic layer was separated, dried (MgSO$_4$) and the solvent removed under reduced pressure. The residue was purified by flash chromatography (Biotage 12M, eluting iso-hexane then MeOH:dichloromethane 2:98) to give the product as a colourless oil (5.3 g).

$^1$H NMR: (CDCl$_3$) δ 3.44 (3H, s), 3.75 (2H, t), 3.89 (3H, s), 4.15 (2H, t), 7.13 (1H, ddd), 7.32 (1H, t), 7.57 (1H, dd), 7.62 (1H, dt).

3-tert-Butoxycarbonylmethoxy-benzoic acid methyl ester can be prepared in a similar manner to that described in Method K: $^1$H NMR: (299.944 MHz CDCl$_3$) 1.49 (9H, s), 3.91 (3H, s), 4.56 (2H, s), 7.13–7.68 (4H, m).

Method L
3-(2-Methoxy-ethoxy)-benzoic acid
To a suspension of 3-(2-methoxy-ethoxy)-benzoic acid methyl ester (5.3 g) in tetrahydrofuran (200 ml) was added lithium hydroxide monohydrate (5.3 g) followed by water until an homogeneous solution was obtained. The reaction mixture was stirred for 12 hours, acidified and partitioned between ethyl acetate (200 ml) and water (200 ml). The organic layer was separated, dried (MgSO$_4$) and the solvent removed under reduced pressure to yield a colourless solid (3.6 g).

$^1$H NMR: (DMSO-D6) δ 3.31 (3H, s), 3.67 (2H, t), 4.14 (2H, t), 7.20 (1H, ddd), 7.41 (1H, t), 7.44 (1H, dd), 7.53 (1H, dt)

3-(2-tert-Butoxycarbonylamino-ethoxy)-benzoic acid can be prepared in a similar manner to that described in Method L.

3-tert-Butoxycarbonylmethoxy-benzoic acid can be prepared in a similar manner to that described in Method L: $^1$H NMR (299.944 MHz, DMSO-D6) δ 2.51 (9H, s), 4.74 (2H, s), 7.18 (1H, dq), 7.38 (1H, m), 7.41 (1H, m), 7.55 (1H, dt), 13.03 (1H, s).

Method M
4-(2-Carboxy-2-phenyl-ethyl)-piperazine-1-carboxylic acid tert-butyl ester
Piperazine-1-carboxylic acid tert-butyl ester (17.43 g) and 2-phenylacrylic acid (18 g) in iso-propanol (500 ml) was heated at reflux for four days. The resulting precipitate was filtered, washed with diethyl ether and dried under vacuum to give the title compound as a white solid (17 g; MS: APCI$^+$(M+H) 335).

Method N
5-Methanesulfonyl-1H-indole-2-carboxylic acid
To a solution of the 5-methanesulfonyl-1H-indole-2-carboxylic acid methyl ester (0.49 g) in THF (12 mL) and water (4 ml) was added LiOH (0.098 g). The reaction mixture was left to stir for 2 hours. Acetic acid was added and the product extracted with dichloromethane. The organic extracts were combined, dried with magnesium sulfate, filtered and the filtrate evaporated to give the title compound as a solid (0.110 g).

$^1$H NMR (299.946 MHz, DMSO-D6) δ 3.18 (3H, s), 7.32–7.33 (1H, m), 7.61–7.64 (1H, m), 7.73–7.77 (1H, m), 8.30–8.31 (1H, m).

Method O
5-Methyl-imidazo[1,2-a]pyridine-2-carboxylic acid was prepared in a similar manner to 6-fluoro-imidazo[1,2-a]pyridine-2-carboxylic acid (see Example 25) using the commercially available 5-methyl-1,8a-dihydro-imidazo[1,2-a]pyridine-2-carboxylic acid ethyl ester. 6-Methyl-imidazo[1,2-a]pyridine-2-carboxylic acid and 6-methyl-imidazo[1,2-a]pyridine-2-carboxylic acid ethyl ester were prepared in a similar manner to 6-fluoro-imidazo[1,2-a]pyridine-2-carboxylic acid and its ester above.

Method P
Preparation of 4-Methyl-1,1,3-trioxo-1,2,3,4-tetrahydro-1l$^6$-benzo[1,4]thiazine-6-carboxylic acid
Step 1: 4-Methyl-1,1,3-trioxo-1,2,3,4-tetrahydro-1l$^6$-benzo[1,4]thiazine-6-carboxylic acid methyl ester

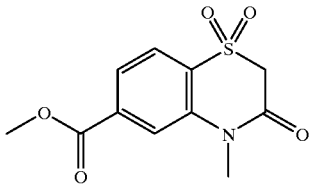

To a solution of 4-methyl-3-oxo-3,4-dihydro-2H-benzo[1,4]thiazine-6-carboxylic acid methyl ester (1 g) in dichloromethane (25 ml) was added 32% peracetic acid dropwise over 10 minutes. The reaction mixture was stirred at room temperature for 48 hours and then diluted with dichloromethane. The organic phase was washed once with water, twice with aqueous sodium sulfite solution, and once with saturated aqueous sodium bicarbonate. The organic phase was dried over magnesium sulfate, filtered, and the solvent evaporated to give the sub-title compound as a solid (1.012 g).

$^1$H NMR (399.978 MHz, CDCl$_3$) δ 3.58 (3H, s), 4.00 (3H, s), 4.27 (2H, s), 7.96–7.99 (2H, m), 8.04–8.06 (1H, m).
Step 2: 4-Methyl-1,1,3-trioxo-1,2,3,4-tetrahydro-1l$^6$-benzo[1,4]thiazine-6-carboxylic acid
To a solution of 4-methyl-1,1,3-trioxo-1,2,3,4-tetrahydro-1l6-benzo[1,4]thiazine-6-carboxylic acid methyl ester (1 g, from step 1) in MeOH (7 ml) was added dropwise a solution of sodium hydroxide (0.6 g) in water (5 ml). The reaction mixture was stirred at room temperature for 1 hour, diluted with water, cooled in an ice/water bath. Slow acidification with HCl (1N) to pH 2 yielded a precipitate which was isolated by filtration to give the title compound (0.595 g) as a solid.

$^1$H NMR (399.978 MHz, DMSO-D6) δ 3.49 (3H,s), 4.91 (2H,s), 7.90–8.03 (3H,m).

Method Q
Preparation of 4-(4-methanesulfonyl-phenoxy)-[1,4']bipiperidinyl
Step a: 4-(4-methanesulfonyl-phenoxy)-[1,4']bipiperidinyl-1'-carboxylic acid tert-butyl ester
To a solution of 4-(4-methanesulfonyl-phenoxy)-piperidine (0.7 g) dissolved in THF (5 ml) and 1,2-dichloroethane (10 ml) with 1-Boc-4-piperidone (0.71 g) was added NaBH(OAc)$_3$ (0.926 g) and acetic acid (0.18 g). After 16 hours at RT aqueous NaOH (1M) solution and dichloromethane were added and the mixture was extracted with dichloromethane. The combined organic extracts were washed with water, dried with magnesium sulfate and concentrated to leave a residue which was purified by chromatography (dichloromethane:methanol 90:10) to give the sub-title product (1.1 g; MS: APCI$^+$(M+H) 439).
Step b: 4-(4-methanesulfonyl-phenoxy)-[1,4']bipiperidinyl
The product of step a was dissolved in dichloromethane (20 ml) and trifluoroacetic acid (5 ml) was added. After 16 hours at room temperature the solution was evaporated to leave the title compound as a TFA salt. The free base (0.7 g; oil; MS: APCI$^+$(M+H) 339) was liberated by addition of aqueous NaOH (1M) and extraction with dichloromethane followed by evaporation of the solvent.

3-Methanesulfonyl-5-nitro-benzoic acid and 3-cyano-5-methanesulfonyl-benzoic acid can be prepared according to a method described in EP-A1-556674.

2-amino-5-MeSO$_2$-benzoic acid can be prepared according to a method described in J. Org. Chem. (1953) 18 1380.

3-Ethanesulfonyl-benzoic acid can be prepared according to a method described in J. Chem. Soc. 1946, 763.

3-Methylsulfamoyl-benzoic acid and 3-dimethylsulfamoyl-benzoic acid can be prepared according to a method described in DE2133038. 3-Methylsulfamoyl-benzoic acid $^1$H NMR: (399.98 MHz, DMSO-D6) δ 7.42 (3H, d), 7.63 (1H, q), 7.76 (1H, t), 8.01 (1H, m), 8.18 (1H, dt), 8.31 (1H, t), 13.48 (1H, s).

Other intermediates can be prepared by literature methods, by adaptation of literature methods or are available commercially. For example:

(2-methyl-4-nitro-2H-pyrazol-3-yl)methanecarboxylic acid, 2-{1-[sulfonyl chloride]-ethyl}-isoindole-1,3-dione and (1,3-dimethyl-3,7-dihydro-purine-2,6-dion-8-yl)methanecarboxylic acid are available from Salor (Aldrich Chemical Company Inc 1001 West Saint Paul Avenue Milwaukee, Wis. 53233 USA);

[4-amino-5-(iso-propyl-sulfonyl)-thiophen-3-yl] carboxylic acid, [3-methyl-5-(4-methyl-[1,2,3] thiadiazol-5-yl)-isoxazol-4-yl]carboxylic acid, 3-cyano-4-(pyrrol-1-yl)-thiophen-5-yl)carboxylic acid, 4-isopropylsulfanyl-1,3-dimethyl-1H-pyrazolo[3,4-b] pyridine-5-carboxylic acid and 1-cyclopropyl-5-methoxy-2-methyl-2,3-dihydro-1H-indole-3-carboxylic acid, (5-(isoxazol-3-yl)-thiophen-2-yl) sulfonyl chloride, 4-bromo-1-methyl-1H-pyrazol-3-ylmethanal, 4-chloro-1H-pyrazol-3-ylmethanal and 1-(4-chloro-benzyl)-1H-pyrazol-3-ylmethanal are available from Maybridge Chemical Company Ltd.; Trevillett, Tintagel, Cornwall PL34 0HW, UK;

(5-methanesulfonyl-1H-indol-2-yl)carboxylic acid is available by hydrolysis of an ester available from Maybridge Chemical Company Ltd., details above;

(4-chloro-5-methyl-3-nitro-pyrazol-1-yl) methanecarboxylic acid, (5-methyl-3,4-dinitro-pyrazol-1-yl)methanecarboxylic acid and (2,4-dinitro-imidazol-1-yl)methanecarboxylic acid are available from ASINEX Ltd., 6 Schukinskaya ulitsa, Moscow 123182, Russia;

(6-(imidazol-1-yl)-pyridin-3-yl)carboxylic acid and 2-methyl-2-([1,2,4]triazol-1-yl)-propanoic acid are available from Bionet Research Ltd, 3 Highfield Industrial Estate, Camelford, Cornwall PL32 9QZ, UK; and, (2-methyl-[1,8]naphthyridin-3-yl)carboxylic acid, (2-methyl-[1,6]naphthyridin-3-yl)carboxylic acid and (5-trifluoromethyl-thieno[3,2-b]pyridin-6-yl)-methanecarboxylic acid are available from Peakdale Fine Chemicals Ltd., 7 Brookfield Industrial Estate, Glossop, Derbyshire, SK13 6LQ, UK.

EXAMPLE 28

Pharmacological Analysis: Calcium Flux $[Ca^{2+}]_i$ Assay

Human Eosinophils

Human eosinophils were isolated from EDTA anticoagulated peripheral blood as previously described (Hansel et al., J. Immunol. Methods, 1991, 145, 105–110). The cells were resuspended (5×10$^6$ ml$^{-1}$) and loaded with 5 μM FLUO-3/ AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

Human Eosinophil Chemotaxis

Human eosinophils were isolated from EDTA anticoagulated peripheral blood as previously described (Hansel et al., J. Immunol. Methods, 1991, 145, 105–110). The cells were resuspended at 10×10$^6$ ml$^{-1}$ in RPMI containing 200 IU/ml penicillin, 200 μg/ml streptomycin sulphate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton×100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Compounds of the Examples were found to be antagonists of the eotaxin mediated human eosinophil chemotaxis.

EXAMPLE 29

Guinea-Pig Isolated Trachea (See for example, Harrison, R. W. S., Carswell, H. & Young, J. M. (1984) European J. Pharmacol., 106, 405–409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM): NaCl 117.6, NaH$_2$PO$_4$ 0.9, NaHCO$_3$ 25.0, MgSO$_4$ 1.2, KCl 5.4, CaCl$_2$ 2.6 and glucose 11.1. The buffer was maintained at 37° C. and gassed with 5% CO$_2$ in oxygen. Indomethacin (2.8 μM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 log$_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[A$_{50}$] values) of histamine in the absence and presence of the test compound. Affinity (pA$_2$) values of test compounds were subsequently calculated using the following equation:

$$log(r-1) = log[B] + pA_2$$

where r=[A]$_{50}$ in presence of test compound/[A]$_{50}$ in absence of antagonist and [B] is the concentration of test compound. Compounds of the Examples were found to be H1 antagonists.

What is claimed is:

1. A compound of formula (I):

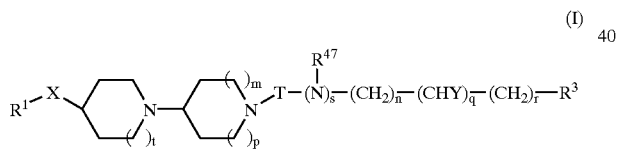

(I)

wherein:

q=0 or 1; s=0; t=1;

n and r are, independently, 0, 1, 2, 3, 4 or 5;

p=1; m=1;

X is O;

Y is NHR$^2$ or OH;

T is C(O), C(S), S(O)$_2$ or CH$_2$;

R$^1$ is phenyl or naphthyl optionally substituted as presecribed below for aryl moieties;

R$^2$ and R$^{47}$ are, independently, hydrogen, C$_{1-6}$ alkyl, aryl(C$_{1-4}$)alkyl or CO(C$_{1-6}$ alkyl);

R$^3$ is aryl, optionally substituted as presecribed below;

wherein, unless stated otherwise, the foregoing aryl moieties are optionally substituted by: (a) halogen, (b) OH, (c) SH, (d) NO$_2$, (e) oxo, (f) C$_{1-6}$ alkyl, the alkyl being optionally substituted by halogen, OC(O)C$_{1-6}$ alkyl, S(O)$_2$R$^{48}$, phenyl, the phenyl being optionally substituted by halogen (such as one or two chlorine or fluorine atoms), C$_{1-6}$ alkyl, S(O)$_2$R$^{38}$ or C(O)NR$^{39}$R$^{40}$) naphthyloxy, the naphthyloxy being optionally substituted by halo or C$_{2-6}$ alkenyl, C$_{3-10}$ cycloalkyl, the cycloalkyl being optionally substituted by C$_{1-4}$ alkyl or oxo) or NR$^{41}$C(O)OCH$_2$(fluoren-9-yl);

(g) NR$^{41}$C(O)OCH$_2$(fluoren-9-yl), (h) C$_{1-6}$ alkoxy, the C$_{1-6}$ alkox being optionally substituted by halogen, C$_{1-6}$ alkoxy, NHCO$_2$(C$_{1-6}$ alkyl), CO$_2$R$^4$, NR$^5$R$^6$ or phenyl, the phenyl being optionally substituted by halogen or NO$_2$;

(i) C$_{1-6}$ alkylthio, (j) C$_{1-6}$ haloalkylthio, (k) C$_{3-10}$ cycloalkyl, (l) NR$^7$R$^8$, (m) NR$^9$C(O)R$^{10}$, (n) CO$_2$R$^{11}$ (o) C(O)NR$^{12}$R$^{13}$, (p) C(O)R$^{14}$, (q) S(O)$_d$R$^{15}$, (r) S(O)$_2$NR$^{42}$R$^{43}$, (s) NR$^{44}$S(O)$_2$R$^{45}$, (t) phenyl, the phenyl being optionally substituted by halogen, C$_{1-6}$ alkyl, C$_{1-6}$ haloalkyl, CN, NO$_2$, C$_{1-6}$ alkoxy, the alkoxy being optionally substituted by halogen, or OH, phenyl, the phenyl being optionally substituted by halogen, C$_{1-6}$ alkyl, C$_{1-6}$ haloalkyl, CN, NO$_2$, C$_{1-6}$ alkoxy or C$_{1-6}$ haloalkoxy, (u) phenoxy, the phenoxy being optionally substituted by halogen, C$_{1-6}$ alkyl, C$_{1-6}$ haloalkyl, CN, NO$_2$, C$_{1-6}$ alkoxy, C$_{1-6}$ haloalkoxy, phenyl, the phenyl being optionally substituted by halogen, C$_{1-6}$ alkyl, C$_{1-6}$ haloalkyl, CN, NO$_2$, C$_{1-6}$ alkoxy or C$_{1-6}$ haloalkoxy, (v) SCN, (w) CN, (x) SO$_3$H (or an alkali metal salt thereof), (y) methylenedioxy or (z) difluoromethylenedioxy; when aryl is phenyl adjacent substituents may join to form, together with the phenyl ring to which they are attached, a dihycfrophenanthrene moiety; d is 0, 1 or 2;

R$^4$, R$^5$, R$^6$, R$^7$, R$^8$, R$^9$, R$^{10}$, R$^{11}$, R$^{12}$, R$^{13}$, R$^{14}$, R$^{37}$, R$^{39}$, R$^{40}$, R$^{41}$, R$^{42}$, R$^{43}$ and R$^{44}$ are, independently, hydrogen, C$_{1-6}$ alkyl, aryl, the aryl being optionally substituted by halogen, C$_{1-6}$ alkyl, C$_{1-6}$ haloalkyl, CN, NO$_2$, C$_{1-6}$ alkoxy or C$_{1-6}$ haloalkoxy;

R$^{15}$, R$^{38}$, R$^{45}$ and R$^{48}$ are, independently, C$_{1-6}$ alkyl, the alkyl being optionally substituted by halogen, hydroxy or C$_{3-10}$ cycloalkyl, C$_{3-6}$ alkenyl, aryl, the aryl being optionally substituted by halogen, C$_{1-6}$ alkyl, C$_{1-6}$ haloalkyl, CN, NO$_2$, C$_{1-6}$ alkoxy or C$_{1-6}$ haloalkoxy;

or an N-oxide thereof; or a pharmaceutically acceptable salt thereof; or a solvate thereof.

2. A compound as claimed in claim 1 wherein n is 0 or 1.

3. A compound as claimed in claim 1 wherein q and r are both 0.

4. A compound as claimed in claim 1 wherein R$^1$ is phenyl substituted with one or more of fluorine, chlorine, C$_{1-4}$ alkyl or C$_{1-4}$ alkoxy.

5. A compound of formula (Ia″):

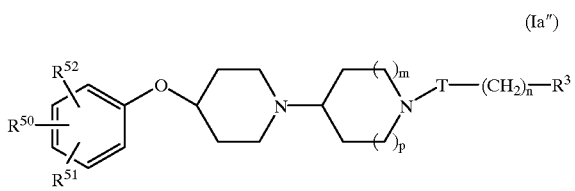

(Ia″)

wherein:

T is C(O), C(S), S(O)$_2$ or CH$_2$;

n is 1;

n and p are 1;

R$^{50}$ is hydrogen, cyano, S(O)$_2$(C$_{1-4}$ alkyl), S(O)$_2$(C$_{1-4}$ haloalkyl), halogen, C$_{1-4}$ alkyl, C$_{1-4}$ haloalkyl, C$_{1-4}$ alkoxy or phenyl, said phenyl being optionally substituted by one or two halogen atoms or by one C(O)NR$^{12'}$R$^{13'}$, NR$^{9'}$C(O)R$^{10'}$, S(O)$_2$R$^{15'}$, S(O)$_2$NR$^{42}$R$^{43}$ or NR$^{44}$S(O)$_2$R$^{45}$ group;

R$^{51}$ and R$^{52}$ are, independently, hydrogen, halogen, C$_{1-4}$ alkyl or C$_{1-4}$ alkoxy; R$^3$ is aryl; wherein, unless stated otherwise, the foregoing aryl moieties are optionally substituted by: halogen, OH, SH, NO$_2$, oxo, C$_{1-6}$ alkyl, said alkyl being optionally substituted by halogen, OC(O)C$_{1-6}$ alkyl, phenyl, said phenyl being optionally substituted by halo or C$_{1-6}$ alkyl, naphthyloxy, said naphthyloxy being optionally substituted by halo or C$_{2-6}$ alkenyl, or NR$^4$C(O)OCH$_2$fluoren-9-yl)), C$_{1-6}$ alkoxy, said C$_{1-6}$ alkoxy being optionally substituted by halogen, CO$_2$R$^4$,NR$^5$R$^6$ or phenyl, said phenyl being optionally substituted by halogen or NO$_2$, C$_{1-6}$ alkylthio, nitro, C$_{3-7}$ cycloalkyl, NR$^7$R$^8$, NR$^9$C(O)R$^{10}$, CO$_2$R$^{11}$, C(O)NR$^{12}$R$^{13}$, C(O)R$^{14}$, S(O)$_2$R$^{15}$, phenyl, said phenyl being optionally substituted by NO$_2$ or C$_{1-6}$ alkoxy, said C$_{1-6}$ alkoxy being optionally substituted by OH, phenoxy, SCN, CN, SO$_3$H (or an alkali metal salt thereof) or methylenedioxy; when aryl is phenyl adjacent substituents may join to form, together with the phenyl ring a dihydrophenanthrene moiety;

R$^4$, R$^5$, R$^6$, R$^7$, R$^8$, R$^9$, R$^{9'}$, R$^{10}$, R$^{10'}$, R$^{11}$, R$^{12}$, R$^{12'}$, R$^{13}$, R$^{13'}$, R$^{14}$, R$^{42}$, R$^{43}$ and R$^{44}$ are, independently, hydrogen, C$_{1-6}$ alkyl or phenyl;

R$^{15}$, R$^{15'}$ and R$^{45}$ are, independently, C$_{1-6}$ alkyl or phenyl; or a pharmaceutically acceptable salt thereof.

6. A compound as claimed in claim 1 wherein T is C(O), S(O)$_2$ or CH$_2$.

7. A compound of formula (If):

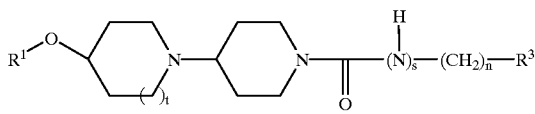

(If)

wherein R$^1$, n, t, s and R$^3$ are as defined in claim 1.

8. A compound as claimed in claim 1 wherein R$^3$ is phenyl optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{46}$ (wherein k is 0, 1 or 2; and R$^{46}$ is C$_{1-4}$ alkyl, C$_{1-4}$ hydroxyalkyl, C$_{3-7}$ cycloalkyl(C$_{1-4}$ alkyl) or phenyl), C$_{1-4}$ haloalkylthio, C(O)NH$_2$, NHS(O)$_2$(C$_{1-4}$ alkyl), S(O)$_2$NH$_2$, S(O)$_2$NH (C$_{1-4}$ alkyl) or S(O)$_2$N(C$_{1-4}$ alkyl)$_2$.

9. A compound as claimed in claim 5 wherein n is 0 or 1.

10. A compound as claimed in claim 7 wherein R$^1$ is phenyl substituted with one or more of fluorine, chlorine, C$_{1-4}$ alkyl or C$_{1-4}$ alkoxy.

11. A process for preparing a compound of formula (I) as claimed in claim 1, which comprises:

a) when R$^{47}$ is not hydrogen, coupling a compound of formula (II):

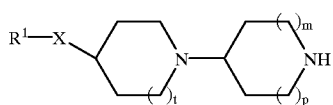

(II)

with a compound of formula (III):

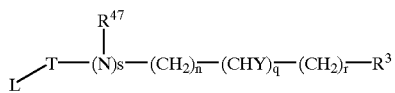

(III)

wherein L is a suitable leaving group, and the variables Y and T are optionally protected during the course of the reaction;

b) when s is 1, R$^{47}$ is hydrogen and T is CO, reacting a compound of formula (II):

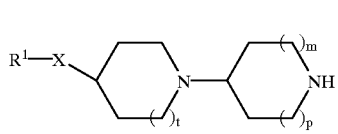

(II)

with an isocyanate O=C=N—(CH$_2$)$_n$—(CH$_2$)$_r$—R$^3$;

c) reductively aminating of a compound of formula (XX):

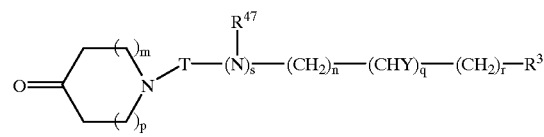

(XX)

with an amine of formula (XXI):

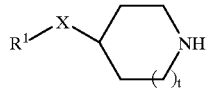

(XXI)

d) performing a fluoride displacement reaction on F-R$^1$ in the presence of compound of formula (XVIII):

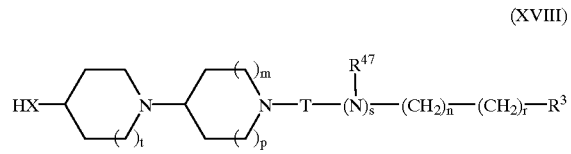

(XVIII)

provided that R$^{47}$ is not hydrogen.

12. A pharmaceutical composition which comprises a compound of the formula (I), or a pharmaceutically acceptable salt thereof or a solvate thereof, and a pharmaceutically acceptable adjuvant, diluent or carrier.

13. A method of treating asthma or rhinitis, said method comprising administering to a warm blooded animal a compound of the formula (I) as claimed in claim 1 or a pharmaceutically acceptable salt thereof or a solvate thereof in an amount effective to treat asthma or rhinitis.

* * * * *